US012502398B2

(12) United States Patent
Doshi et al.

(10) Patent No.: US 12,502,398 B2
(45) Date of Patent: Dec. 23, 2025

(54) COMBINATION THERAPY FOR TREATING CANCER

(71) Applicant: AstraZeneca AB, Sodertalje (SE)

(72) Inventors: Aatman Doshi, Waltham, MA (US); Alwin Schuller, Waltham, MA (US); Susan Cantin, Waltham, MA (US)

(73) Assignee: AstraZeneca AB, Sodertalje (SE)

( * ) Notice: Subject to any disclaimer, the term of this patent is extended or adjusted under 35 U.S.C. 154(b) by 858 days.

(21) Appl. No.: 17/755,602

(22) PCT Filed: Nov. 2, 2020

(86) PCT No.: PCT/IB2020/060275

§ 371 (c)(1),
(2) Date: May 3, 2022

(87) PCT Pub. No.: WO2021/090146

PCT Pub. Date: May 14, 2021

(65) Prior Publication Data

US 2022/0409642 A1 Dec. 29, 2022

Related U.S. Application Data

(60) Provisional application No. 62/930,054, filed on Nov. 4, 2019.

(51) Int. Cl.

| | |
|---|---|
| ***A61K 31/69*** | (2006.01) |
| ***A61P 35/00*** | (2006.01) |
| ***C07K 16/28*** | (2006.01) |

(52) U.S. Cl.

CPC .............. *A61K 31/69* (2013.01); *A61P 35/00* (2018.01); *C07K 16/2803* (2013.01); *C07K 16/2818* (2013.01); *C07K 16/2827* (2013.01)

(58) Field of Classification Search

CPC ..... A61K 31/69; A61P 35/00; C07K 16/2803; C07K 16/2818; C07K 16/2827

See application file for complete search history.

(56) References Cited

U.S. PATENT DOCUMENTS

| | | | | |
|---|---|---|---|---|
| 11,420,984 B2 * | 8/2022 | Mlynarski | ............... | A61P 35/00 |
| 11,912,727 B2 * | 2/2024 | Mlynarski | ............... | A61P 35/00 |
| 12,195,485 B2 * | 1/2025 | Mlynarski | ............... | A61P 35/00 |
| 2018/0214544 A1 | 8/2018 | Mitchell et al. | | |

FOREIGN PATENT DOCUMENTS

WO 2019/159120 A1 8/2019

OTHER PUBLICATIONS

Munder, British Journal of Pharmacology, 2009, 158, 638-651 (Year: 2009).*

Pham, Drug Discovery Today, vol. 23, No. 4, Apr. 2018 (Year: 2018).*

International Search Report for corresponding PCT/IB2020/060275 for corresponding PCT/IB2020/060275 mailed February 2. 2021.

* cited by examiner

*Primary Examiner* — Andrew D Kosar
*Assistant Examiner* — Phillip Matthew Rzeczycki
(74) *Attorney, Agent, or Firm* — AstraZeneca Global IP

(57) ABSTRACT

The present disclosure provides methods of treating cancer in a patient. The method comprises administering to the patient an effective amount of a compound of Formula (Ia) or (Ib), or a pharmaceutically acceptable salt thereof, and an effective amount of an immunomodulatory agent. Also provided herein are compositions and kits for performing the methods described herein. In another aspect, the method comprises administering to the patient an effective amount of a compound of Formula (Ia) or (Ib), or a pharmaceutically acceptable salt thereof, and an effective amount of radiation therapy.

19 Claims, 9 Drawing Sheets

Specification includes a Sequence Listing.

Vehicle
Arginase inh 30 mg/kg
anti PD-L1 10 mg/kg
anti PDL1 + Arginase inh

SEQUENCE LISTING

<160> NUMBER OF SEQ ID NOS: 24

<210> SEQ ID NO 1
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 1

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105
```

<210> SEQ ID NO 2
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120
```

<210> SEQ ID NO 3
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 3

Gly Phe Thr Phe Ser Arg Tyr Trp Met Ser
1 5 10

<210> SEQ ID NO 4
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 4

Asn Ile Lys Gln Asp Gly Ser Glu Lys Tyr Tyr Val Asp Ser Val Lys
1 5 10 15

Gly

<210> SEQ ID NO 5
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 5

Glu Gly Gly Trp Phe Gly Glu Leu Ala Phe Asp Tyr
1 5 10

<210> SEQ ID NO 6
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 6

Arg Ala Ser Gln Arg Val Ser Ser Ser Tyr Leu Ala
1 5 10

<210> SEQ ID NO 7
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 7

Asp Ala Ser Ser Arg Ala Thr
1 5

<210> SEQ ID NO 8
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 8

Gln Gln Tyr Gly Ser Leu Pro Trp Thr
1 5

<210> SEQ ID NO 9
<211> LENGTH: 139
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

Pro Ser Ser Leu Ser Ala Ser Val Gly Asp Arg Val Thr Ile Thr Cys
1 5 10 15

Arg Ala Ser Gln Ser Ile Asn Ser Tyr Leu Asp Trp Tyr Gln Gln Lys
20 25 30

Pro Gly Lys Ala Pro Lys Leu Leu Ile Tyr Ala Ala Ser Ser Leu Gln
35 40 45

Ser Gly Val Pro Ser Arg Phe Ser Gly Ser Gly Ser Gly Thr Asp Phe
50 55 60

Thr Leu Thr Ile Ser Ser Leu Gln Pro Glu Asp Phe Ala Thr Tyr Tyr
65 70 75 80

Cys Gln Gln Tyr Tyr Ser Thr Pro Phe Thr Phe Gly Pro Gly Thr Lys
85 90 95

Val Glu Ile Lys Arg Thr Val Ala Ala Pro Ser Val Phe Ile Phe Pro
100 105 110

Pro Ser Asp Glu Gln Leu Lys Ser Gly Thr Ala Ser Val Val Cys Leu
115 120 125

Leu Asn Asn Phe Tyr Pro Arg Glu Ala Lys Val
130 135

<210> SEQ ID NO 10
<211> LENGTH: 167
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 10

Gly Val Val Gln Pro Gly Arg Ser Leu Arg Leu Ser Cys Ala Ala Ser
1 5 10 15

Gly Phe Thr Phe Ser Ser Tyr Gly Met His Trp Val Arg Gln Ala Pro
20 25 30

Gly Lys Gly Leu Glu Trp Val Ala Val Ile Trp Tyr Asp Gly Ser Asn
35 40 45

Lys Tyr Tyr Ala Asp Ser Val Lys Gly Arg Phe Thr Ile Ser Arg Asp
50 55 60

Asn Ser Lys Asn Thr Leu Tyr Leu Gln Met Asn Ser Leu Arg Ala Glu
65 70 75 80

Asp Thr Ala Val Tyr Tyr Cys Ala Arg Asp Pro Arg Gly Ala Thr Leu
85 90 95

Tyr Tyr Tyr Tyr Tyr Gly Met Asp Val Trp Gly Gln Gly Thr Thr Val
100 105 110

Thr Val Ser Ser Ala Ser Thr Lys Gly Pro Ser Val Phe Pro Leu Ala
115 120 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His
                165

<210> SEQ ID NO 11
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 11

Gly Phe Thr Phe Ser Ser Tyr Gly Met His
1               5                   10

<210> SEQ ID NO 12
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 12

Val Ile Trp Tyr Asp Gly Ser Asn Lys Tyr Tyr Ala Asp Ser Val
1               5                   10                  15

<210> SEQ ID NO 13
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 13

Thr Ala Val Tyr Tyr Cys Ala Arg Asp Pro Arg Gly Ala Thr Leu Tyr
1               5                   10                  15

Tyr Tyr Tyr Tyr Gly Met Asp Val
            20

<210> SEQ ID NO 14
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 14

Arg Ala Ser Gln Ser Ile Asn Ser Tyr Leu Asp
1               5                   10

<210> SEQ ID NO 15
<211> LENGTH: 7
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic peptide"

<400> SEQUENCE: 15

```
Ala Ala Ser Ser Leu Gln Ser
1               5
```

<210> SEQ ID NO 16
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

```
Gln Gln Tyr Tyr Ser Thr Pro Phe Thr
1               5
```

<210> SEQ ID NO 17
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Met Asn Trp Val Arg Gln Met Pro Gly Lys Gly Leu Glu Trp Met
        35                  40                  45

Gly Arg Ile Asp Pro Tyr Asp Ser Glu Thr His Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
```

```
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450


<210> SEQ ID NO 18
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Asn Trp Val Gln Gln Ala Pro Gly Lys Gly Leu Glu Trp Met
        35                  40                  45

Gly Arg Ile Asp Pro Tyr Asp Ser Glu Thr His Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Gly Tyr Asp Phe Asp Val Gly Thr Leu Tyr Trp Phe Phe
            100                 105                 110

Asp Val Trp Gly Gln Gly Thr Thr Val Thr Val Ser Ser Ala Ser Thr
        115                 120                 125
```

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Trp Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Trp Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Trp Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 19
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 19

Ser Tyr Trp Met Asn
1               5

<210> SEQ ID NO 20
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 20

```
Arg Ile Asp Pro Tyr Asp Ser Glu Thr His Tyr Ala Glu Lys Phe Gln
1               5                   10                  15

Gly
```

<210> SEQ ID NO 21
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 21

```
Tyr Cys Ala Thr Gly Gly Tyr Asp
1               5
```

<210> SEQ ID NO 22
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 22

```
Gly Ser Gly Tyr Ser Phe Thr Ser Tyr Trp Met
1               5                   10
```

<210> SEQ ID NO 23
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 23

```
Arg Ile Asp Pro Tyr Asp Ser
1               5
```

<210> SEQ ID NO 24
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 24

```
Ser Asp Thr Ala Met Tyr Tyr Cys Ala
1               5
```

COMBINATION THERAPY FOR TREATING CANCER

CROSS-REFERENCE TO RELATED APPLICATIONS

This application is a U.S. National Stage application of International Application No. PCT/IB2020/060275, filed on Nov. 2, 2020, said International Application No. PCT/IB2020/060275 claims benefit under 35 U.S.C. § 119 (e) of the U.S. Provisional Application No. 62/930,054, filed Nov. 4, 2019. Each of the above listed applications is incorporated by reference herein in its entirety for all purposes.

REFERENCE TO THE SEQUENCE LISTING

This application incorporates by reference a Sequence Listing submitted with this application as text file entitled, created on, and having a size of kilobytes.

BACKGROUND

Arginase is a manganese metalloenzyme that catalyzes the conversion of L-arginine to urea and L-ornithine. Two isoforms, Arginase 1 and Arginase 2, exist. Although L-arginine is not an essential amino acid as it can be provided through protein turnover in healthy adults, increased expression and secretion of arginases results in reduced L-arginine levels in various physiologic and pathologic conditions (e.g., pregnancy, auto-immune diseases, cancer). Immune cells are particularly sensitive to reduced L-arginine levels. Tumors use multiple immune suppressive mechanisms to evade the immune system. One of these is the reduction of L-arginine through increased levels of circulating arginase, increased expression and secretion of arginase by tumor cells, and recruitment of arginase expressing and secreting myeloid derived suppressor cells. Together, these lead to a reduction of L-arginine in the tumor microenvironment and an immune-suppressive phenotype. Pharmacologic inhibition of arginase activity has been shown to reverse the low L-arginine induced immune suppression in animal models. However, there are many proteins and pathways involved in cancer and the research thereof has been advanced rapidly. As such, there is a need for new cancer therapies for patients.

SUMMARY

In some embodiments, the present disclosure provides a method of treating cancer in a patient comprising administering to the patient an effective amount of a compound of Formula (Ia) or (Ib), or a pharmaceutically acceptable salt thereof, and an effective amount of an immunomodulatory agent;

(Ia)

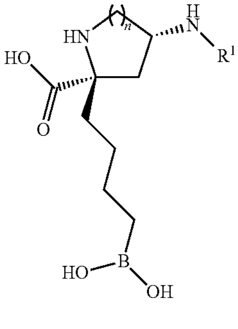

or

-continued (Ib)

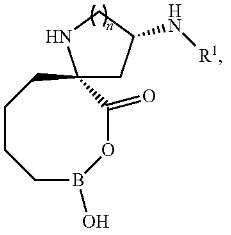

n is zero or 1;

$R^1$ is —H or —C(O)CH($R^{1a}$)NH$R^{1b}$;

$R^{1a}$ is selected from —H, —($C_1$-$C_6$) alkyl and $CH_2OR^{1c}$;

$R^{1b}$ is —H; or alternatively, $R^{1a}$ and $R^{1b}$, together with the atom to which they are attached, form a 5-membered heterocyclic ring; and $R^{1c}$ is H or —$CH_3$.

In some embodiments, the present disclosure provides a method of treating cancer in a patient comprising administering to the patient an effective amount of the compound of Formula (Ia) or (Ib), or a pharmaceutically acceptable salt thereof, and an effective amount of radiation therapy. In some embodiments, the method further comprises administering to the patient an effective amount of an immunomodulatory agent.

In some embodiments, the radiation therapy is fractionated radiation therapy.

In some embodiments of Formula (Ia) or (Ib), $R^1$ is —H or —C(O)CH($R^{1a}$)$NH_2$; and $R^{1a}$ is selected from —H or —($C_1$-$C_6$) alkyl.

In some embodiments of Formula (Ia) or (Ib), the compound is represented by Formula (IIa) or (IIb):

(IIa)

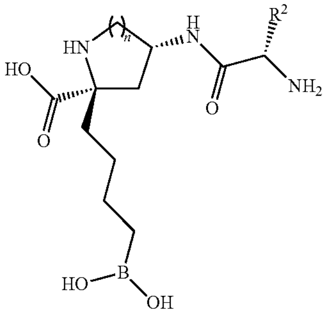

or (IIb)

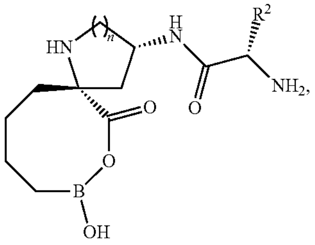

wherein n is zero or 1; and $R^2$ is selected from —H or —($C_1$-$C_4$) alkyl.

In some embodiments, the immunomodulatory agent is an immune checkpoint inhibitor or an immunostimulant. In some embodiments, the immune checkpoint inhibitor is selected from a CTLA-4 receptor inhibitor, PD-1 receptor inhibitor, PD-L1 inhibitor, PD-L2 inhibitor, a NKG2A receptor inhibitor, and a combination thereof. In some embodiments, the immunostimulant is a TLR3 agonist.

In some embodiments, the immune checkpoint inhibitor is an antibody or antigen-binding fragment thereof.

In some embodiments, the immune checkpoint inhibitor is an anti-CTLA-4 receptor antibody, an anti-PD-1 receptor antibody, an anti-PD-L1 antibody, an anti-PD-L2 antibody, or an anti-NKG2A receptor antibody. In some embodiments, the immune checkpoint inhibitor is an anti-CTLA-4 receptor antibody, an anti-PD-L1 antibody, an anti-NKG2A receptor antibody, or a combination thereof.

In some embodiments, the immune checkpoint inhibitor is durvalumab, tremelimumab, monalizumab, or a combination thereof.

In some embodiments, the cancer is a breast cancer, a bladder cancer, a head and neck cancer, a non-small cell lung cancer, a small cell lung cancer, a colorectal cancer, a gastrointestinal stromal tumor, a gastroesophageal carcinoma, a renal cell cancer, a prostate cancer, a liver cancer, a colon cancer, a pancreatic cancer, an ovarian cancer, a lymphoma (including non-Hodgkin's lymphoma), a cutaneous T-cell lymphoma, or a melanoma. In some embodiments, the cancer is a hematological malignancy including multiple myeloma, acute myeloid leukemia (AML), myelodysplastic syndrome (MDS), chronic myeloid leukemia (CML), chronic lymphocytic leukaemia (CLL), chronic myelomonocytic leukemia (CMML), and diffuse large B-cell lymphoma (DLBCL).

In some embodiments, the compound of Formula (Ia) or (Ib), or a pharmaceutically acceptable salt thereof, is administered sequentially, separately or simultaneously with the immunomodulatory agent.

In some embodiments, the present disclosure provides a compound of Formula (Ia) or (Ib), or a pharmaceutically acceptable salt thereof, for use in the treatment of cancer in a patient, wherein the compound of Formula (Ia) or (Ib), or a pharmaceutically acceptable salt thereof, is administered to the patient sequentially, separately or simultaneously with an immunomodulatory agent.

In some embodiments, the present disclosure provides an immunomodulatory agent for use in the treatment of cancer, wherein the immune checkpoint inhibitor is administered to the patient sequentially, separately or simultaneously with a compound of Formula (Ia) or (Ib), or a pharmaceutically acceptable salt thereof.

BRIEF DESCRIPTIONS OF THE DRAWINGS

FIGS. 1A, 1B, 1C and 1D illustrate the reduction in tumor volume over time of arginase inhibitor (FIGS. 1A and 1B), anti-PDL1 (FIGS. 1A and 1C), and the combination of arginase inhibitor (ARG inh) and anti-PDL1 (FIGS. 1A and 1D) in a MC38-ova study.

FIGS. 2A, 2B, 2C and 2D illustrate the reduction in tumor volume over time of arginase inhibitor (FIG. 2A), the combination of arginase inhibitor and anti-PDL1 (FIG. 2B), the combination of arginase inhibitor and anti-NKG2A (FIG. 2C), and the combination of arginase inhibitor, anti-PDL1 and anti-NKG2A (FIG. 2D) in a MC38-ova study FIGS. 3A, 3B, 3C, 3D, 3E and 3F illustrate the reduction in tumor volume over time of vehicle (FIG. 3A), arginase inhibitor (FIGS. 3B, 3E and 3F), TLR3 agonist (FIGS. 3C, 3E and 3F), and the combination of arginase inhibitor and TLR3 agonist (FIGS. 3D, 3E and 3F) in a MC38-ova study FIGS. 4A, 4B and 4C illustrate the immune cell changes in the tumor with arginase inhibitor, anti-PDL1, and the combination of arginase inhibitor anti-PDL1.

DETAILED DESCRIPTION

Figure 1A:
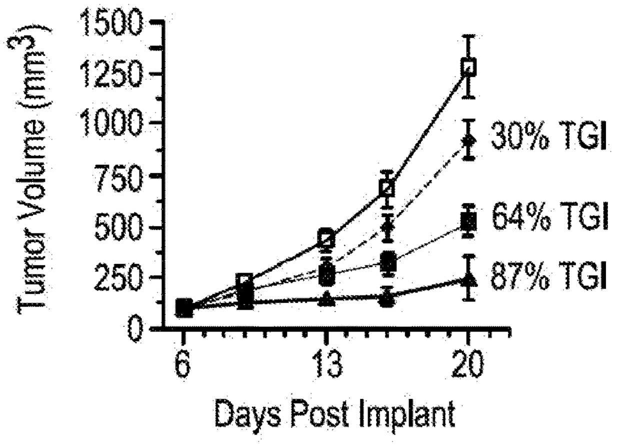
Figure 1B:
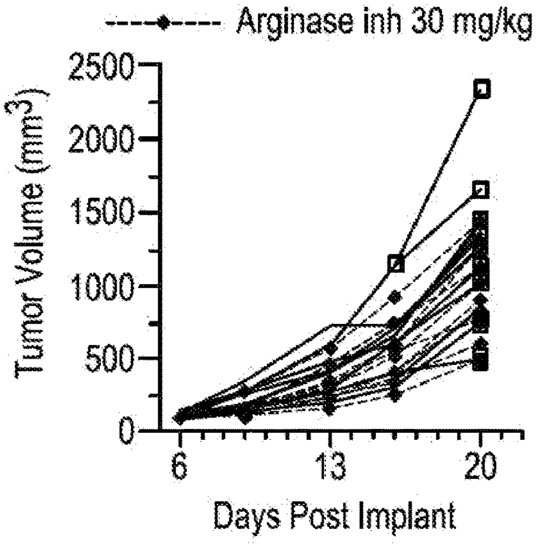
Figure 1C:
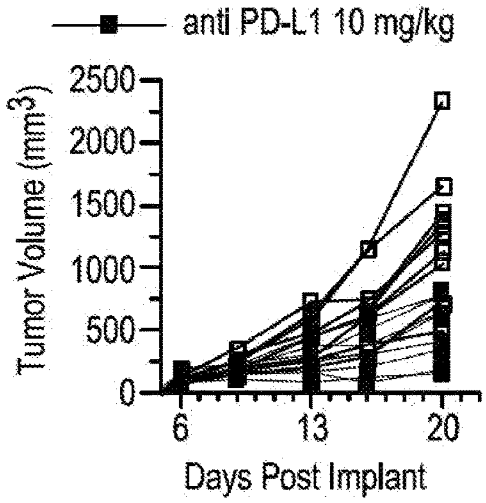
Figure 1D:
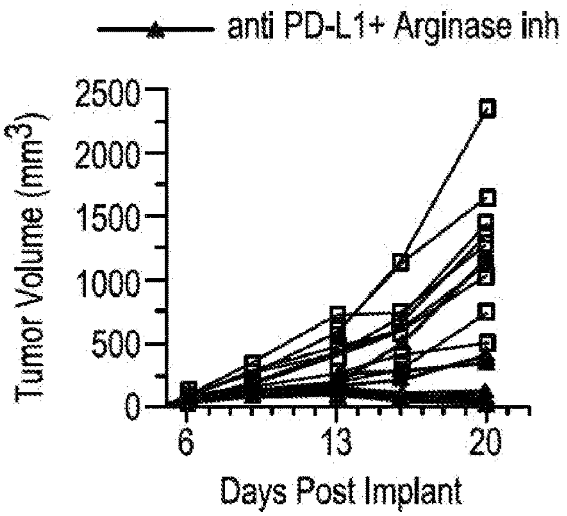
Figure 2A:
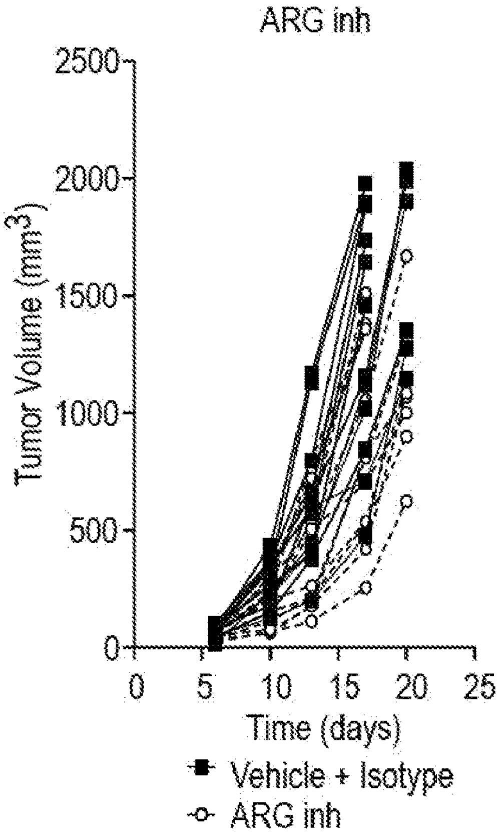
Figure 2B:
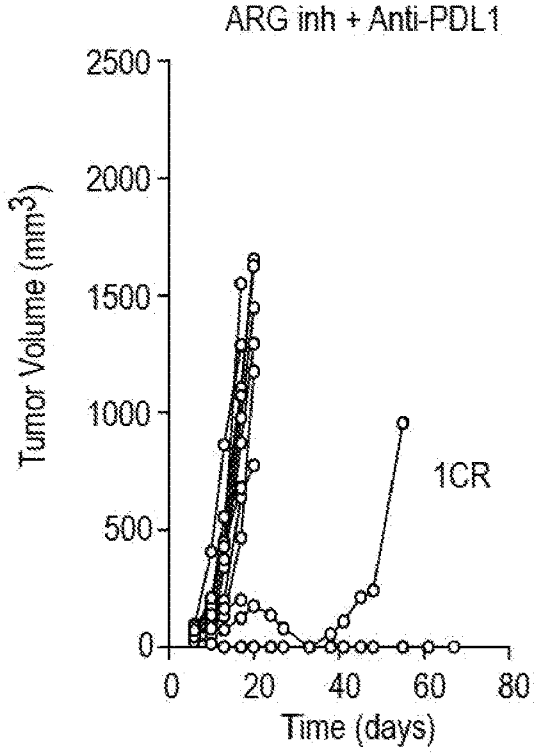
Figure 2C:
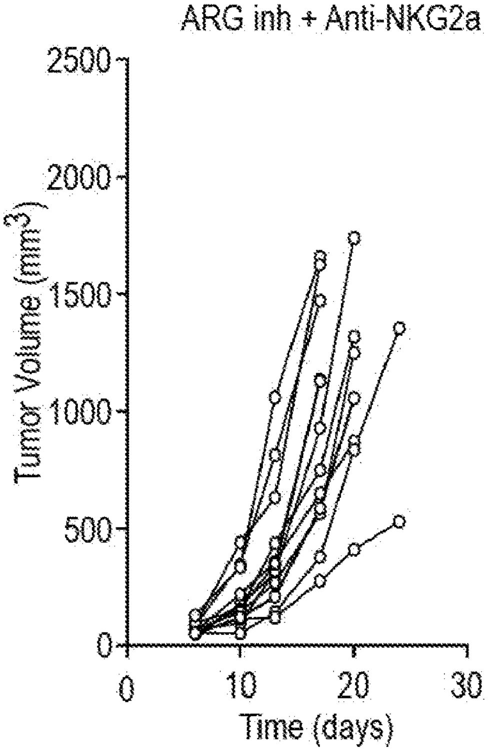
Figure 2D:
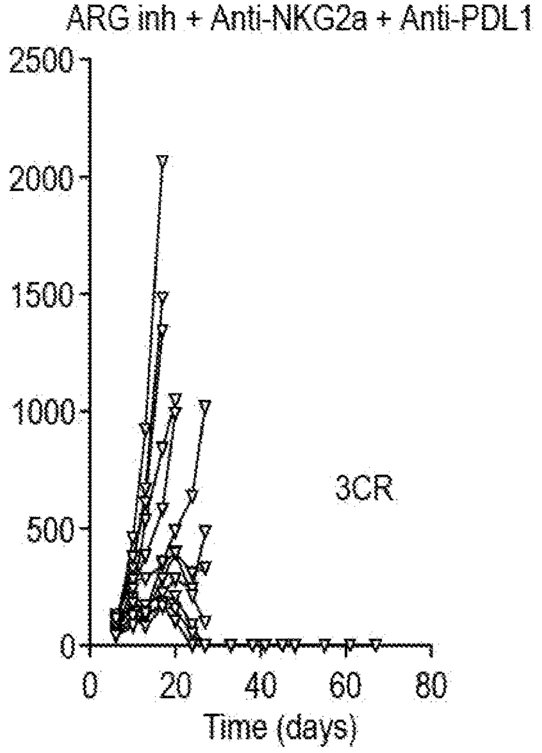
Figure 3A:
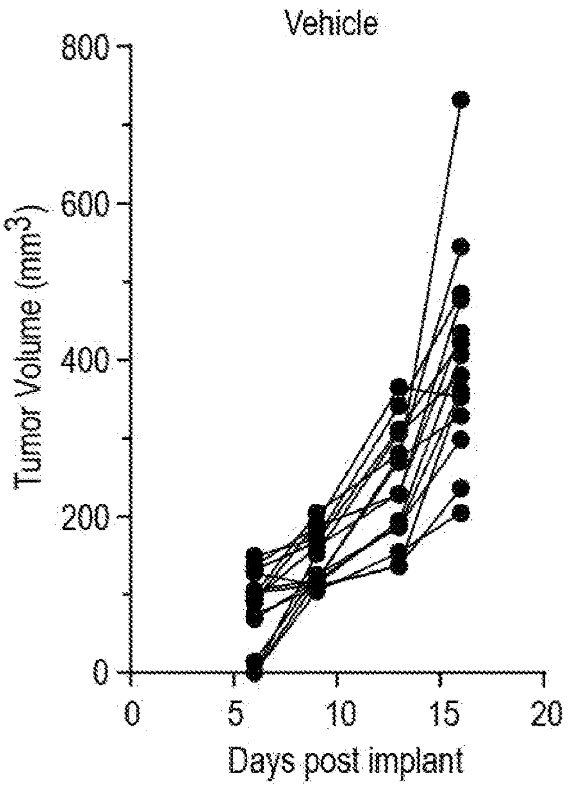
Figure 3B:
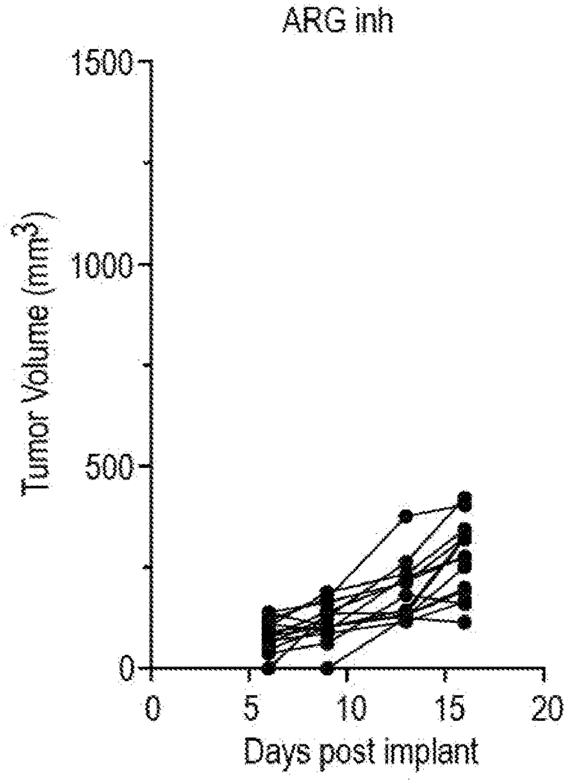
Figure 3C:
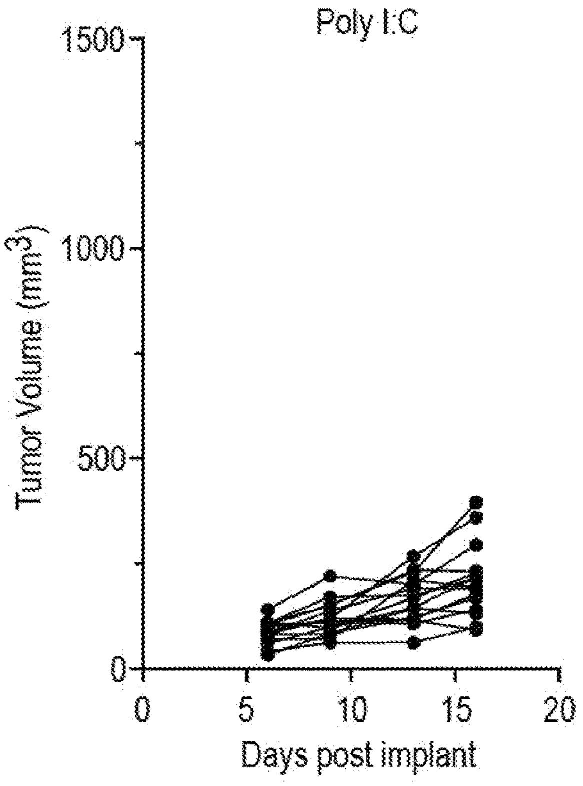
Figure 3D:
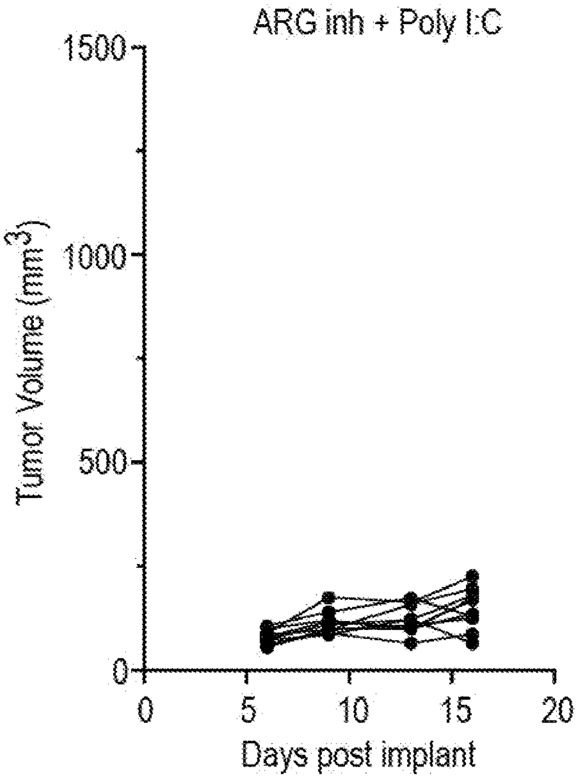
Figure 3E:
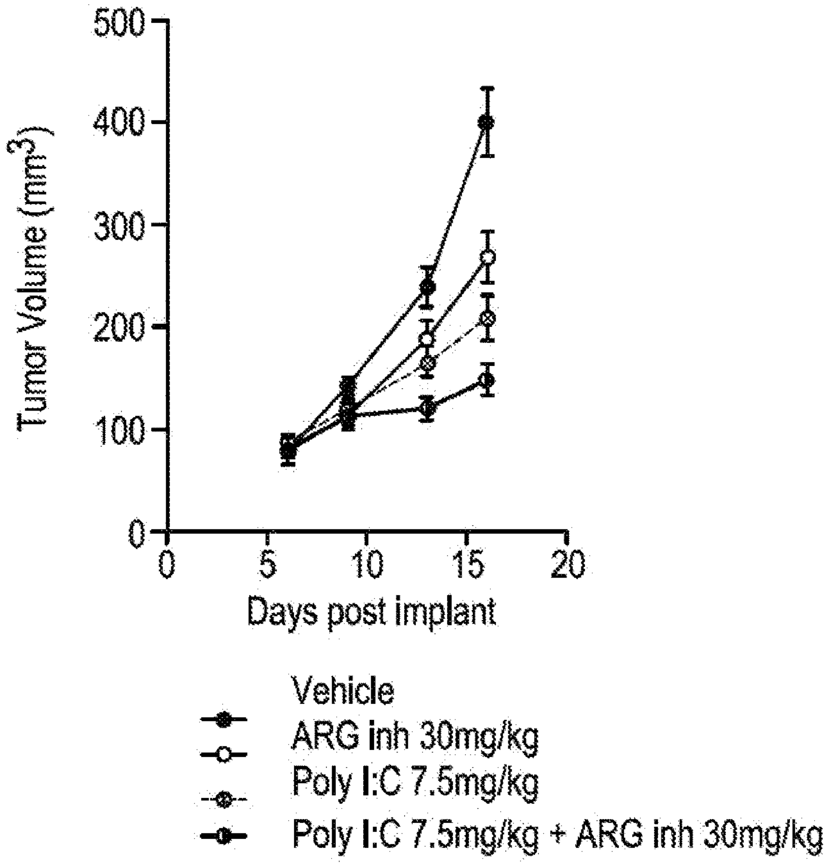
Figure 3F:
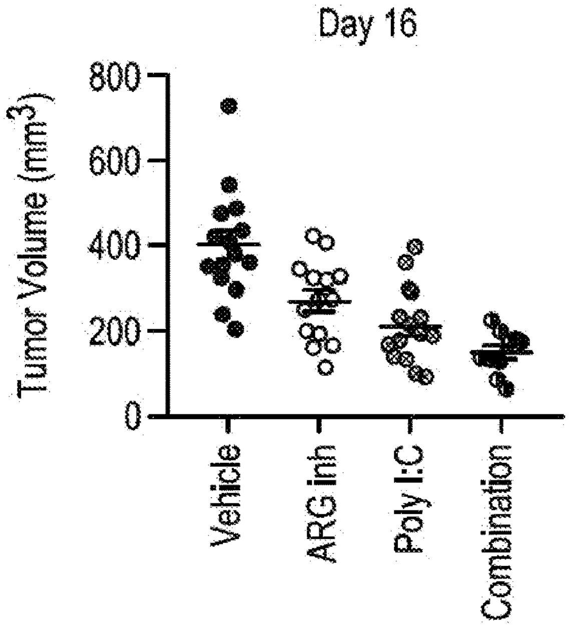
Figure 4A:
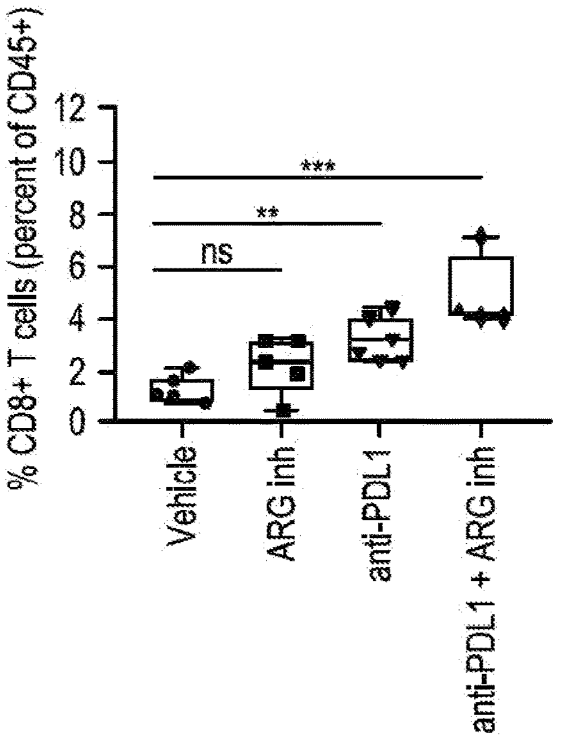
FIGS. 4D, 4E and 4F illustrate the increased CD8+ (FIGS. 4A and 4B) and CD103+ (FIG. 4F) T cell functionality in tumor draining lymph node with arginase inhibitor, anti-PDL1, and the combination of arginase inhibitor anti-PDL1.
Figure 4B:
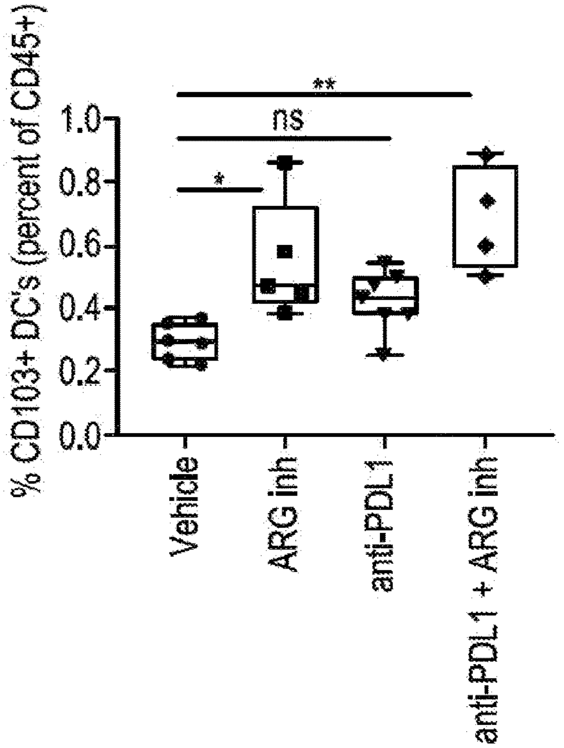
Figure 4C:
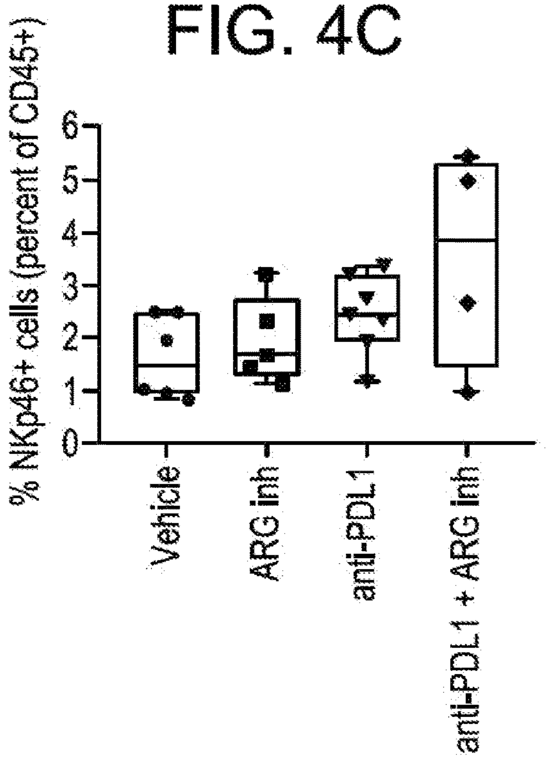
Figure 4D:
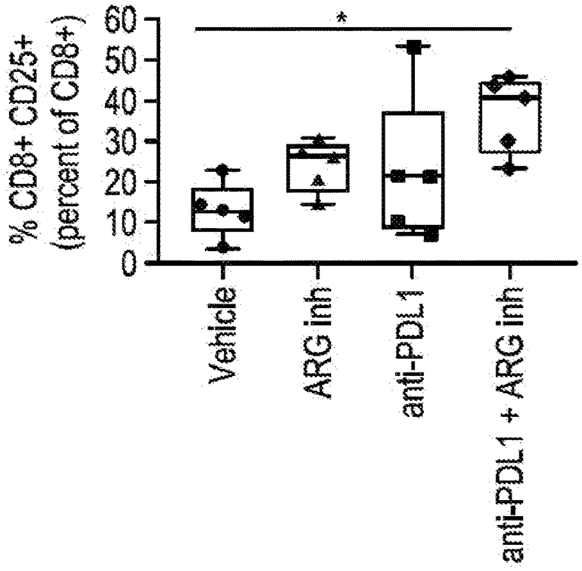
Figure 4E:
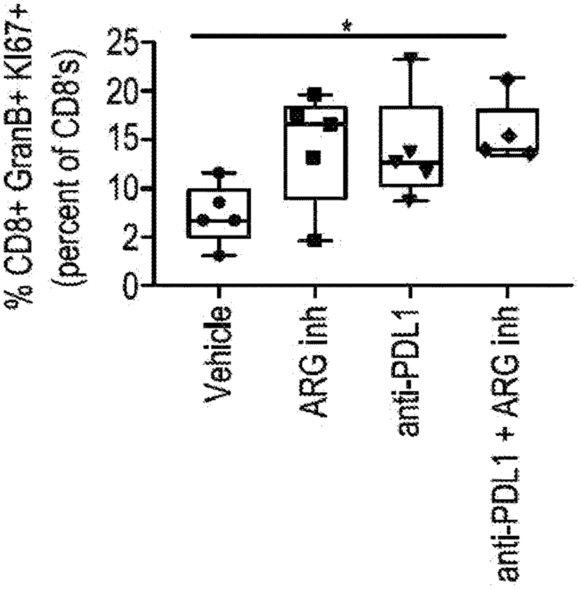
Figure 4F:
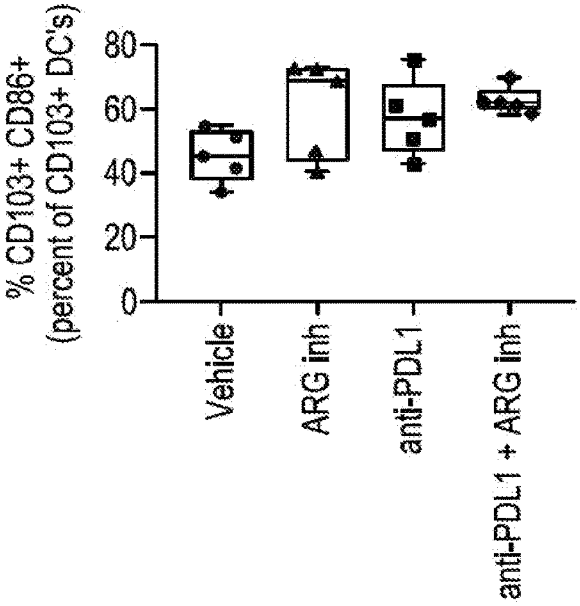

The present disclosure relates to methods of treating cancer in a patient. In one embodiment, the method comprises administering to the patient a compound of Formula (Ia) or (Ib), or a pharmaceutically acceptable salt thereof, in combination with an immunomodulatory agent. The compound of Formula (Ia) or (Ib), or any subgenus or species thereof, are useful as arginase inhibitors in therapies.

Unless otherwise modified by the term "intact," as in "intact antibodies," the term "antibody" as used herein also includes antibody fragments such as Fab, F(ab')2, Fv, scFv, Fd, dAb, and other antibody fragments that retain antigen-binding function, for example, the ability to bind, antigens such as CTLA-4, PD1, PD-L1, or NKG2A. Typically, such fragments would comprise an antigen-binding domain.

The term "mAb" refers to monoclonal antibody. Antibodies of the present disclosure can comprise, without limitation, whole native antibodies; bispecific antibodies; chimeric antibodies; Fab, Fab', single chain V region fragments (scFv); fusion polypeptides; and unconventional antibodies.

The language "treat," "treating" and "treatment" includes the reduction or inhibition of enzyme or protein activity related to arginase or cancer in a subject, amelioration of one or more symptoms of cancer in a subject, or the slowing or delaying of progression of cancer in a subject. The language "treat," "treating" and "treatment" also includes the reduction or inhibition of the growth of a tumor or proliferation of cancerous cells in a subject.

The language "inhibit," "inhibition" or "inhibiting" includes a decrease in the baseline activity of a biological activity or process.

The language "pharmaceutical composition" includes compositions comprising an active ingredient and a pharmaceutically acceptable excipient, carrier or diluent, wherein the active ingredient is a compound of Formula (Ia) or (Ib) including any subgenus or species thereof or a pharmaceutically acceptable salt thereof, or an immunomodulatory agent as described herein. The language "pharmaceutically acceptable excipient, carrier or diluent" includes compounds, materials, compositions, and/or dosage forms which are, within the scope of sound medical judgment, suitable for use in contact with the tissues of human beings and animals without excessive toxicity, irritation, allergic response, or other problem or complication, as ascertained by one of skill in the art. In some embodiments, the pharmaceutical compositions are in solid dosage forms, such as capsules, tablets, granules, powders, sachets, etc. In some embodiments, the pharmaceutical compositions are in the form of a sterile injectable solution in one or more aqueous or non-aqueous non-toxic parenterally-acceptable buffer systems, diluents, solubilizing agents, co-solvents, or carriers. A sterile injectable preparation may also be a sterile injectable aqueous or oily suspension or suspension in a non-aqueous diluent, carrier or co-solvent, which may be formulated according to known procedures using one or more of the appropriate dispersing or wetting agents and suspending agents. The pharmaceutical compositions could be a solution for iv bolus/infusion injection or a lyophilized system (either alone or with excipients) for reconstitution with a buffer system with or without other excipients. The lyophilized freeze-dried material may be prepared from non-aqueous solvents or aqueous solvents. The dosage form could also be a concentrate for further dilution for subsequent infusion.

The term "patient" includes warm-blooded mammals, for example, primates, dogs, cats, rabbits, rats, and mice. In some embodiments, the subject is a primate, for example, a human. In some embodiments, the patient has cancer. In some embodiments, the cancer is a breast cancer, a bladder cancer, a head and neck cancer, a non-small cell lung cancer (NSCLC), a small cell lung cancer, a colorectal cancer, a gastrointestinal stromal tumor, a gastroesophageal carcinoma, a renal cell cancer, a prostate cancer, a liver cancer, a colon cancer, a pancreatic cancer, an ovarian cancer, a lymphoma (including non-Hodgkin's lymphoma), a cutaneous T-cell lymphoma, or a melanoma. In some embodiments, the cancer is a hematological malignancy including multiple myeloma, acute myeloid leukemia (AML), myelodysplastic syndrome (MDS), chronic myeloid leukemia (CML), chronic lymphocytic leukaemia (CLL), chronic myelomonocytic leukemia (CMML), and diffuse large B-cell lymphoma (DLBCL).

The language "effective amount" includes that amount of a compound of Formula (Ia) or (Ib) including any subgenus or species thereof and/or that amount of an immunomodulatory agent as described herein that will elicit a biological or medical response in a subject, for example, the reduction or inhibition of enzyme or protein activity related to arginase, or cancer; amelioration of symptoms of cancer; or the slowing or delaying of progression of cancer. In some embodiments, the language "effective amount" includes the amount of a compound of Formula (Ia) or (Ib) including any subgenus or species thereof and/or an immunomodulatory agent as described herein that is effective to at least partially alleviate, inhibit, and/or ameliorate cancer or inhibit arginase, and/or reduce or inhibit the growth of a tumor or proliferation of cancerous cells in a subject.

Compounds

In one embodiment, a compound of Formula (Ia), or a pharmaceutically acceptable salt thereof, is administered in combination with an immunomodulatory agent to a subject, wherein (Ia)

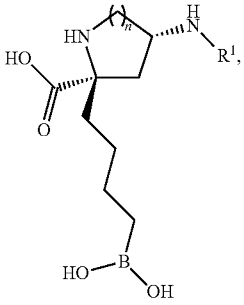

n is zero or 1;

$R^1$ is —H or —C(O)CH($R^{1a}$)NH$R^{1b}$;

$R^{1a}$ is selected from —H, —($C_1$-$C_6$) alkyl and CH$_2$O$R^{1c}$;

$R^{1b}$ is —H; or alternatively, $R^{1a}$ and $R^{1b}$, together with the atom to which they are attached, form a 5-membered heterocyclic ring; and $R^{1c}$ is H or —$CH_3$.

In one embodiment, disclosed is a compound of formula (Ia). In another embodiment, disclosed is a pharmaceutically acceptable salt of the compound of formula (Ia).

In some embodiments of formula (Ia), $R^1$ is —H or —C(O)CH($R^{1a}$)$NH_2$; and $R^{1a}$ is selected from —H or —($C_1$-$C_6$) alkyl.

In some embodiments of formula (Ia), $R^1$ is —H.

In some embodiments of formula (Ia), $R^1$ is —C(O)CH ($R^{1a}$)NH$R^{1b}$; $R^{1a}$ is —H; and $R^{1b}$ is —H.

In some embodiments of formula (Ia), $R^1$ is —C(O)CH ($R^{1a}$)NH$R^{1b}$; $R^{1a}$ is —($C_1$-$C_6$) alkyl; and $R^{1b}$ is —H.

In some embodiments of formula (Ia), $R^1$ is —C(O)CH ($R^{1a}$)NH$R^{1b}$; $R^{1a}$ is CH$_2$O$R^{1c}$; and $R^{1b}$ is —H.

In some embodiments of formula (Ia), $R^1$ is —C(O)CH ($R^{1a}$)NH$R^{1b}$; and $R^{1a}$ and $R^{1b}$, together with the atom to which they are attached, form a 5-membered heterocyclic ring.

In any of the preceding embodiments of formula (Ia), the compound is represented by any of the following structural formula:

(Ia1)

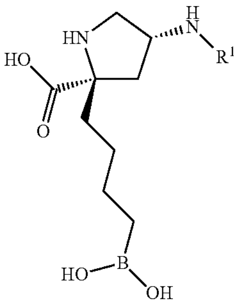

or (Ia2)

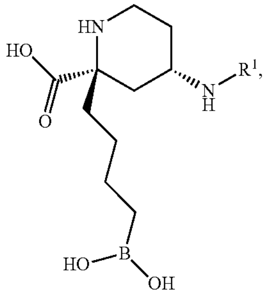

wherein $R^1$ is the same as defined above in formula (Ia).

In one embodiment, disclosed is a compound of formula (IIa), ora pharmaceutically acceptable salt thereof:

(IIa)

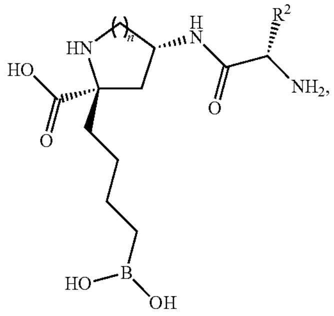

wherein n is zero or 1; and $R^2$ is selected from —H or —$(C_1\text{-}C_4)$ alkyl.

In one embodiment, disclosed is a compound of formula (IIa). In another embodiment, disclosed is a pharmaceutically acceptable salt of the compound of formula (IIa).

In some embodiments of formula (IIa), $R^3$ is —H.

In some embodiments of formula (IIa), $R^3$ is —$(C_1\text{-}C_4)$ alkyl.

In any of the preceding embodiments of formula (IIa), the compound is represented by one of the following structural formula:

(IIa1)

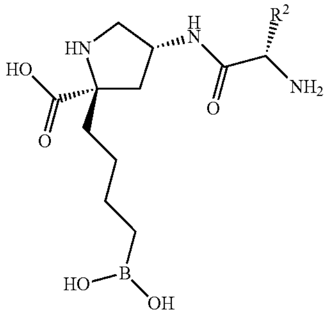

or (IIa2)

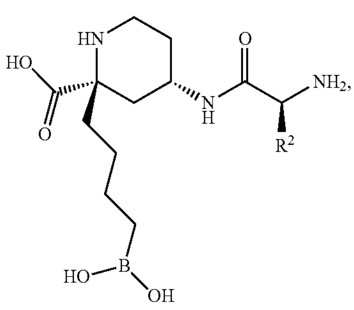

wherein $R^2$ is the same as defined above in formula (IIa).

In one embodiment, a compound of Formula (Ib), or a pharmaceutically acceptable salt thereof, is administered in combination with an immune checkpoint inhibitor to a subject, wherein (Ib)

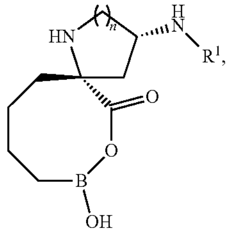

n is zero or 1;

$R^1$ is —H or —$C(O)CH(R^{1a})NHR^{1b}$;

$R^{1a}$ is selected from —H, —$(C_1\text{-}C_4)$ alkyl and $CH_2OR^{1c}$;

$R^{1b}$ is —H; or alternatively, $R^{1a}$ and $R^{1b}$, together with the atom to which they are attached, form a 5-membered heterocyclic ring; and $R^{1c}$ is H or —$CH_3$.

In one embodiment, disclosed is a compound of formula (Ib). In another embodiment, disclosed is a pharmaceutically acceptable salt of the compound of formula (Ib).

In some embodiments of formula (Ib), $R^1$ is —H.

In some embodiments of formula (Ib), $R^1$ is —$C(O)CH(R^{1a})NHR^{1b}$; $R^{1a}$ is —H; and $R^{1b}$ is —H.

In some embodiments of formula (Ib), $R^1$ is —$C(O)CH(R^{1a})NHR^{1b}$; $R^{1a}$ is —$(C_1\text{-}C_6)$ alkyl; and $R^{1b}$ is —H.

In some embodiments of formula (Ib), $R^1$ is —$C(O)CH(R^{1a})NHR^{1b}$; $R^{1a}$ is $CH_2OR^{1c}$; and $R^{1b}$ is —H.

In some embodiments of formula (Ib), $R^1$ is —$C(O)CH(R^{1a})NHR^{1b}$; and $R^{1a}$ and $R^{1b}$, together with the atom to which they are attached, form a 5-membered heterocyclic ring.

In any of the preceding embodiments of formula (Ib), the compound is represented by any of the following structural formula:

(Ib1)

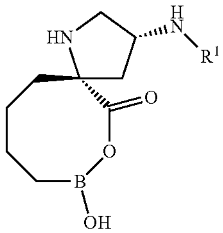

or (Ib2)

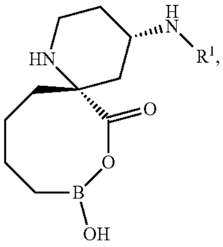

wherein $R^1$ is the same as defined above in formula (Ib).

In one embodiment, disclosed is a compound of formula (IIb), ora pharmaceutically acceptable salt thereof:

(IIb)

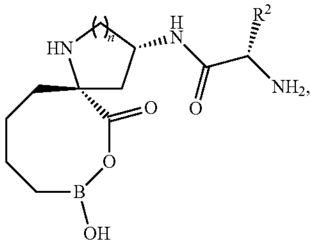

wherein n is zero or 1; and $R^2$ is selected from —H or —$(C_1-C_4)$ alkyl.

In one embodiment, disclosed is a compound of formula (IIb). In another embodiment, disclosed is a pharmaceutically acceptable salt of the compound of formula (IIb).

In some embodiments of formula (IIb), $R^2$ is —H.

In some embodiments of formula (IIb), $R^2$ is —$(C_1-C_4)$ alkyl.

In some embodiments of formula (IIb), the compound is represented by one of the following structural formula:

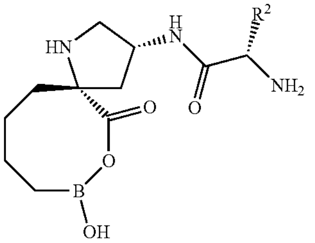

or

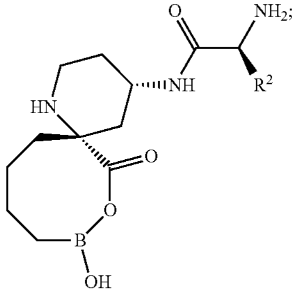

wherein $R^2$ is the same as defined above in formula (IIb).

In some embodiments, the compounds of formula (Ia), (Ia1), (Ia2), (IIa), (IIa1), and (IIa2) including any subgenera and species thereof are converted to the compounds of formula (Ib), (Ib1), (Ib2), (IIb), (IIb1), and (IIb2) including any subgenera and species thereof via intramolecular cyclization, and vice versa. That is, it is an interconversion process. The compounds of formula (Ia), (Ia1), (Ia2), (IIa), (IIa1), and (IIa2) including subgenera and species thereof and the compounds of formula (Ib), (Ib1), (Ib2), (IIb), (IIb1), and (IIb2) including subgenera and species thereof are each converted into the other partially or completely depending on the conditions, such as temperature, pressure, humidity, the pH and/or composition of medium (e.g., solvents), and etc. It is illustrated in the schemes below:

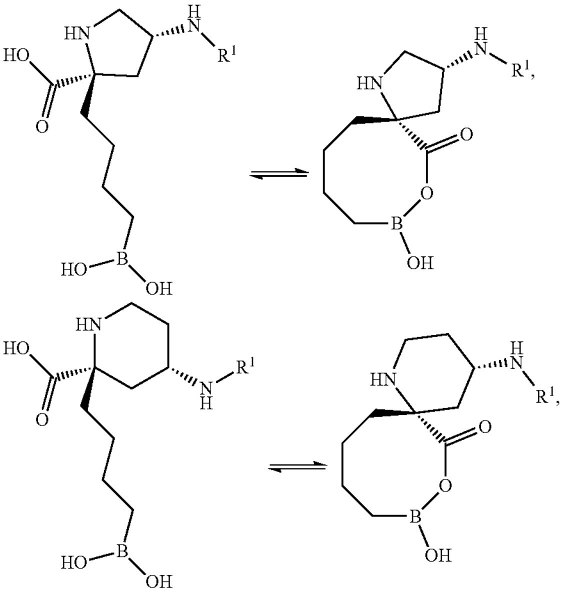

wherein $R^1$ is the same as defined in formula (Ia) and (Ib) above.

In some embodiments, disclosed are compounds of Table 1, or a pharmaceutically acceptable salt thereof:

TABLE 1

| Number | Compound | Name |
| --- | --- | --- |
| 1 | 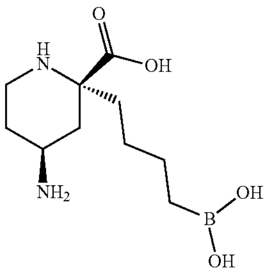 [SMILES: N[C@H]1CCN[C@@](CCCCB(O)O)(C(=O)O)C1] | (2R,4S)-4-amino-2-(4-boronobutyl)piperidine-2-carboxylic acid |

TABLE 1-continued

| Number | Compound | Name |
|---|---|---|
| 2 | 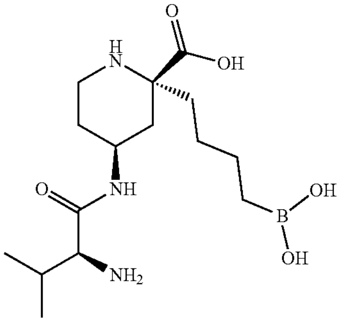 [SMILES: CC(C)[C@H](N)C(=O)N[C@H]1CCN[C@@](CCCCB(O)O)(C(=O)O)C1] | (2R,4S)-4-((S)-2-amino-3-methylbutanamido)-2-(4-boronobutyl)piperidine-2-carboxylic acid |
| 3 | 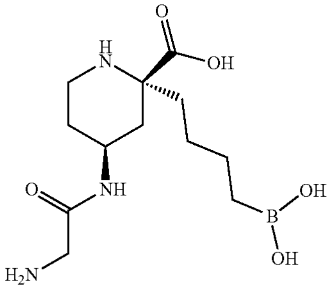 [SMILES: NCC(=O)N[C@H]1CCN[C@@](CCCCB(O)O)(C(=O)O)C1] | (2R,4S)-4-(2-aminoacetamido)-2-(4-boronobutyl)piperidine-2-carboxylic acid |
| 4 | 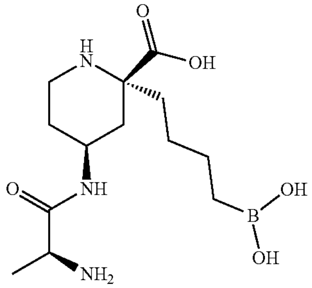 [SMILES: C[C@H](N)C(=O)N[C@H]1CCN[C@@](CCCCB(O)O)(C(=O)O)C1] | (2R,4S)-4-[[((2S)-2-aminopropanoyl]amino]-2-(4-boronobutyl)piperidine-2-carboxylic acid |
| 5 | 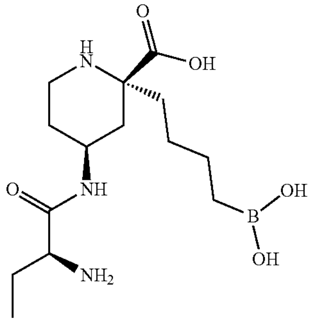 [SMILES: CC[C@H](N)C(=O)N[C@H]1CCN[C@@](CCCCB(O)O)(C(=O)O)C1] | (2R,4S)-4-[[((2S)-2-aminobutanoyl]amino]-2-(4-boronobutyl)piperidine-2-carboxylic acid |
| 6 | 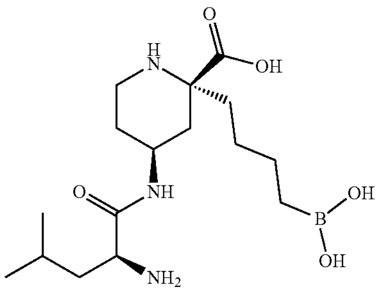 [SMILES: CC(C)C[C@H](N)C(=O)N[C@H]1CCN[C@@](CCCCB(O)O)(C(=O)O)C1] | (2R,4S)-4-[[(2S)-2-amino-4-methyl-pentanoyl]amino]-2-(4-boronobutyl)piperidine-2-carboxylic acid |

TABLE 1-continued

| Number | Compound | Name |
| --- | --- | --- |
| 7 | 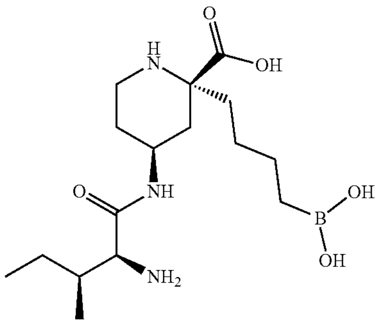 [SMILES: CC[C@H](C)[C@H](N)C(=O)N[C@H]1CCN[C@@](CCCCB(O)O)(C(=O)O)C1] | (2R,4S)-4-[[(2S,3S)-2-amino-3-methyl-pentanoyl]amino]-2-(4-boronobutyl)piperidine-2-carboxylic acid |
| 8 | 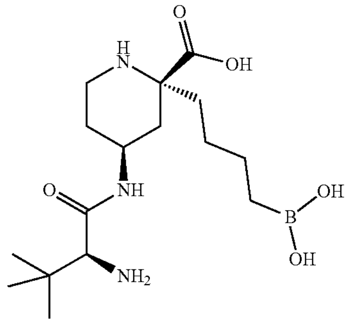 [SMILES: CC(C)(C)[C@H](N)C(=O)N[C@H]1CCN[C@@](CCCCB(O)O)(C(=O)O)C1] | (2R,4S)-4[[(2S)-2-amino-3,3-dimethyl-butanoyl]amino]-2-(4-boronobutyl)piperidine-2-carboxylic acid |
| 9 | 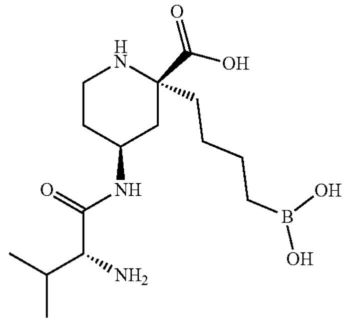 [SMILES: CC(C)[C@@H](N)C(=O)N[C@H]1CCN[C@@](CCCCB(O)O)(C(=O)O)C1] | (2R,4S)-4-[[(2R)-2-amino-3-methyl-butanoyl]amino]-2-(4-boronobutyl)piperidine-2-carboxylic acid |
| 10 | 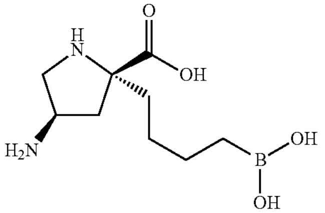 [SMILES: N[C@H]1CN[C@@](CCCCB(O)O)(C(=O)O)C1] | (2R,4R)-4-amino-2-(4-boronobutyl)pyrrolidine-2-carboxylic acid |
| 11 | 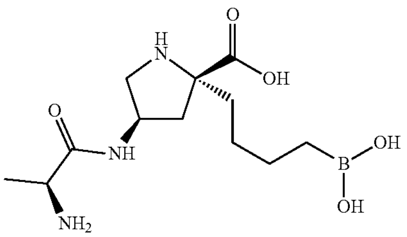 [SMILES: C[C@H](N)C(=O)N[C@H]1CN[C@@](CCCCB(O)O)(C(=O)O)C1] | (2R,4R)-4-((S)-2-aminopropanamido)-2-(4-boronobutyl)pyrrolidine-2-carboxylic acid |

TABLE 1-continued

| Number | Compound | Name |
|---|---|---|
| 12 | 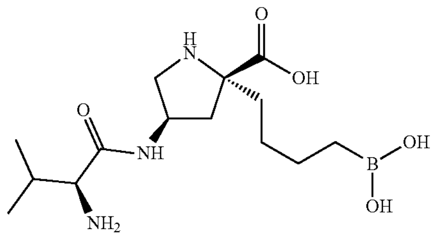 [SMILES: CC(C)[C@H](N)C(=O)N[C@H]1CN[C@@](CCCCB(O)O)(C(=O)O)C1] | (2R,4R)-4-((S)-2-amino-3-methylbutanamido)-2-(4-boronobutyl)pyrrolidine-2-carboxylic acid |
| 13 | 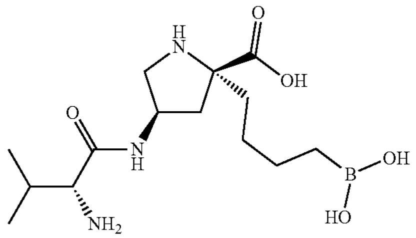 [SMILES: CC(C)[C@@H](N)C(=O)N[C@H]1CN[C@@](CCCCB(O)O)(C(=O)O)C1] | (2R,4R)-4-((R)-2-amino-3-methylbutanamido)-2-(4-boronobutyl)pyrrolidine-2-carboxylic acid |
| 14 | 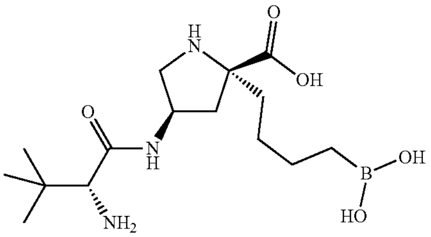 [SMILES: CC(C)(C)[C@@H](N)C(=O)N[C@H]1CN[C@@](CCCCB(O)O)(C(=O)O)C1] | (2R,4R)-4-((S)-2-amino-3,3-dimethylbutanamido)-2-(4-boronobutyl)pyrrolidine-2-carboxylic acid |
| 15 | 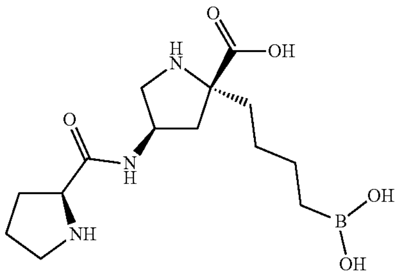 [SMILES: O=C(N[C@H]1CN[C@@](CCCCB(O)O)(C(=O)O)C1)[C@@H]1CCCN1] | (2R,4R)-2-(4-boronobutyl)-4-((S)-pyrrolidine-2-carboxamido)pyrrolidine-2-carboxylic acid |
| 16 | 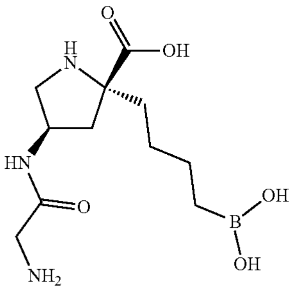 [SMILES: NCC(=O)N[C@H]1CN[C@@](CCCCB(O)O)(C(=O)O)C1] | (2R,4R)-4-(2-aminoacetamido)-2-(4-boronobutyl)pyrrolidine-2-carboxylic acid |
| 17 | 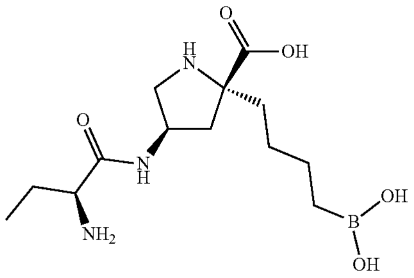 [SMILES: CC[C@H](N)C(=O)N[C@H]1CN[C@@](CCCCB(O)O)(C(=O)O)C1] | (2R,4R)-4-((S)-2-aminobutanamido)-2-(4-boronobutyl)pyrrolidine-2-carboxylic acid |

TABLE 1-continued

| Number | Compound | Name |
|---|---|---|
| 18 | 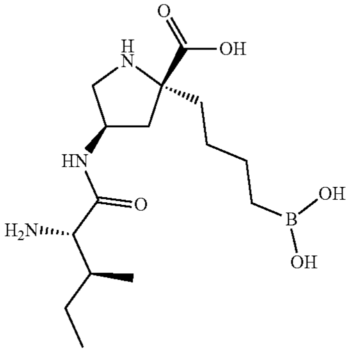 [SMILES: CC[C@H](C)[C@H](N)C(=O)N[C@H]1CN[C@@](CCCCB(O)O)(C(=O)O)C1] | (2R,4R)-4-((2S,3S)-2-amino-3-methylpentanamido)-2-(4-boronobutyl)pyrrolidine-2-carboxylic acid |
| 19 | 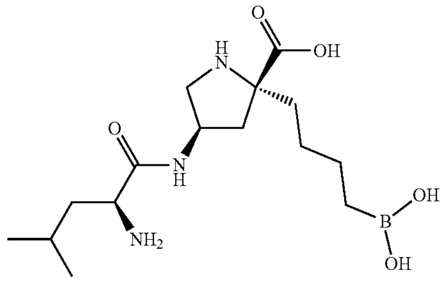 [SMILES: CC(C)C[C@H](N)C(=O)N[C@H]1CN[C@@](CCCCB(O)O)(C(=O)O)C1] | (2R,4R)-4-[[(2S)-2-amino-4-methyl-pentanoyl]amino]-2-(4-boronobutyl)pyrrolidine-2-carboxylic acid |
| 20 | 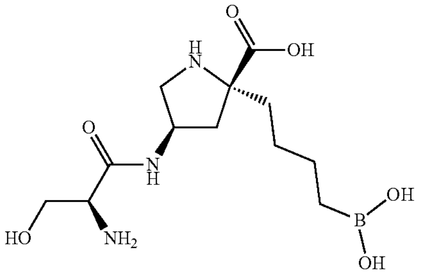 [SMILES: N[C@@H](CO)C(=O)N[C@H]1CN[C@@](CCCCB(O)O)(C(=O)O)C1] | (2R,4R)-4-[[(2S)-2-amino-3-hydroxy-propanoyl]amino]-2-(4-boronobutyl)pyrrolidine-2-carboxylic acid |
| 21 | 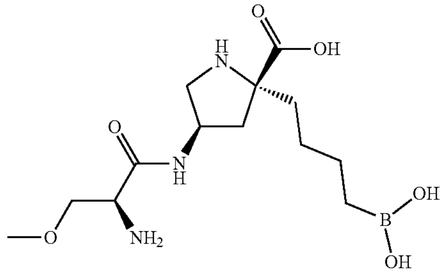 [SMILES: COC[C@H](N)C(=O)N[C@H]1CN[C@@](CCCCB(O)O)(C(=O)O)C1] | (2R,4R)-4-[[(2S)-2-amino-3-methoxy-propanoyl]amino]-2-(4-boronobutyl)pyrrolidine-2-carboxylic acid |
| 22 | 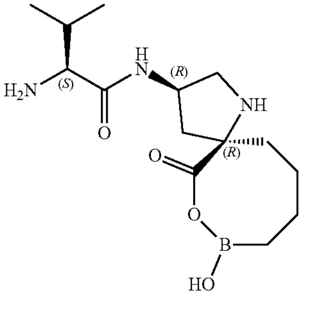 | (S)-2-amino-N-((3R,5R)-8-hydroxy-6-oxo-7-oxa-1-aza-8-boraspiro[4.7]dodecan-3-yl)-3-methylbutanamide |

TABLE 1-continued

| Number | Compound | Name |
| --- | --- | --- |
| 23 | 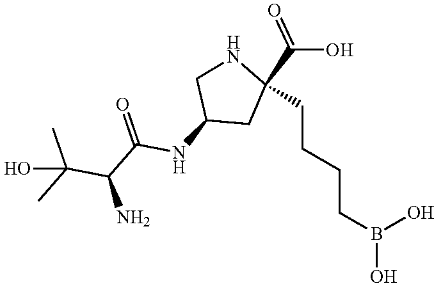 [SMILES: CC(C)(O)[C@H](N)C(=O)N[C@H]1CN[C@@](CCCCB(O)O)(C(=O)O)C1] | (2R,4R)-4-[[(2S)-2-amino-3-hydroxy-3-methyl-butanoyl]amino]-2-(4-boronobutyl)pyrrolidine-2-carboxylic acid |
| 24 | 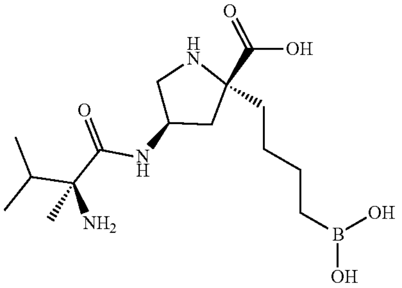 [SMILES: CC(C)[C@](C)(N)C(=O)N[C@H]1CN[C@@](CCCCB(O)O)(C(=O)O)C1] | (2R,4R)-4-[[(2S)-2-amino-2,3-dimethyl-butanoyl]amino]-2-(4-boronobutyl)pyrrolidine-2-carboxylic acid |
| 25 | 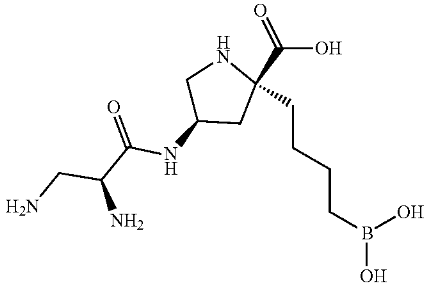 [SMILES: NC[C@H](N)C(=O)N[C@H]1CN[C@@](CCCCB(O)O)(C(=O)O)C1] | (2R,4R)-2-(4-boronobutyl)-4-((2S)-2,3-diaminopropanoyl]amino]pyrrolidine-2-carboxylic acid |
| 26 | 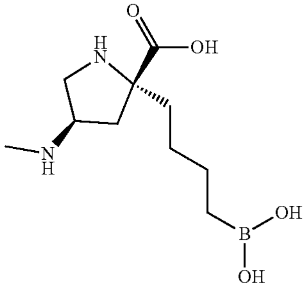 [SMILES: CN[C@H]1CN[C@@](CCCCB(O)O)(C(=O)O)C1] | (2R,4R)-2-(4-boronobutyl)-4-(methylamino)pyrrolidine-2-carboxylic acid |
| 27 | 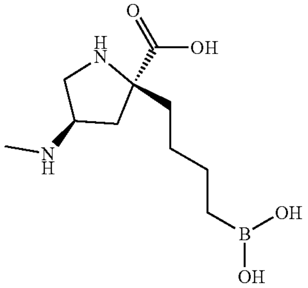 [SMILES: CN[C@H]1CN[C@](CCCCB(O)O)(C(=O)O)C1] | (2S,4R)-2-(4-boronobutyl)-4-(methylamino)pyrrolidine-2-carboxylic acid |

TABLE 1-continued

| Number | Compound | Name |
|---|---|---|
| 28 | 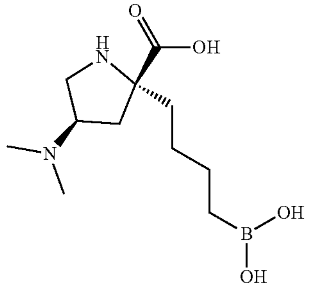 [SMILES: CN(C)[C@H]1CN[C@@](CCCCB(O)O)(C(=O)O)C1] | (2R,4R)-2-(4-boronobutyl)-4-(dimethylamino)pyrrolidine-2-carboxylic acid |
| 29 | 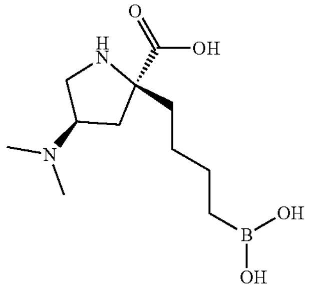 [SMILES: CN(C)[C@H]1CN[C@](CCCCB(O)O)(C(=O)O)C1] | (2S,4R)-2-(4-boronobutyl)-4-(dimethylamino)pyrrolidine-2-carboxylic acid |
| 30 | 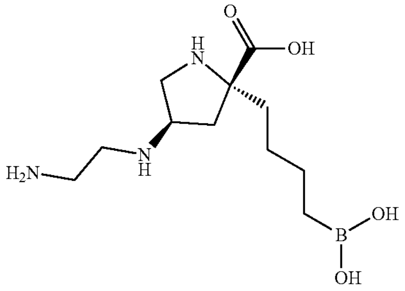 [SMILES: NCCN[C@H]1CN[C@@](CCCCB(O)O)(C(=O)O)C1] | (2R,4R)-4-(2-aminoethylamino)-2-(4-boronobutyl)pyrrolidine-2-carboxylic acid |
| 31 | 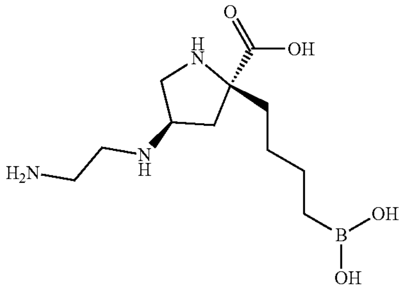 [SMILES: NCCN[C@H]1CN[C@](CCCCB(O)O)(C(=O)O)C1] | (2S,4R)-4-(2-aminoethylamino)-2-(4-boronobutyl)pyrrolidine-2-carboxylic acid |
| 32 | 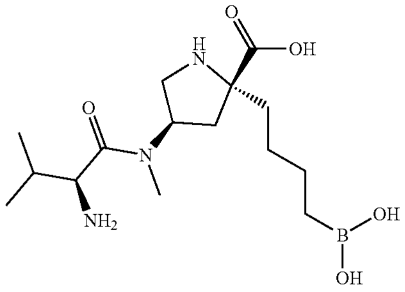 [SMILES: CC(C)[C@H](N)C(=O)N(C)[C@H]1CN[C@@](CCCCB(O)O)(C(=O)O)C1] | (2R,4R)-4-[[(2S)-2-amino-3-methyl-butanoyl]-methyl-amino]-2-(4-boronobutyl)pyrrolidine-2-carboxylic acid |

TABLE 1-continued

| Number | Compound | Name |
| --- | --- | --- |
| 33 | 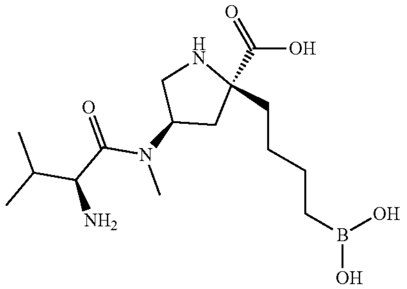 [SMILES: CC(C)[C@H](N)C(=O)N(C)[C@H]1CN[C@](CCCCB(O)O)(C(=O)O)C1] | (2S,4R)-4-[[(2S)-2-amino-3-methyl-butanoyl]-methyl-amino]-2-(4-boronobutyl)pyrrolidine-2-carboxylic acid |

The language "$C_1$-$C_4$ alkyl" includes acyclic alkyl moieties having 1 to 4 carbon atoms, and "$C_1$-$C_6$ alkyl" includes acyclic alkyl moieties having 1 to 6 carbon atoms. Examples of $C_1$-$C_4$ alkyl moieties include methyl, ethyl, n-propyl, isopropyl, n-butyl, sec-butyl, isobutyl, and tert-butyl.

The language "pharmaceutically acceptable salt" includes acid addition or base addition salts that retain the biological effectiveness and properties of the compounds of formula (Ia), (Ia1), (Ia2), (IIa), (IIa1), (IIa2), (Ib), (Ib1), (Ib2), (IIb), (IIb1), and (IIb2) including any subgenera or species thereof, and Table 1 and, which typically are not biologically or otherwise undesirable. In many cases, the compounds of formula (Ia), (Ia1), (Ia2), (IIa), (IIa1), (IIa2), (Ib), (Ib1), (Ib2), (IIb), (IIb1), and (IIb2) including any subgenera or species thereof, and Table 1 are capable of forming acid and/or base salts by virtue of the presence of basic and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethanedisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulfate, naphthoate, napsylate, nicotinate, nitrate, octadecanoate, oleate, oxalate, palmitate, palmoate, phosphate/hydrogen phosphate/dihydrogen phosphate, polygalacturonate, propionate, stearate, succinate, subsalicylate, sulfate/hydrogensulfate, tartrate, tosylate and trifluoroacetate salts. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, masonic acid, succinic acid, fumaric acid, tartaric acid, citric acid, benzoic acid, mandelic acid, methanesulfonic acid, ethanesulfonic acid, toluenesulfonic acid, trifluoroacetic acid, sulfosalicylic acid, and the like.

Pharmaceutically acceptable base addition salts can be formed with inorganic and organic bases. Inorganic bases from which salts can be derived include, for example, ammonia and salts of ammonium and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the compounds of formula (Ia), (Ia1), (Ia2), (IIa), (IIa1), (IIa2), (Ib), (Ib1), (Ib2), (IIb), (IIb1), and (IIb2) including any subgenera or species thereof, and Table 1 can be synthesized from a basic or acidic moiety, by conventional chemical methods. Generally, such salts can be prepared by reacting free acid forms of these compounds with a stoichiometric amount of the appropriate base (such as $Na^+$, $Ca^{2+}$, $Mg^{2+}$, or $K^+$ hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences," 20th ed., Mack Publishing Company, Easton, Pa., (1985); Berge et al., "*J. Pharm. Sci.,* 1977, 66, 1-19 and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms for the compounds of formula (Ia), (Ia1), (Ia2), (IIa), (IIa1), (IIa2), (Ib), (Ib1), (Ib2), (IIb), (IIb1), and (IIb2) including any subgenera or species thereof, and Table 1. Isotopically labeled compounds have structures depicted by the formulas given herein except that one or more atoms are replaced by an atom of the same element but with differing mass number. Examples of isotopes that can be incorporated into the compounds of formula (Ia), (Ia1), (Ia2), (IIa), (IIa1), (IIa2), (Ib), (Ib1), (Ib2), (IIb), (IIb1), and (IIb2) including any subgenera or species thereof, and Table 1 and their pharmaceutically acceptable salts include isotopes of hydrogen, carbon, nitrogen, oxygen, phosphorous, sulfur, fluorine, chlorine and iodine, such as $^2H$, $^3H$, $^{11}C$, $^{13}C$, $^{14}C$, $^{15}N$, $^{35}S$, $^{36}Cl$ and $^{125}I$. Isotopically labeled compounds of formula (Ia), (Ia1), (Ia2), (IIa), (IIa1), (IIa2), (Ib), (Ib1), (Ib2), (IIb), (IIb1), and (IIb2) including any subgenera or species thereof, and Table 1 can generally be prepared by conventional techniques known to those skilled in the art or by processes analogous to those described in the accompanying Examples using appropriate isotopically labeled reagents in place of the non-labeled reagents previously employed.

The compounds of formula (Ia), (Ia1), (Ia2), (IIa), (IIa1), (IIa2), (Ib), (Ib1), (Ib2), (IIb), (IIb1), and (IIb2) including any subgenera or species thereof, and Table 1 may have different isomeric forms. The language "optical isomer," "stereoisomer" or "diastereoisomer" refers to any of the various stereoisomeric configurations which may exist for a given compound of formula (Ia), (Ia1), (Ia2), (IIa), (IIa1), (IIa2), (Ib), (Ib1), (Ib2), (IIb), (IIb1), and (IIb2) including any subgenera or species thereof, and Table 1. It is understood that a substituent may be attached at a chiral center of a carbon atom and, therefore, the disclosed compounds include enantiomers, diastereomers and racemates. The term "enantiomer" includes pairs of stereoisomers that are non-superimposable mirror images of each other. A 1:1 mixture of a pair of enantiomers is a racemic mixture. The term is used to designate a racemic mixture where appropriate. The terms "diastereomers" or "diastereoisomers" include stereoisomers that have at least two asymmetric atoms, but which are not mirror images of each other. The absolute stereochemistry is specified according to the Cahn-Ingold-Prelog R-S system. When a compound is a pure enantiomer, the stereochemistry at each chiral center may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds of formula (Ia), (Ia1), (Ia2), (IIa), (IIa1), (IIa2), (Ib), (Ib1), (Ib2), (IIb), (IIb1), and (IIb2) including any subgenera or species thereof, and Table 1 contain one or more asymmetric centers or axes and may thus give rise to enantiomers, diastereomers or other stereoisomeric forms that may be defined, in terms of absolute stereochemistry, as (R)- or (S)-. The present disclosure is meant to include all such possible isomers, including racemic mixtures, optically pure forms and intermediate mixtures. Optically active (R)- and (S)-isomers may be prepared using chiral synthons or chiral reagents, or resolved using conventional techniques well known in the art, such as chiral HPLC.

Immunomodulatory Agents

As used herein, "immunomodulatory agent" refers to an agent that enhances an immune response (e.g., antitumor immune response). An immunomodulatory agent can be an antibody or antigen-binding fragment thereof, a protein, a peptide, a DNA or RNA fragment, a small molecule, or combination thereof. In some embodiments, the immunomodulatory agent is an immune checkpoint inhibitor. In some embodiments, the immunomodulatory agent is an immunostimulant. As used herein, an "immune checkpoint inhibitor" means an agent that inhibits proteins or peptides (i.e., immune checkpoint agents) which are blocking the immune system, e.g., from attacking cancer cells. In some embodiments, the immune checkpoint agent blocking the immune system prevents the production and/or activation of T cells. In some embodiments, the immune checkpoint inhibitor is cytotoxic T lymphocyte associated protein 4 (CTLA-4), programmed cell death protein 1 (PD1), or programmed death ligand 1 (PD-L1). PD-L1 and PD1 form a cell surface-bound ligand-receptor pair that, in healthy individuals, dampen the immune response to prevent an over-reaction of the immune system. In some embodiments, cancer cells hijack the normal PD-L1/ PD1 immune checkpoint mechanism by overexpressing the ligand PD-L1, which binds to PD1 on effector CD8 T cells, thereby preventing the T cells from mounting an immune response to the cancer cell and/or tumor. PD-L1 is expressed in a broad range of cancers with high frequently. Tumor PD-L1 overexpression correlates with poor prognosis in a number of cancers (see, e.g., Hamid et al., Expert Opin Biol Ther 13(6):847-861, 2013). As used herein, an "immunostimulant" means a substance that stimulate the immune system by inducing activation or increasing activity of any of its components without any antigenic specificity in immune response. In some embodiments, the immunostimulant is a toll-like receptor 3 (TLR3) agonist, such as polyinosinic: polycytidylic acid which is also known as poly I:C or poly(I:C).

A review describing immune checkpoint pathways and the blockade of such pathways with immune checkpoint inhibitor compounds is provided by Pardoll in *Nature Reviews Cancer* (April, 2012), pages 252-264. Immune check point inhibitor compounds display anti-tumor activity by blocking one or more of the endogenous immune checkpoint pathways that downregulate an anti-tumor immune response. The inhibition or blockade of an immune checkpoint pathway typically involves inhibiting a checkpoint receptor and ligand interaction with an immune checkpoint inhibitor compound to reduce or eliminate the signal and resulting diminishment of the anti-tumor response.

As used herein, an "immune checkpoint inhibitor" means an agent that inhibits proteins or peptides (i.e., immune checkpoint agents) which are blocking the immune system, e.g., from attacking cancer cells. An immune checkpoint inhibitor can be an antibody or antigen-binding fragment thereof, a protein, a peptide, a small molecule, or combination thereof. In some embodiments, the immune checkpoint agent blocking the immune system prevents the production and/or activation of T cells. In some embodiments, the immune checkpoint agent is cytotoxic T lymphocyte associated protein 4 (CTLA-4), programmed cell death protein 1 (PD1), programmed death ligand 1 (PD-L1), or an inhibitory receptor that recognizes HLA-E and is expressed by NK cells and a subset of T cells (such as NKG2A). PD-L1 and PD1 form a cell surface-bound ligand-receptor pair that, in healthy individuals, dampen the immune response to prevent an over-reaction of the immune system. In some embodiments, cancer cells hijack the normal PD-L1/ PD1 immune checkpoint mechanism by overexpressing the ligand PD-L1, which binds to PD1 on effector CD8 T cells, thereby preventing the T cells from mounting an immune response to the cancer cell and/or tumor. PD-L1 is expressed in a broad range of cancers with high frequency. Tumor PD-L1 overexpression correlates with poor prognosis in a number of cancers (see, e.g., Hamid et al., Expert Opin Biol Ther 13(6):847-861, 2013).

In some embodiments of the present disclosure, the immune checkpoint inhibitor compound inhibits the signaling interaction between an immune checkpoint receptor and the corresponding ligand of the immune checkpoint receptor. The immune checkpoint inhibitor compound can act by blocking activation of the immune checkpoint pathway by inhibition (antagonism) of an immune checkpoint receptor (some examples of receptors include CTLA-4, PD-1, and NKG2A) or by inhibition of a ligand of an immune checkpoint receptor (some examples of ligands include PD-L1 and PD-L2). In such embodiments, the effect of the immune checkpoint inhibitor compound is to reduce or eliminate down regulation of certain aspects of the immune system anti-tumor response in the tumor microenvironment.

In some embodiments, the immune checkpoint inhibitor inhibits the CTLA-4 pathway or the PD-L1/ PD1 pathway. In some embodiments, the immune checkpoint inhibitor is an antibody. In some embodiments, the immune checkpoint inhibitor comprises an antibody that inhibits CTLA-4, PD1, or PD-L1. Immune checkpoint inhibitors, immune checkpoint inhibitors and examples thereof are provided in, e.g., WO 2016/062722.

In some embodiments, the immune checkpoint inhibitor is an anti-CTLA-4 antibody or derivative or antigen-binding fragment thereof. In embodiments, the anti-CTLA-4 antibody selectively binds a CTLA-4 protein or fragment thereof. Examples of anti-CTLA-4 antibodies and derivatives and fragments thereof are described in, e.g., U.S. Pat. Nos. 6,682,736; 7,109,003; 7,123,281; 7,411,057; 7,807,797; 7,824,679; 8,143,379; 8,491,895, and US 2007/0243184. In some embodiments, the anti-CTLA-4 antibody is tremelimumab or ipilimumab.

The immune checkpoint receptor cytotoxic T-lymphocyte associated antigen 4 (CTLA-4) is expressed on T-cells and is involved in signaling pathways that reduce the level of T-cell activation. It is believed that CTLA-4 can downregulate T-cell activation through competitive binding and sequestration of CD80 and CD86. In addition, CTLA-4 has been shown to be involved in enhancing the immunosuppressive activity of $T_{Reg}$ cells.

In some embodiments, the immune checkpoint inhibitor is an anti-PD-L1 antibody or derivative or antigen-binding fragment thereof. In some embodiments, the anti-PD-L1 antibody or derivative or antigen-binding fragment thereof selectively binds a PD-L1 protein or fragment thereof. Examples of anti-PD-L1 antibodies and derivatives and fragments thereof are described in, e.g., WO 01/14556, WO 2007/005874, WO 2009/089149, WO 2011/066389, WO 2012/145493; U.S. Pat. Nos. 8,217,149, 8,779,108; U.S. 2012/0039906, U.S. 2013/0034559, U.S. 2014/0044738, and U.S. 2014/0356353. In some embodiments, the anti-PD-L1 antibody is MEDI4736 (durvalumab), MDPL3280A, 2.7A4, AMP-814, MDX-1105, atezolizumab (MPDL3280A), or BMS-936559.

The immune checkpoint receptor programmed death 1 (PD-1) is expressed by activated T-cells upon extended exposure to antigen. Engagement of PD-1 with its known binding ligands, PD-L1 and PD-L2, occurs primarily within the tumor microenvironment and results in downregulation of anti-tumor specific T-cell responses. Both PD-L1 and PD-L2 are known to be expressed on tumor cells. The expression of PD-L1 and PD-L2 on tumors has been correlated with decreased survival outcomes.

In some embodiments, the anti-PD-L1 antibody is MEDI4736, also known as durvalumab. In some embodiments, the anti-PD-L1 antibody comprises an amino acid sequence at least 80%, at least 85%, at least 90%, at least 95%, or at least 99% identical to any of SEQ ID NOs: 1-8. MEDI4736 is an anti-PD-L1 antibody that is selective for a PD-L1 polypeptide and blocks the binding of PD-L1 to the PD-1 and CD80 receptors. MEDI4736 can relieve PD-L1-mediated suppression of human T-cell activation in vitro and can further inhibit tumor growth in a xenograft model via a T-cell dependent mechanism. MEDI4736 is further described in, e.g., U.S. Pat. No. 8,779,108. The fragment crystallizable (Fc) domain of MEDI4736 contains a triple mutation in the constant domain of the IgG1 heavy chain that reduces binding to the complement component C1q and the Fcγ receptors responsible for mediating antibody-dependent cell-mediated cytotoxicity (ADCC).

In some embodiments, MEDI4736 or an antigen-binding fragments thereof comprises a heavy chain and a light chain or a heavy chain variable region and a light chain variable region. In some embodiments, MEDI4736 or an antigen-binding fragment thereof for use comprises a light chain variable region comprising the amino acid sequence of SEQ ID NO: 1 and a heavy chain variable region comprising the amino acid sequence of SEQ ID NO: 2. In some embodiments, MEDI4736 or an antigen-binding fragment thereof comprises a heavy chain variable region and a light chain variable region, wherein the heavy chain variable region comprises the Kabat-defined CDR1, CDR2, and CDR3 sequences of SEQ ID NOS: 3-5, and wherein the light chain variable region comprises the Kabat-defined CDR1, CDR2, and CDR3 sequences of SEQ ID NOS: 6-8. A person of ordinary skill in the art would easily be able to identify Chothia-defined, Abm-defined or other CDR definitions known to those of ordinary skill in the art. In some embodiments, MEDI4736 or an antigen-binding fragment thereof comprises the variable heavy chain and variable light chain CDR sequences of the 2.14H90PT antibody as described in WO 2011/066389.

In some embodiments, the immune checkpoint inhibitor is an anti-PD-1 antibody or derivative or antigen-binding fragment thereof. In some embodiments, the anti-PD-1 antibody selectively binds a PD-1 protein or fragment thereof. In some embodiments, the anti-PD1 antibody is nivolumab, pembrolizumab, or pidilizumab.

NKG2A receptors are inhibitory receptors binding to HLA-E and expressed on tumor infiltrating cytotoxic NK and CD8 T lymphocytes. By expressing HLA-E, cancer cells can protect themselves from killing by NKG2A+ immune cells. HLA-E is frequently up-regulated on cancer cells of many solid tumors or hematological malignancies. Monalizumab (IPH2201), a humanized IgG4, blocks the binding of NKG2A to HLA-E allowing activation of NK and cytotoxic T cell responses. Examples of anti-NKG2A antibodies and derivatives and fragments thereof are described in WO 2016/041947, the content of which is hereby incorporated by reference in its entirety including, but not limited to, the sequence listings.

In some embodiments of the present disclosure, the immune checkpoint inhibitor compound is a small organic molecule (molecular weight less than 1000 daltons), a peptide, a polypeptide, a protein, an antibody, an antibody fragment, or an antibody derivative. In some embodiments, the immune checkpoint inhibitor compound is an antibody. In some embodiments, the antibody is a monoclonal antibody, specifically a human or a humanized monoclonal antibody.

Monoclonal antibodies, antibody fragments, and antibody derivatives for blocking immune checkpoint pathways can be prepared by any of several methods known to those of ordinary skill in the art, including but not limited to, somatic cell hybridization techniques and hybridoma, methods. Hybridoma generation is described in *Antibodies, A Laboratory Manual, Harlow and Lane,* 1988, Cold Spring Harbor Publications, New York. Human monoclonal antibodies can be identified and isolated by screening phage display libraries of human immunoglobulin genes by methods described for example in U.S. Pat. Nos. 5,223,409, 5,403,484, 5,571,698, 6,582,915, and 6,593,081. Monoclonal antibodies can be prepared using the general methods described in U.S. Pat. No. 6,331,415 (Cabilly).

As an example, human monoclonal antibodies can be prepared using a XenoMouse™ (Abgenix, Freemont, CA) or hybridomas of B cells from a XenoMouse. A XenoMouse is a murine host having functional human immunoglobulin genes as described in U.S. Pat. No. 6,162,963 (Kucherlapati).

Methods for the preparation and use of immune checkpoint antibodies are described in the following illustrative publications. The preparation and therapeutic uses of anti- CTLA-4 antibodies are described in U.S. Pat. No. 7,229,628 (Allison), U.S. Pat. No. 7,311,910 (Linsley), and U.S. Pat. No. 8,017,144 (Korman). The preparation and therapeutic uses of anti-PD-1 antibodies are described in U.S. Pat. No. 8,008,449 (Korman) and U.S. Patent Application No. 2011/0271358 (Freeman). The preparation and therapeutic uses of anti-PD-L1 antibodies are described in U.S. Pat. No. 7,943,743 (Korman). The preparation and therapeutic uses of anti-TIM-3 antibodies are described in U.S. Pat. Nos. 8,101,176 (Kuchroo) and 8,552,156 (Tagayanagi). The preparation and therapeutic uses of anti-LAG-3 antibodies are described in U.S. Patent Application No. 2011/0150892 (Thudium) and International Publication Number WO2014/008218 (Lonberg). The preparation and therapeutic uses of anti-KIR antibodies are described in U.S. Pat. No. 8,119,775 (Moretta). The preparation of antibodies that block BTLA regulated inhibitory pathways (anti-BTLA antibodies) are described in U.S. Pat. No. 8,563,694 (Mataraza).

In some embodiments of the present disclosure, the immune checkpoint inhibitor compound is a CTLA-4 receptor inhibitor, a PD-1 receptor inhibitor, a LAG-3 receptor inhibitor, a TIM-3 receptor inhibitor, a BTLA receptor inhibitor, or a KIR receptor inhibitor. In some embodiments, the immune checkpoint inhibitor compound is an inhibitor of PD-L1 or an inhibitor of PD-L2.

In some embodiments of the present disclosure, the immune checkpoint inhibitor compound is an inhibitor of the PD-L1/ PD-1 pathway or the PD-L2/ PD-1 pathway. In some embodiments, the inhibitor of the PD-L1/ PD-1 pathway is MEDI4736.

In some embodiments of the present disclosure, the immune checkpoint inhibitor compound is an anti-CTLA-4 receptor antibody, an anti-PD-1 receptor antibody, an anti-LAG-3 receptor antibody, an anti-TIM-3 receptor antibody, an anti-BTLA receptor antibody, an anti-KIR receptor antibody, an anti-PD-L1 antibody, or an anti-PD-L2 antibody.

In some embodiments of the present disclosure, the anti-CTLA-4 receptor antibody is ipilimumab or tremelimumab. In some embodiments the anti-PD-1 receptor antibody is lambrolizumab, pidilizumab, or nivolumab. In some embodiments, the anti-KIR receptor antibody is lirilumab.

Radiation Therapy

Radiation therapy, also known as high-dose ionizing irradiation, is used in combination with a compound of Formula (Ia) or Formula (Ib), or a pharmaceutically acceptable salt thereof, for treating cancer. In some embodiments, the present method comprises administering to a patient the radiation therapy in combination with the compound of Formula (Ia) or Formula (Ib), or a pharmaceutically acceptable salt thereof, and an immunomodulatory agent.

The radiation therapy may be x-rays, gamma rays, or charged particles. The radiation therapy may be external-beam radiation therapy or internal radiation therapy (also called brachytherapy). Systemic radiation therapy, using radioactive substances, such as radioactive iodine, may also be employed. External-beam radiation therapy includes 3D conformational radiation therapy, intensity-modulated radiation therapy, image-guided radiation therapy, tomotherapy, stereotactic radiosurgery, proton therapy, or other charged particle beams.

The radiation therapy may be x-rays, gamma rays, or charged particles. The radiation therapy may be external-beam radiation therapy or internal radiation therapy (also called brachytherapy). Systemic radiation therapy, using radioactive substances, such as radioactive iodine, may also be employed. External-beam radiation therapy includes 3D conformational radiation therapy, intensity-modulated radiation therapy, image-guided radiation therapy, tomotherapy, stereotactic radiosurgery, proton therapy, or other charged particle beams.

In some embodiments, the radiation therapy is fractionated radiation therapy. In one embodiment, the fractionated radiation therapy comprises from 2 to 14 fractions. In another embodiment, the fractionated radiation therapy comprises from 2 to 7 fractions. In another embodiment, the fractionated radiation therapy comprises from 3 to 6 fractions. In one embodiment, the fractionated radiation therapy comprises 2, 3, 4, 5, 6, or 7 fractions. In one embodiment, the fractionated radiation therapy comprises 5 fractions. In some embodiments, the radiation therapy fractions are administered in sequential days. In one embodiment, radiation therapy may include more than one dose on a day and/or doses on sequential days.

In one mode, the radiation therapy fractions are administered on day 1, day 2, day 3, day 4, and day 5.

Combination Therapy

The present disclosure provides methods of treating cancer in which a compound of Formula (Ia) or (Ib) including any subgenus or species thereof, or a pharmaceutically acceptable salt thereof, and an immunomodulatory agent are administered in a combined fashion. In another aspect, the present disclosure provides methods of treating cancer in which a compound of Formula (Ia) or (Ib) including any subgenus or species thereof, or a pharmaceutically acceptable salt thereof, and a radiation therapy optionally with an immunomodulatory agent are administered in a combined fashion.

In some embodiments, the compound of Formula (Ia) or (Ib) or a pharmaceutically acceptable salt thereof and the immunomodulatory agent are administered separately, sequentially or simultaneously. In some embodiments, the compound of Formula (Ia) or (Ib) or a pharmaceutically acceptable salt thereof and the radiation therapy are administered on the same days or different days. In one embodiment, the radiation therapy was employed prior to the treatment of the compound of Formula (Ia) or (Ib) or a pharmaceutically acceptable salt thereof and/or the immunomodulatory agent. In another embodiment, the radiation therapy was employed after the treatment of the compound of Formula (Ia) or (Ib) or a pharmaceutically acceptable salt thereof and/or the immunomodulatory agent. In another embodiment, the radiation therapy was administered concurrently with the treatment of the compound of Formula (Ia) or (Ib) or a pharmaceutically acceptable salt thereof and/or the immunomodulatory agent.

In some embodiments, the compound of Formula (Ia) or (Ib) is selected from the compounds listed in Table 1, i.e., Compounds 1 to 33, and the immunomodulatory agent is selected from durvalumab, tremelimumab, monalizumab, or a combination thereof.

In some embodiments, administration of the combination of the compound of Formula (Ia) or (Ib) and the immunomodulatory agent results in an additive and/or synergistic effect. As used herein, the term "synergistic" refers to a combination of therapies (e.g., a combination of MEDI4736 or an antigen-binding fragment thereof, and an arginase inhibitor as described herein), which is more effective than the additive effects of the single therapies.

In some embodiments, the method provided herein, e.g., administration of a compound of Formula (Ia) or (Ib) and an immunomodulatory agent in combination advantageously enhances antigen presentation, and/or promotes T cell activation, and thereby provides a safer and more effective treatment to the patient, compared with a method that administers only one agent. In some embodiments, the method provided herein results in an increase in CD8+ T cells, NK cells, and/or CD103+ dendritic cells compared to administration of the immunomodulatory agent alone or administration of the compound of Formula (Ia) or (Ib) alone. In some embodiments, the method provided herein results in an increase in interferon-γ (IFNγ) levels in the patient compared with a method administering only one agent. In some embodiments, the method provided herein results in an increase in interleukin-2 (IL-2) levels in the patient compared with a method administering only one agent.

SEQ ID NOs: 1-8 correspond to amino acid sequences of MEDI4736, which is an anti-PD-L1 antibody as described in embodiments herein. SEQ ID NO: 3 corresponds to an amino acid sequence of the light chain variable region of MEDI4736. SEQ ID NO: 4 corresponds to an amino acid sequence of the heavy chain variable region of MEDI4736. SEQ ID NOs: 5-10 correspond to CDRs of MEDI4736.

SEQ ID NOs: 9-16 correspond to an amino acid sequence of tremelimumab, which is an anti-CTLA-4 antibody as described in embodiments herein.

SEQ ID NOs: 17-24 correspond to an amino acid sequence of monalizumab, which is an anti-NKG2A antibody as described in embodiments herein.

All references cited herein, including patents, patent applications, papers, textbooks and the like, and the references cited therein, to the extent that they are not already, are hereby incorporated herein by reference in their entirety.

EXAMPLES

Aspects of the present disclosure can be further defined by reference to the following non-limiting examples, which describe in detail preparation of certain compounds and intermediates of the present disclosure and methods for using compounds of the present disclosure. It will be apparent to those skilled in the art that many modifications, both to materials and methods, can be practiced without departing from the scope of the present disclosure.

Unless stated otherwise:

(i) all syntheses were carried out at ambient temperature, i.e. in the range 17 to 25° C. and under an atmosphere of an inert gas such as nitrogen unless otherwise stated;

(ii) evaporations were carried out by rotary evaporation or utilising Genevac equipment or Biotage v10 evaporator in vacuo and work-up procedures were carried out after removal of residual solids by filtration;

(iii) flash chromatography purifications were performed on an automated Teledyne Isco CombiFlash® Rf or Teledyne Isco CombiFlash® Companion® using prepacked RediSep Rf Gold™ Silica Columns (20-40 μm, spherical particles), GraceResolv™ Cartridges (Davisil® silica) or Silicycle cartridges (40-63 μm).

(iv) preparative chromatography was performed on a Gilson prep HPLC instrument with UV collection; alternatively, preparative chromatography was performed on a Waters AutoPurification HPLC-MS instrument with MS- and UV-triggered collection;

(v) chiral preparative chromatography was performed on a Gilson instrument with UV collection (233 injector/fraction collector, 333 & 334 pumps, 155 UV detector) or a Varian Prep Star instrument (2×SD1 pumps, 325 UV detector, 701 fraction collector) pump running with Gilson 305 injection; alternatively, chiral preparative chromatography was performed on a Waters Prep 100 SFC-MS instrument with MS- and UV-triggered collection or a Thar MultiGram III SFC instrument with UV collection.

(vi) yields, where present, are not necessarily the maximum attainable;

(vii) in general, the structures of end-products of the Formula I were confirmed by nuclear magnetic resonance (NMR) spectroscopy; NMR chemical shift values were measured on the delta scale [proton magnetic resonance spectra were determined using a Bruker Avance III 600 (600 MHz), Bruker Avance 400 (400 MHz), Bruker Avance 300 (300 MHz) or Bruker DRX 500 (500 MHz) instrument]; measurements were taken at ambient temperature unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal.

(viii) in general, end-products of the Formula I were also characterized by mass spectroscopy following liquid chromatography (LCMS or UPLC); UPLC was carried out using a Waters UPLC fitted with a Waters SQ mass spectrometer (Column temp 40° C., UV=220-300 nm or 190-400 nm, Mass Spec=ESI with positive/negative switching) at a flow rate of 1 mL/min using a solvent system of 97% A+3% B to 3% A+97% B over 1.50 min (total run time with equilibration back to starting conditions, etc., 1.70 min), where A=0.1% formic acid or 0.05% trifluoroacetic acid in water (for acidic work) or 0.1% ammonium hydroxide in water (for basic work) and B=acetonitrile. For acidic analysis the column used was a Waters Acquity HSS T3 (1.8 μm, 2.1×50 mm), for basic analysis the column used was a Waters Acquity BEH C18 (1.7 μm 2.1×50 mm). Alternatively, UPLC was carried out using a Waters UPLC fitted with a Waters SQ mass spectrometer (Column temp 30° C., UV=210-400 nm, Mass Spec=ESI with positive/negative switching) at a flow rate of 1 mL/min using a solvent gradient of 2 to 98% B over 1.5 mins (total run time with equilibration back to starting conditions 2 min), where A=0.1% formic acid in water and B=0.1% formic acid in acetonitrile (for acidic work) or A=0.1% ammonium hydroxide in water and B=acetonitrile (for basic work). For acidic analysis the column used was a Waters Acquity HSS T3 (1.8 μm, 2.1×30 mm), for basic analysis the column used was a Waters Acquity BEH C18 (1.7 μm, 2.1×30 mm); LCMS was carried out using a Waters Alliance HT (2795) fitted with a Waters ZQ ESCi mass spectrometer and a Phenomenex Gemini-NX C18 (5 μm, 110A, 2.1×50 mm column at a flow rate of 1.1 mL/min 95% A to 95% B over 4 min with a 0.5 min hold where A=0.1% formic acid and B=0.1% formic acid in acetonitrile (for acidic work) or A=0.1% ammonium hydroxide in water and B=acetonitrile (for basic work). Additionally, LCMS was carried out using a Shimadzu UFLC fitted with a Shimadzu LCMS-2020 mass spectrometer and a Waters HSS C18 (1.8 μm, 2.1×50 mm) or Shim-pack XR-ODS (2.2 μm, 3.0×50 mm) or Phenomenex Gemini-NX C18 (3 μm, 3.0×50 mm) column at a flow rate of 0.7 mL/min (for Waters HSS C18 column), 1.0 mL/min (for Shim-pack XR-ODS column) or 1.2 mL/min (for Phenomenex Gemini-NX C18), 95% A to 95% B over 2.2 min with a 0.6 min hold, where A=0.1% formic acid or 0.05% trifluoroacetic acid in water (for acidic work) or 0.1% ammonium hydroxide or 6.5 mM ammonium carbonate in water (for basic work) and B=acetonitrile. The reported molecular ion corresponds to the [M+H]+ unless otherwise specified; for molecules with multiple isotopic patterns (Br, Cl, etc.) the reported value is the one obtained for the lowest isotope mass unless otherwise specified.

(ix) ion exchange purification was generally performed using an SCX-2 (Biotage) cartridge.

(x) intermediate purity was assessed by thin layer chromatographic, mass spectroscopy, LCMS, UPLC/MS, HPLC (high performance liquid chromatography) and/or NMR analysis;

(xi) the following abbreviations have been used:

EtOH: ethanol

EtOAc: ethyl acetate

LDA: lithium diisopropylamide

MeOH: methanol

TFA: trifluoroacetic acid

MeCN: acetonitrile

LCMS: liquid chromatography—mass spectrometry rt or RT: room temperature aq: aqueous THF: tetrahydrofuran KHMDS: potassium bis(trimethylsilyl)amide DCM: dichloromethane DMF: dimethylformamide HATU: (1-[Bis(dimethylamino)methylene]-1H-1,2,3-triazolo[4,5-b]pyridinium 3-oxid hexafluorophosphate)

BOC: tert-butoxycarbonyl

DTNB: 5,5'-dithiobis(2-nitrobenzoic acid

TNB: 2-nitro-5-thiobenzoic acid

HEPES: (4-(2-hydroxyethyl)-1-piperazineethanesulfonic acid)

Preparations of Compounds 1 to 9 in Table 1 are illustrated as Examples 1 to 9 below. Furthermore, preparations of Compounds 10 to 33 in Table 1 are described in WO 2019/159120 as Examples 7 to 30, the content of which is hereby incorporated by reference in its entirety.

Example 1: (2R,4S)-4-amino-2-(4-boronobutyl) piperidine-2-carboxylic acid

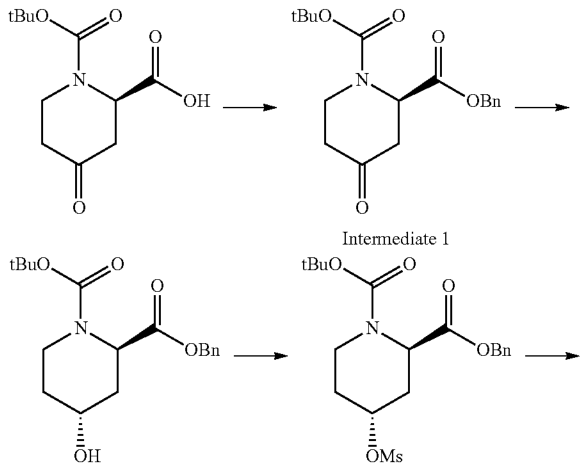

Intermediate 1

Intermediate 2

Intermediate 3

-continued

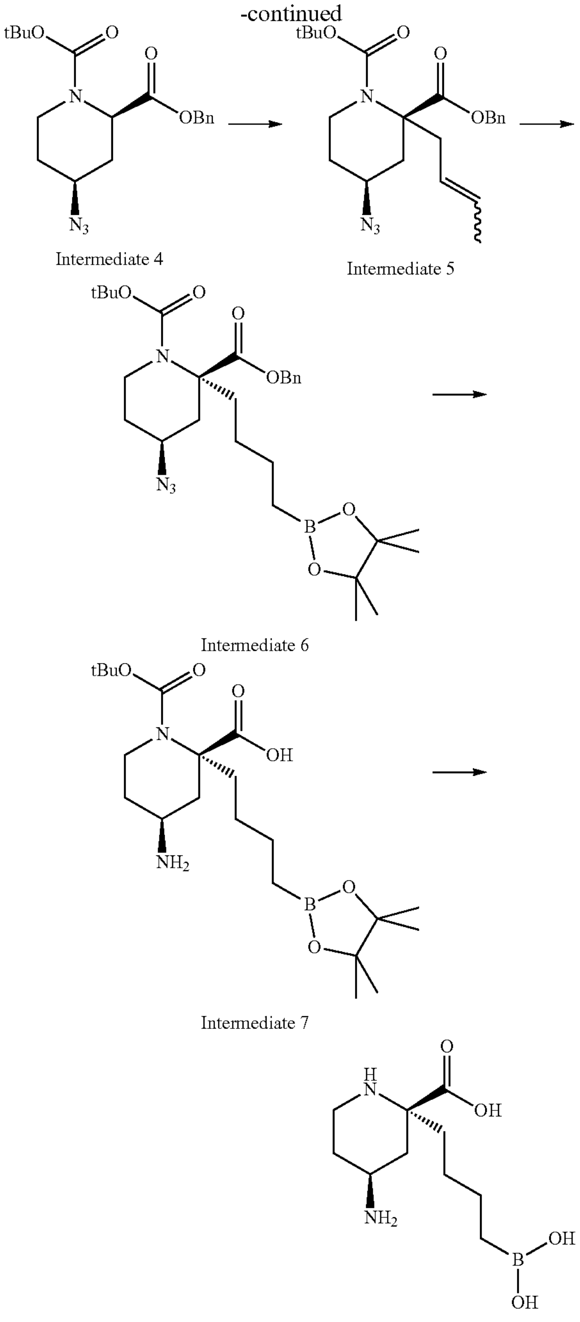

Intermediate 4

Intermediate 5

Intermediate 6

Intermediate 7

Example 1

Intermediate 1: 2-benzyl 1-(tert-butyl) (R)-4-oxopiperidine-1,2-dicarboxylate

N,N'-diisopropylcarbodiimide (3.49 mL, 22.4 mmol) and DMAP (0.249 g, 2.04 mmol) were added to a stirred solution of (R)-1-(tert-butoxycarbonyl)-4-oxopiperidine-2-carboxylic acid (4.955 g, 20.37 mmol) and benzyl alcohol (2.11 mL, 20.4 mmol) in DCM (150 mL) at 0° C. The reaction stirred for 17 h while slowly warming to room temperature. The reaction mixture was filtered and the filtrate was concentrated to dryness. The resulting residue was purified by flash silica chromatography (5 to 50% EtOAc in hexanes) to afford 2-benzyl 1-(tert-butyl) (R)-4-oxopiperidine-1,2-dicarboxylate (Intermediate 1, 6.50 g, 96% yield) as a colorless oil and as a mixture of rotamers. $^1$H NMR (500 MHz, $CDCl_3$) δ 1.40 (5H, br s), 1.49 (4H, br s), 2.43-2.65 (2H, m), 2.70-2.92 (2H, m), 3.53-3.74 (1H, m), 3.94-4.10 (1H, m), 4.89 (0.5H, br s), 5.10-5.23 (2.5H, m), 7.31-7.41 (5H, m); m/z: ($ES^+$) $[M+Na]^+$=356.

Intermediate 2: 2-benzyl 1-(tert-butyl) (2R,4R)-4-hydroxypiperidine-1,2-dicarboxylate Sodium borohydride (0.738 g, 19.5 mmol) was added portion-wise to a stirred solution of 2-benzyl 1-(tert-butyl) (R)-4-oxopiperidine-1,2-dicarboxylate (Intermediate 1, 6.504 g, 19.51 mmol) in a mixture of MeOH/THF (1:20, 105 mL) at 0° C. The mixture was stirred for 5 h then carefully quenched with 1 M HCl (aq) (15 mL—gas evolution) and warmed to room temperature. The mixture was diluted with water (25 mL) and EtOAc (50 mL). The phases were separated and the aqueous phase was extracted with EtOAc (4×20 mL). The combined organics were washed with saturated aqueous NaCl, dried over $MgSO_4$, filtered and concentrated to dryness. The resulting residue was purified by flash silica chromatography (5 to 45% EtOAc in hexanes) to afford 2-benzyl 1-(tert-butyl) (2R,4R)-4-hydroxypiperidine-1,2-dicarboxylate (Intermediate 2, 3.84 g, 59% yield) as a colorless gum of a 5:1 mixture of diastereomers (major diastereomer is the title compound) and as a mixture of rotamers. $^1$H NMR (500 MHz, $CDCl_3$) δ 1.38 (5H, br s), 1.40-1.44 (2H, m), 1.46 (5.4H, br s), 1.60-1.69 (1.4H, m), 1.70-1.79 (0.2H, m), 1.83-1.97 (1.2H, m), 2.48 (1H, br dd), 2.92-3.08 (1H, m), 3.28-3.46 (0.2H, m), 3.54-3.70 (1H, m), 3.76-3.84 (0.1H, m), 3.87-3.96 (0.1H, m), 4.00 (0.5H, br d), 4.15 (0.5H, s), 4.65-4.74 (0.1H, m), 4.87 (0.6H, br d), 5.08 (0.5H, br d), 5.13-5.26 (2.4H, m), 7.31-7.40 (6H, m); m/z: ($ES^+$) $[M+Na]^+$=358.

Intermediate 3: 2-benzyl 1-(tert-butyl) (2R,4R)-4-((methylsulfonyl)oxy)piperidine-1,2-dicarboxylate Methanesulfonic anhydride (3.59 g, 20.6 mmol) was added portion-wise to a stirred solution of 2-benzyl 1-(tert-butyl) (2R,4R)-4-hydroxypiperidine-1,2-dicarboxylate (Intermediate 2, 3.84 g, 11.5 mmol; 5:1 mixture of diastereomers) and triethylamine (3.35 mL, 24.0 mmol) in DCM (50 mL) at 0° C. The cooling bath was allowed to expire and the reaction warmed to room temperature. After 6 h the reaction was diluted with DCM (50 mL) and washed sequentially with 1 M HCl (aq) (50 mL) and saturated aqueous NaCl (50 mL). The organic layer was dried over $MgSO_4$, filtered and concentrated to dryness to afford crude 2-benzyl 1-(tert-butyl) (2R,4R)-4-((methylsulfonyl)oxy)piperidine-1,2-dicarboxylate (Intermediate 3, 4.73 g, 100% yield) as a pale orange gum and a mixture of diastereomers. The crude material was used directly without further purification. m/z: ($ES^+$) $[M+Na]^+$=436.

Intermediate 4: 2-benzyl 1-(tert-butyl) (2R,4S)-4-azidopiperidine-1,2-dicarboxylate Sodium azide (3.72 g, 57.2 mmol) was added to a stirred solution of 2-benzyl 1-(tert-butyl) (2R,4R)-4-((methylsulfonyl)oxy)piperidine-1,2-dicarboxylate (Intermediate 3, 4.73 g, 11.4 mmol; mixture of diastereomers) in DMF (50 mL) and the reaction was warmed to 60° C. for 20 h. The mixture was allowed to cool to room temperature, filtered and the filtrate was diluted with water (400 mL) and EtOAc (40 mL). The phases were separated and the aqueous phase was extracted with EtOAc (4×40 mL). The combined organics were washed with saturated aqueous NaCl (2×40 mL), dried over $MgSO_4$, filtered and concentrated to dryness. The resulting residue was purified by flash silica chromatography (5 to 30% EtOAc in hexanes) to afford diastereomerically pure 2-benzyl 1-(tert-butyl) (2R,4S)-4-azidopiperidine-1,2-dicarboxylate (Intermediate 4, 2.58 g, 63% yield) as a colorless gum and a mixture of rotamers. $^1$H NMR (500 MHz, $CDCl_3$) δ 1.39 (4H, br s), 1.46 (5H, br s), 1.63-1.73 (1H, m), 1.74-1.87 (1H, m), 1.95 (1H, ddd), 2.50-2.61 (1H, m), 3.03-3.44 (1H, m), 3.73-3.89 (0.5H, m), 3.90-4.01 (1.5H, m), 4.58-4.74 (0.5H, m), 4.88 (0.5H, br s), 5.15-5.34 (2H, m), 7.30-7.43 (5H, m); m/z: ($ES^+$) $[M-Boc]^+$=261.

Intermediate 5: 2-benzyl 1-(tert-butyl) (4S)-4-azido-2-(but-2-en-1-yl)piperidine-1, 2-dicarboxylate 2-Benzyl 1-(tert-butyl) (2R,4S)-4-azidopiperidine-1,2-dicarboxylate (Intermediate 4, 1.94 g, 5.38 mmol) and crotyl bromide (0.977 mL, 8.07 mmol) were dissolved in THF (30 mL) and the solution was cooled to −78° C. A solution of KHMDS (1 M in 2-methyltetrahydrofuran, 7.0 mL, 7.0 mmol) was added dropwise over 10 min. The reaction mixture was slowly warmed to room temperature and stirred for a total of 18 h. The crude reaction mixture was quenched with saturated aqueous $NH_4Cl$ then diluted with saturated aqueous NaCl and EtOAc (50 mL). The phases were separated and the aqueous layer was extracted with EtOAc (3×30 mL). The combined organics were washed with saturated aqueous NaCl, dried over $MgSO_4$, filtered and concentrated to dryness. The resulting residue was purified by flash silica chromatography (2 to 30% EtOAc in hexanes) to afford 2-benzyl 1-(tert-butyl) (4S)-4-azido-2-(but-2-en-1-yl)piperidine-1,2-dicarboxylate (Intermediate 5, 2.106 g, 94% yield) as a syn/anti diastereomeric mixture and as a mixture of rotamers and E/Z olefins. $^1$H NMR (500 MHz, $CD_2Cl_2$) δ 1.40-1.42 (4H, m), 1.43 (5H, br s), 1.49-1.58 (1H, m), 1.59-1.66 (0.6H, m), 1.67-1.74 (3.4H, m), 1.86 (0.5H, dd), 1.89-2.05 (2H, m), 2.07-2.19 (1H, m), 2.42 (0.5H, dd), 2.58-2.69 (1H, m), 2.71-2.83 (0.5H, m), 3.01-3.16 (0.5H, m), 3.21 (0.5H, br dd), 3.31-3.44 (0.5H, m), 3.61-3.77 (1.5H, m), 3.97-4.07 (0.5H, m), 5.10-5.27 (2H, m), 5.36-5.45 (1H, m), 5.51-5.74 (2H, m), 7.32-7.47 (5H, m); m/z: ($ES^+$) $[M-Boc]^+$=315.

Intermediate 6: 2-benzyl 1-(tert-butyl) (2R,4S)-4-azido-2-(4-(4,4,5,5-tetramethyl-1,3,2-dioxaborolan-2-yl)butyl)piperidine-1,2-dicarboxylate Bis(1,5-cyclooctadiene)diiridium(I) dichloride (50 mg, 0.074 mmol) and bis(diphenylphosphino)methane (57 mg, 0.15 mmol) were added to an oven-dried round-bottom flask. The flask was sealed and purged with $N_2$. The solids were dissolved in DCM (9 mL) and 4,4,5,5-tetramethyl-1,3,2-dioxaborolane (0.32 mL, 2.2 mmol) was slowly added to the solution. The reaction was stirred at room temperature for 10 min. 2-benzyl 1-(tert-butyl) (4S)-4-azido-2-(but-2-en-1-yl)piperidine-1,2-dicarboxylate (Intermediate 5, 616 mg, 1.49 mmol) was added to the reaction as a solution in DCM (3 mL) and the reaction mixture stirred for 66 h at room temperature. The reaction mixture was cooled to 0° C. and carefully quenched with MeOH (1 mL) and water (5 mL). The layers were separated and the aqueous layer was extracted with DCM (3×15 mL). The combined organics were dried over $MgSO_4$, filtered and concentrated to dryness. The resulting residue was purified by flash silica chromatography (5 to 15% EtOAc in hexanes) to afford diastereomerically pure 2-benzyl 1-(tert-butyl) (2R,4S)-4-azido-2-(4-(4,4,5,5-tetramethyl-1,3,2-dioxaborolan-2-yl)butyl)piperidine-1,2-dicarboxylate (Intermediate 6, 261 mg, 32% yield) as a clear, colorless gum. $^1$H NMR (500 MHz, $CDCl_3$) δ 0.79 (2H, t), 1.25 (12H, s), 1.29-1.35 (1H, m), 1.36-1.39 (1H, m), 1.41 (9H, s), 1.42-1.46 (2H, m), 1.57-1.68 (1H, m), 1.85-1.94 (3H, m), 1.95-2.01 (1H, m), 2.05 (1H, dd), 2.92-3.11 (1H, m), 3.49-3.72 (1H, m), 3.98-4.03 (1H, m), 5.09 (1H, d), 5.18 (1H, d), 7.29-7.42 (5H, m); m/z: ($ES^+$) $[M+Na]^+$=565.

Intermediate 7: (2R,4S)-4-amino-1-(tert-butoxycarbonyl)-2-(4-(4,4,5,5-tetramethyl-1,3,2-dioxaborolan-2-yl)butyl)piperidine-2-carboxylic acid Pd/C (10% wt, 50 mg, 0.047 mmol) was added to a solution of 2-benzyl 1-(tert-butyl) (2R,4S)-4-azido-2-(4-(4,4,5,5-tetramethyl-1,3,2-dioxaborolan-2-yl)butyl)piperidine-1,2-dicarboxylate (Intermediate 6, 268 mg 0.494 mmol) in EtOAc (3 mL). The suspension was stirred under a hydrogen atmosphere (balloon, flask evacuated and back-filled with hydrogen ×3) at room temperature for 17 h. The reaction mixture was diluted with MeOH (5 mL), filtered through diatomaceous earth and concentrated to dryness. The resulting residue was purified by flash silica chromatography (5 to 45% MeOH in DCM) to afford (2R,4S)-4-amino-1-(tert-butoxycarbonyl)-2-(4-(4,4,5,5-tetramethyl-1,3,2-dioxaborolan-2-yl)butyl)piperidine-2-carboxylic acid (Intermediate 7, 156 mg, 74% yield) as a white dry film. $^1$H NMR (500 MHz, $CD_2Cl_2$) δ 0.71 (2H, t), 1.07-1.16 (1H, m), 1.19 (14H, s), 1.31-1.37 (2H, m), 1.40 (9H, s), 1.80-1.96 (1H, m), 2.02 (3H, br d), 2.33 (1H, br s), 3.00 (1H, br s), 3.53 (1H, br s), 3.92 (1H, br s), 8.60 (3H, br s); m/z: ($ES^+$) $[M+H]^+$=427.

Example 1: (2R,4S)-4-amino-2-(4-boronobutyl)piperidine-2-carboxylic acid

Trifluoroacetic acid (0.53 mL, 6.9 mmol) was added dropwise to a stirred solution of (2R,4S)-4-amino-1-(tert-butoxycarbonyl)-2-(4-(4,4,5,5-tetramethyl-1,3,2-dioxaborolan-2-yl)butyl)piperidine-2-carboxylic acid (Intermediate 7, 146 mg, 0.342 mmol) in DCM (2 mL) at room temperature. After 2 h the solution was concentrated under reduced pressure and the resulting residue was dissolved in 1 M HCl (aq) (3.0 mL, 3.0 mmol) and $Et_2O$ (3 mL). Phenylboronic acid (125 mg, 1.03 mmol) was added and the clear biphasic solution stirred at room temperature for 4 h. The mixture was diluted with $Et_2O$ (20 mL) and water (5 mL) and the layers were separated. The aqueous layer was washed with $Et_2O$. The aqueous layer was lyophilized and purified by ion exchange chromatography (PoraPak Rxn CX 20 cc column). The desired product was eluted from the column using 5% ammonia in MeOH (20 mL) to afford (2R,4S)-4-amino-2-(4-boronobutyl)piperidine-2-carboxylic acid (62 mg, 74% yield) as a white solid. $^1$H NMR (500 MHz, $D_2O$) δ 0.71-0.82 (2H, m), 1.10-1.30 (2H, m), 1.33-1.44 (2H, m), 1.45-1.55 (1H, m), 1.62 (1H, dd), 1.77 (1H, ddd), 1.84-1.93 (1H, m), 2.01-2.08 (1H, m), 2.18 (1H, ddd), 3.07 (1H, td), 3.22 (1H, dt), 3.28-3.39 (1H, m); m/z: ($ES^+$) $[M+H]^+$=245.

Example 2: (2R,4S)-4-((S)-2-amino-3-methylbutanamido)-2-(4-boronobutyl)piperidine-2-carboxylic acid

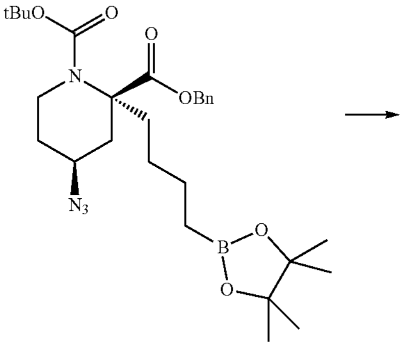

Intermediate 6

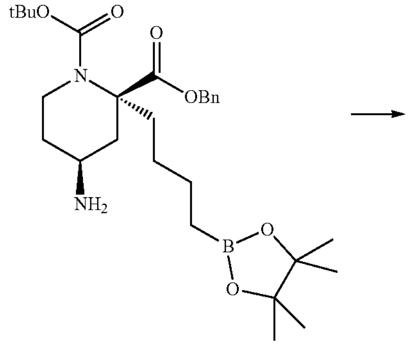

Intermediate 8

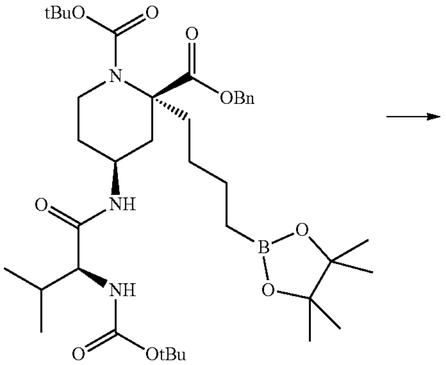

Intermediate 9

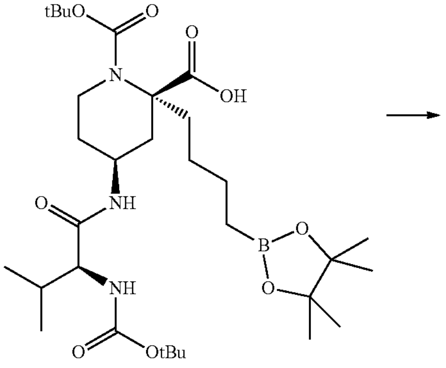

Intermediate 10

-continued

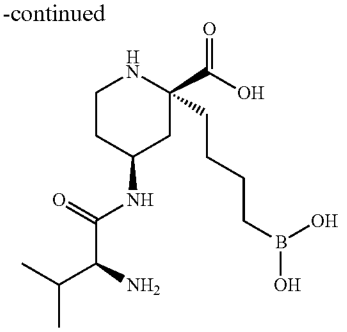

Example 2

Intermediate 8: 2-benzyl 1-(tert-butyl) (2R,4S)-4-amino-2-(4-(4,4,5,5-tetramethyl-1,3,2-dioxaborolan-2-yl)butyl)piperidine-1,2-dicarboxylate Zinc (270 mg, 4.14 mmol) and AcOH (1.20 mL, 20.9 mmol) were added to a stirred solution of 2-benzyl 1-(tert-butyl) (2R,4S)-4-azido-2-(4-(4,4,5,5-tetramethyl-1,3,2-dioxaborolan-2-yl)butyl)piperidine-1,2-dicarboxylate (Intermediate 6, 748 mg, 1.38 mmol) in THF (10 mL). The rapidly stirred mixture was heated to 30° C. for 18 h. The mixture was cooled to room temperature, diluted with DCM (30 mL) and filtered through diatomaceous earth. The filter cake was washed with DCM and the filtrate was concentrated to dryness. The resulting residue was partitioned between EtOAc (40 mL) and saturated aqueous $NaHCO_3$. The phases were separated and the organics were washed with saturated aqueous $NaHCO_3$ and saturated aqueous NaCl. The organics were dried over $MgSO_4$, filtered, and concentrated to dryness to afford 2-benzyl 1-(tert-butyl) (2R,4S)-4-amino-2-(4-(4,4,5,5-tetramethyl-1,3,2-dioxaborolan-2-yl)butyl)piperidine-1,2-dicarboxylate (Intermediate 8, 713 mg, 100% yield) as a clear colorless gum. The crude material was used directly without further purification. $^1H$ NMR (500 MHz, $CDCl_3$) δ 0.79 (2H, t), 1.24 (12H, s), 1.32-1.38 (2H, m), 1.39-1.47 (13H, m), 1.68 (2H, br t), 1.83-1.99 (4H, m), 2.93 (1H, td), 2.97-3.07 (1H, m), 3.96-4.10 (1H, m), 5.06-5.23 (2H, m), 7.30-7.41 (5H, m); m/z: ($ES^+$) $[M+H]^+$=517.

Intermediate 9: 2-benzyl 1-(tert-butyl) (2R,4S)-4-((S)-2-((tert-butoxycarbonyl)amino)-3-methylbutanamido)-2-(4-(4,4,5,5-tetramethyl-1,3,2-dioxaborolan-2-yl)butyl)piperidine-1,2-dicarboxylate N,N-Diisopropylethylamine (0.12 mL, 0.63 mmol) was added slowly to a stirred solution of COMU (270 mg, 0.63 mmol) and Boc-Val-OH (137 mg, 0.631 mmol) in DMF (2 mL) at room temperature. The solution stirred at room temperature for 30 min and was then cooled to 0° C. A solution of 2-benzyl 1-(tert-butyl) (2R,4S)-4-amino-2-(4-(4,4,5,5-tetramethyl-1,3,2-dioxaborolan-2-yl)butyl)piperidine-1,2-dicarboxylate (Intermediate 8, 310 mg, 0.60 mmol) in DMF (2 mL) and N,N-Diisopropylethylamine (0.10 mL, 0.60 mmol) were added and the reaction stirred for 17 h while slowly warming to room temperature. The reaction mixture was diluted with water (40 mL) and the resulting precipitate was collected by filtration. The solid was dissolved in EtOAc, dried over $MgSO_4$, filtered and concentrated to dryness. The resulting residue was purified by flash silica chromatography (10 to 100% EtOAc in hexanes) to afford 2-benzyl 1-(tert-butyl) (2R,4S)-4-((S)-2-((tert-butoxycarbonyl)amino)-3-methylbutanamido)-2-(4-(4,4,5,5-tetramethyl-1,3,2-dioxaborolan-2-yl)butyl)piperidine-1,2-dicarboxylate (Intermediate 9, 184 mg, 43% yield) as a colorless film and as a mixture of rotamers. $^1H$ NMR (500 MHz, $CDCl_3$) δ 0.73-0.80 (2H, m), 0.85 (3H, d), 0.89 (3H, d), 1.22 (12H, br s), 1.23-1.29 (2H, m), 1.37-1.45 (20H, m), 1.62-1.74 (1H, m), 1.86-1.99 (3H, m), 2.00-2.12 (3H, m), 2.97 (1H, t), 3.78 (1H, t), 3.94-4.06 (1H, m), 4.07-4.14 (1H, m), 5.00 (1H, br s), 5.05-5.24 (2H, m), 6.05 (1H, br d), 7.28-7.36 (5H, m); m/z: ($ES^+$) $[M+H]^+$=716.

Intermediate 10: (2R,4S)-1-(tert-butoxycarbonyl)-4((S)-2-((tert-butoxycarbonyl)amino)-3-methylbutanamido)-2-(4-(4,4,5,5-tetramethyl-1,3,2-dioxaborolan-2-yl)butyl)piperidine-2-carboxylic acid Pd/C (10% wt, 27 mg, 0.025 mmol) was added to a solution of 2-benzyl 1-(tert-butyl) (2R,4S)-4((S)-2-((tert-butoxycarbonyl)amino)-3-methylbutanamido)-2-(4-(4,4,5,5-tetramethyl-1,3,2-dioxaborolan-2-yl)butyl)piperidine-1,2-dicarboxylate (Intermediate 9, 184 mg, 0.257 mmol) in EtOAc (2 mL). The suspension was stirred under a hydrogen atmosphere (balloon, flask evacuated and back-filled with hydrogen ×3) at room temperature for 16 h. The reaction mixture was diluted with EtOAc (20 mL) and MeOH (20 mL), filtered through diatomaceous earth and concentrated to dryness. The resulting residue was purified by flash silica chromatography (20 to 100% EtOAc in hexanes followed by 10% MeOH in DCM) to afford (2R,4S)-1-(tert-butoxycarbonyl)-4-((S)-2-((tert-butoxycarbonyl)amino)-3-methylbutanamido)-2-(4-(4,4,5,5-tetramethyl-1,3,2-dioxaborolan-2-yl)butyl)piperidine-2-carboxylic acid (Intermediate 10, 116 mg, 72% yield) as a white solid and as a mixture of rotamers. $^1H$ NMR (500 MHz, $CDCl_3$) δ 0.78 (3H, br d), 0.83-0.91 (2H, m), 0.94 (3H, br d), 1.20-1.25 (12H, m), 1.40 (9H, br s), 1.42-1.53 (11H, m), 1.51-1.66 (1H, m), 1.75-2.18 (4H, m), 2.19-2.34 (1H, m), 2.88-3.06 (1H, m), 3.85-4.06 (2H, m), 4.07-4.26 (1H, m), 5.14 (1H, br s), 5.93 (1H, br s), 6.73 (1H, br s), 7.30-7.48 (1H, m); m/z: ($ES^+$) $[M+H]^+$=627.

Example 2: (2R,4S)-4-((S)-2-amino-3-methylbutanamido)-2-(4-boronobutyl)piperidine-2-carboxylic acid Trifluoroacetic acid (0.433 mL, 5.63 mmol) was added dropwise to a stirred solution of (2R,4S)-1-(tert-butoxycarbonyl)-4-((S)-2-((tert-butoxycarbonyl)amino)-3-methylbutanamido)-2-(4-(4,4,5,5-tetramethyl-1,3,2-dioxaborolan-2-yl)butyl)piperidine-2-carboxylic acid (Intermediate 10, 176 mg, 0.281 mmol) in DCM (2 mL) at room temperature. After 3 h the solution was concentrated under reduced pressure and the resulting residue was dissolved in 1 M HCl (aq) (3.0 mL, 3.0 mmol) and $Et_2O$ (3 mL). Phenylboronic acid (103 mg, 0.845 mmol) was added and the clear biphasic solution stirred at room temperature for 4 h. The mixture was diluted with $Et_2O$ (20 mL) and water (5 mL) and the layers were separated. The aqueous layer was washed with $Et_2O$. The aqueous layer was lyophilized and purified by ion exchange chromatography (PoraPak Rxn CX 20 cc column). The desired product was eluted from the column using 5% ammonia in MeOH (20 mL) to afford (2R,4S)-4-((S)-2-amino-3-methylbutanamido)-2-(4-boronobutyl)piperidine-2-carboxylic acid (Example 2, 89 mg, 92% yield) as a white solid. $^1H$ NMR (500 MHz, $D_2O$) δ 0.73-0.83 (2H, m), 0.88-0.96 (6H, m), 1.14-1.24 (1H, m), 1.25-1.35 (1H, m), 1.37-1.50 (2H, m), 1.64-1.76 (1H, m), 1.79-1.99 (4H, m), 2.01-2.09 (1H, m), 2.17 (1H, dd), 3.11 (1H, d), 3.16-3.24 (1H, m), 3.31 (1H, dt), 4.10-4.22 (1H, m); m/z: ($ES^+$) $[M+H]^+$=344.

Example 3: (2R,4S)-4-(2-aminoacetamido)-2-(4-boronobutyl)piperidine-2-carboxylic acid

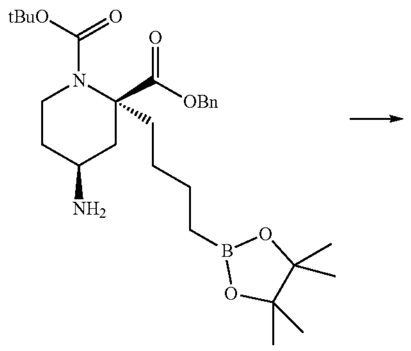

Intermediate 8

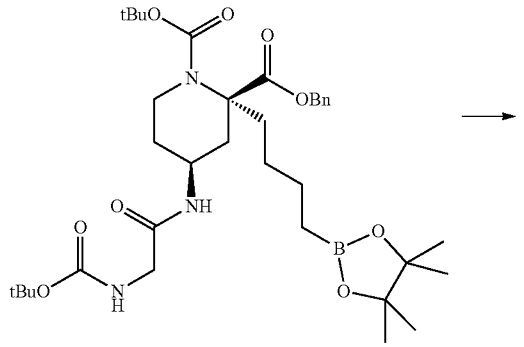

Intermediate 11

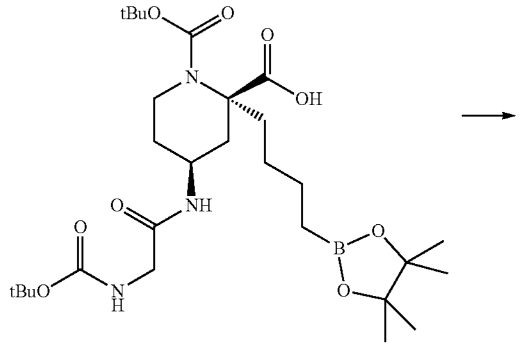

Intermediate 12

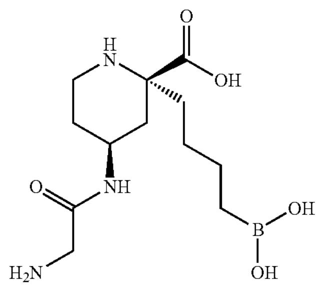

Example 3

Intermediate 11: 2-benzyl 1-(tert-butyl) (2R,4S)-4-(2-((tert-butoxycarbonyl)amino)acetamido)-2-(4-(4,4,5,5-tetramethyl-1,3,2-dioxaborolan-2-yl)butyl)piperidine-1,2-dicarboxylate N,N-Diisopropylethylamine (0.12 mL, 0.63 mmol) was added slowly to a stirred solution of COMU (270 mg, 0.63 mmol) and Boc-Gly-OH (110 mg, 0.63 mmol) in DMF (2 mL) at room temperature. The solution stirred at room temperature for 30 min and was then cooled to 0° C. A solution of 2-benzyl 1-(tert-butyl) (2R,4S)-4-amino-2-(4-(4,4,5,5-tetramethyl-1,3,2-dioxaborolan-2-yl)butyl)piperidine-1,2-dicarboxylate (Intermediate 8, 310 mg, 0.60 mmol) in DMF (2 mL) and N,N-Diisopropylethylamine (0.11 mL, 0.60 mmol) were added and the reaction stirred for 17 h while slowly warming to room temperature. The reaction mixture was diluted with water (60 mL) and the pH was adjusted to ~5 with acetic acid. The aqueous phase was extracted with EtOAc (4×15 mL). The combined organics were washed with saturated aqueous NaCl (2×10 mL), dried over $MgSO_4$, filtered and concentrated to dryness The resulting residue was purified by flash silica chromatography (10 to 100% EtOAc in hexanes) to afford 2-benzyl 1-(tert-butyl) (2R,4S)-4-(2-((tert-butoxycarbonyl)amino)acetamido)-2-(4-(4,4,5,5-tetramethyl-1,3,2-dioxaborolan-2-yl)butyl)piperidine-1,2-dicarboxylate (Intermediate 11, 204 mg, 51% yield) as a colorless film and as a mixture of rotamers. $^1H$ NMR (500 MHz, $CDCl_3$) δ 0.75 (2H, br t), 1.21 (14H, s), 1.24 (2H, br d), 1.38 (9H, s), 1.40 (10H, s), 1.71 (1H, dd), 1.81-1.91 (1H, m), 1.93-2.04 (3H, m), 2.86-3.04 (1H, m), 3.62 (2H, br s), 3.93-4.04 (1H, m), 4.06-4.15 (1H, m), 5.11 (2H, s), 5.14 (1H, br s), 6.27 (1H, br s), 7.28-7.40 (5H, m); m/z: ($ES^+$) $[M+H]^+$=674.

Intermediate 12: (2R,4S)-1-(tert-butoxycarbonyl)-4-(2-((tert-butoxycarbonyl)amino)acetamido)-2-(4-(4,4,5,5-tetramethyl-1,3,2-dioxaborolan-2-yl)butyl)piperidine-2-carboxylic acid Pd/C (10% wt, 32 mg, 0.030 mmol) was added to a solution of 2-benzyl 1-(tert-butyl) (2R,4S)-4-(2-((tert-butoxycarbonyl)amino)acetamido)-2-(4-(4,4,5,5-tetramethyl-1,3,2-dioxaborolan-2-yl)butyl)piperidine-1,2-dicarboxylate (Intermediate 11, 204 mg, 0.303 mmol) in EtOAc (2 mL). The suspension was stirred under a hydrogen atmosphere (balloon, flask evacuated and back-filled with hydrogen ×3) at room temperature for 16 h. The reaction mixture was diluted with EtOAc (20 mL) and MeOH (20 mL), filtered through diatomaceous earth and the filtrate was concentrated to dryness. The resulting residue was purified by flash silica chromatography (25 to 100% EtOAc in hexanes) to afford (2R,4S)-1-(tert-butoxycarbonyl)-4-(2-((tert-butoxycarbonyl)amino)acetamido)-2-(4-(4,4,5,5-tetramethyl-1,3,2-dioxaborolan-2-yl)butyl)piperidine-2-carboxylic acid (Intermediate 12, 117 mg, 66% yield) as a white solid and as a mixture of rotamers. $^1H$ NMR (500 MHz, $CDCl_3$) δ 0.78 (2H, t), 1.17-1.29 (13H, m), 1.40 (10H, br s), 1.45 (9H, s), 1.48-1.57 (2H, m), 1.76-2.01 (3H, m), 2.04-2.13 (1H, m), 2.98 (1H, br t), 3.47-3.66 (1H, m), 3.75 (1H, s), 3.90-4.06 (2H, m), 4.13-4.25 (1H, m), 5.41 (1H, br s), 5.92 (1H, br s), 6.73 (1H, br s), 7.65 (1H, br s); m/z: ($ES^+$) $[M+H]^+$=584.

Example 3: (2R,4S)-4-(2-aminoacetamido)-2-(4-boronobutyl)piperidine-2-carboxylic acid Trifluoroacetic acid (0.31 mL, 4.0 mmol) was added dropwise to a stirred solution of (2R,4S)-1-(tert-butoxycarbonyl)-4-(2-((tert-butoxycarbonyl)amino)acetamido)-2-(4-(4,4,5,5-tetramethyl-1,3,2-dioxaborolan-2-yl)butyl)piperidine-2-carboxylic acid (Intermediate 12, 117 mg, 0.201 mmol) in DCM (2 mL) at room temperature. After 3 h the solution was concentrated under reduced pressure and the resulting residue was dissolved in 1 M HCl (aq) (3.0 mL, 3.0 mmol) and $Et_2O$ (3 mL). Phenylboronic acid (73 mg, 0.60 mmol) was added and the clear biphasic solution stirred at room temperature for 4 h. The mixture was diluted with $Et_2O$ (20 mL) and water (5 mL) and the layers were separated. The aqueous layer was washed with $Et_2O$. The aqueous layer was lyophilized and purified by ion exchange chromatography (PoraPak Rxn CX 20 cc column). The desired product was eluted from the column using 5% ammonia in MeOH (20 mL) to afford (2R,4S)-4-(2-amino-acetamido)-2-(4-boronobutyl)piperidine-2-carboxylic acid (Example 3, 61 mg, 100% yield) as a white solid. $^1H$ NMR (500 MHz, $D_2O$) δ 0.72-0.84 (2H, m), 1.14-1.25 (1H, m), 1.26-1.34 (1H, m), 1.41 (2H, quin), 1.72 (1H, dtd), 1.79-1.94 (2H, m), 1.96-2.08 (2H, m), 2.10 (1H, dd), 3.14-3.25 (1H, m), 3.30-3.36 (1H, m), 3.37 (2H, s), 4.08-4.19 (1H, m); m/z: ($ES^+$) $[M+H]^+$=302.

Example 4: (2R,4S)-4-[[(2S)-2-aminopropanoyl]amino]-2-(4-boronobutyl)piperidine-2-carboxylic acid

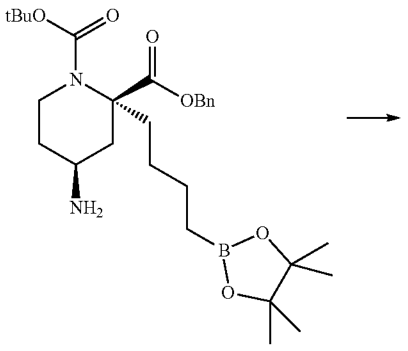

Intermediate 8

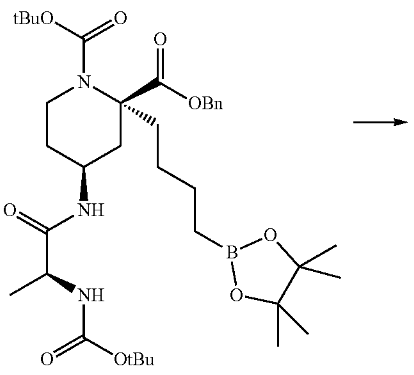

Intermediate 13

-continued

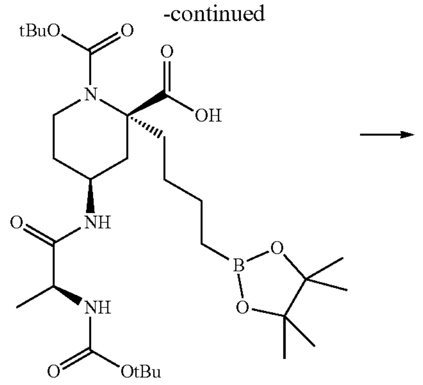

Intermediate 14

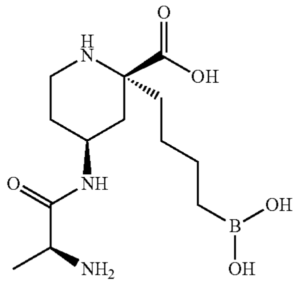

Example 4

Intermediate 13: 2-benzyl 1-tert-butyl (2R,4S)-4-[[(2S)-2-(tert-butoxycarbonylamino)propanoyl]amino]-2-[4-(4,4,5,5-tetramethyl-1,3,2-dioxaborolan-2-yl)butyl]piperidine-1,2-dicarboxylate N,N-Diisopropylethylamine (0.17 mL, 1.0 mmol) was added slowly to a stirred solution of 2-benzyl 1-(tert-butyl) (2R,4S)-4-amino-2-(4-(4,4,5,5-tetramethyl-1,3,2-dioxaborolan-2-yl)butyl)piperidine-1,2-dicarboxylate (Intermediate 8, 245 mg, 0.474 mmol), Boc-Ala-OH (108 mg, 0.571 mmol) and COMU (244 mg, 0.571 mmol) in DMF (1.5 mL) at 0° C. The reaction stirred for 1.5 h while slowly warming to room temperature. The reaction mixture was diluted with water (20 mL) and EtOAc (20 mL) and the phases were separated. The aqueous phase was extracted with EtOAc (3×20 mL) and the combined organics were washed with saturated aqueous NaCl, dried over $MgSO_4$, filtered and concentrated to dryness. The resulting residue was purified by flash silica chromatography (15 to 80% EtOAc in hexanes) to afford 2-benzyl 1-tert-butyl (2R,4S)-4-[[(2S)-2-(tert-butoxycarbonylamino)propanoyl]amino]-2-[4-(4,4,5,5-tetramethyl-1,3,2-dioxaborolan-2-yl)butyl]piperidine-1,2-dicarboxylate (Intermediate 13, 191 mg, 59% yield) as a pale-yellow gum and as a mixture of rotamers. $^1H$ NMR (500 MHz, $CDCl_3$) δ 0.69-0.83 (2H, m), 1.22 (12H, d), 1.26 (5H, td), 1.38 (9H, br s), 1.40 (9H, br d), 1.42-1.49 (3H, m), 1.57-1.73 (1H, m), 1.83-1.98 (3H, m), 2.01-2.05 (2H, m), 2.91-3.03 (1H, m), 4.02 (2H, br s), 4.96 (1H, br s), 5.05-5.22 (2H, m), 6.21 (1H, br s), 7.27-7.36 (5H, m); m/z: ($ES^+$) $[M+H]^+$=688.

Intermediate 14: (2R,4S)-1-tert-butoxycarbonyl-4-[[(2S)-2-(tert-butoxycarbonylamino)propanoyl]amino]-2-[4-(4,4,5,5-tetramethyl-1,3,2-dioxaborolan-2-yl)butyl]piperidine-2-carboxylic acid Pd/C (10% wt, 15 mg, 0.014 mmol) was added to a solution of 2-benzyl 1-tert-butyl (2R,4S)-4-[[(2S)-2-(tert-butoxycarbonylamino)propanoyl]amino]-2-[4-(4,4,5,5-tetramethyl-1,3,2-dioxaborolan-2-yl)butyl]piperidine-1,2-dicarboxylate (Intermediate 13, 190 mg, 0.28 mmol) in EtOAc (2 mL). The suspension was stirred under a hydrogen atmosphere (balloon, flask evacuated and back-filled with hydrogen ×3) at room temperature for 17 h. The reaction mixture was diluted with EtOAc (15 mL) and MeOH (2 mL), filtered through diatomaceous earth and concentrated to dryness. The resulting residue was purified by flash silica chromatography (20 to 100% EtOAc in hexanes) to afford (2R,4S)-1-ted-butoxycarbonyl-4-[[(2S)-2-(tert-butoxycarbonylamino)propanoyl]amino]-2-[4-(4,4,5,5-tetramethyl-1,3,2-dioxaborolan-2-yl)butyl]piperidine-2-carboxylic acid (Intermediate 14, 134 mg, 81% yield) as a dry film and as a mixture of rotamers. $^1$H NMR (500 MHz, $CDCl_3$) δ 0.78 (2H, br t), 1.20-1.25 (12H, m), 1.29-1.36 (5H, m), 1.41 (9H, s), 1.44 (11H, s), 1.48-1.62 (2H, m), 1.77-2.01 (3H, m), 2.09 (2H, br s), 2.97 (1H, br s), 3.92-4.05 (1H, m), 5.07 (1H, br s), 5.48 (1H, br s), 6.71 (1H, br s), 7.61 (1H, br s); m/z: (ES$^+$) [M+H]$^+$=598.

Example 4: (2R,4S)-4-[[(2S)-2-aminopropanoyl]amino]-2-(4-boronobutyl)piperidine-2-carboxylic acid Trifluoroacetic acid (0.34 mL, 4.4 mmol) was added dropwise to a stirred solution of (2R,4S)-1-tert-butoxycarbonyl-4-[[(2S)-2-(tert-butoxycarbonylamino)propanoyl]amino]-2-[4-(4,4,5,5-tetramethyl-1,3,2-dioxaborolan-2-yl)butyl]piperidine-2-carboxylic acid (Intermediate 14, 130 mg, 0.22 mmol) in DCM (1 mL) at room temperature. After 3 h the solution was concentrated under reduced pressure and the resulting residue was dissolved in 1 M HCl (aq) (2.0 mL, 2.0 mmol) and $Et_2O$ (2 mL). Phenylboronic acid (80 mg, 0.65 mmol) was added and the clear biphasic solution stirred at room temperature for 3 h. The mixture was diluted with $Et_2O$ (20 mL) and water (5 mL) and the layers were separated. The aqueous layer was washed with $Et_2O$. The aqueous layer was lyophilized and purified by ion exchange chromatography (PoraPak Rxn CX 20 cc column). The desired product was eluted from the column using 5% ammonia in MeOH (20 mL). The obtained material was further purified by reverse phase chromatography (RediSep Rf Gold® C18, 0 to 15% acetonitrile in water) to afford (2R,4S)-4-[[(2S)-2-aminopropanoyl]amino]-2-(4-boronobutyl)piperidine-2-carboxylic acid (Example 4, 25 mg, 37% yield) as a white solid. $^1$H NMR (500 MHz, $D_2O$) δ 0.72-0.80 (2H, m), 1.12-1.23 (1H, m), 1.24-1.26 (1H, m), 1.27 (3H, d), 1.40 (2H, quin), 1.66-1.76 (1H, m), 1.78-1.92 (2H, m), 1.93-1.99 (1H, m), 2.00-2.06 (1H, m), 2.10 (1H, dd), 3.18 (1H, ddd), 3.27-3.36 (1H, m), 3.53 (1H, q), 4.10 (1H, tt); m/z: (ES$^+$) [M+H]$^+$=316.

Example 5: (2R,4 S)-4-[[(2S)-2-aminobutanoyl]amino]-2-(4-boronobutyl)piperidine-2-carboxylic acid

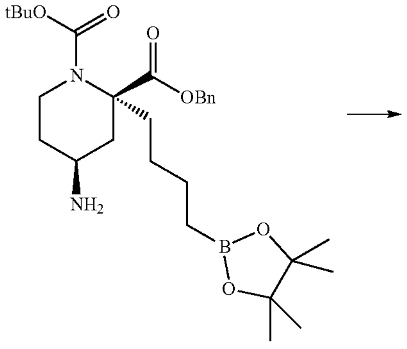

Intermediate 8

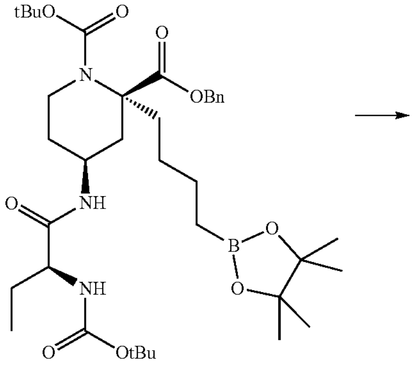

Intermediate 15

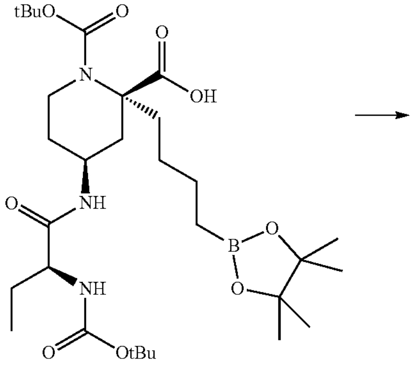

Intermediate 16

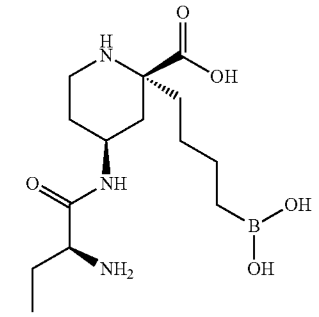

Example 5

Intermediate 15: 2-benzyl 1-(tert-butyl) (2R,4S)-4-((S)-2-((tert-butoxycarbonyl)amino)butanamido)-2-(4-(4, 4,5, 5-tetra methyl-1,3,2-dioxaborolan-2-yl) butyl)piperidine-1,2-dicarboxylate N,N-Diisopropylethylamine (0.165 mL, 0.94 mmol) was added slowly to a stirred solution of 2-benzyl 1-(tert-butyl) (2R,4S)-4-amino-2-(4-(4,4,5,5-tetramethyl-1,3,2-dioxaborolan-2-yl)butyl)piperidine-1,2-dicarboxylate (Intermediate 8, 244 mg, 0.47 mmol), Boc-Abu-OH (96 mg, 0.47 mmol) and COMU (206 mg, 0.48 mmol) in DMF (3 mL) at 0° C. The reaction stirred for 16 h while slowly warming to room temperature. The crude reaction mixture was diluted with water (30 mL) and extracted with EtOAc (3×10 mL). The combined organics were washed sequentially with saturated aqueous $NaHCO_3$ (20 mL) and saturated aqueous NaCl (15 mL). The organic layer was dried over $MgSO_4$, filtered and concentrated to dryness. The resulting residue was purified by flash silica chromatography (15 to 60% EtOAc in hexanes) to afford 2-benzyl 1-(tert-butyl) (2R,4S)-4-((S)-2-((tert-butoxycarbonyl)amino)butanamido)-2-(4-(4,4,5,5-tetramethyl-1,3,2-dioxaborolan-2-yl)butyl)piperidine-1,2-dicarboxylate (Intermediate 15, 215 mg, 65% yield) as clear gum and as a mixture of rotamers. $^1$H NMR (500 MHz, $CDCl_3$) δ 0.71-0.79 (2H, m), 0.87 (3H, br t), 1.19 (4H, br s), 1.21 (9H, s), 1.36 (5H, br s), 1.38 (8H, s), 1.39-1.41 (8H, m), 1.48-1.58 (2H, m), 1.68 (1H, br dd), 1.72-1.81 (1H, m), 1.84-1.98 (3H, m), 1.99-2.02 (1H, m), 2.88-3.04 (1H, m), 3.89 (1H, br d), 3.95-4.07 (2H, m), 5.00 (1H, br d), 5.05-5.22 (2H, m), 6.20 (1H, br s), 7.27-7.36 (5H, m); m/z: ($ES^+$) $[M+H]^+$=703.

Intermediate 16: (2R,4S)-1-(tert-butoxycarbonyl)-4-((S)-2-((tert-butoxycarbonyl)amino)butanamido)-2-(4-(4,4,5,5-tetramethyl-1,3,2-dioxaborolan-2-yl) butyl)piperidine-2-carboxylic acid Pd/C (10% wt, 16 mg, 0.015 mmol) was added to a solution of 2-benzyl 1-(tert-butyl) (2R,4S)-4-((S)-2-((tert-butoxycarbonyl)amino)butanamido)-2-(4-(4,4,5,5-tetramethyl-1,3,2-dioxaborolan-2-yl)butyl)piperidine-1,2-dicarboxylate (Intermediate 15, 215 mg, 0.31 mmol) in EtOAc (3 mL). The suspension was stirred under a hydrogen atmosphere (balloon, flask evacuated and back-filled with hydrogen ×3) at room temperature for 24 h. The reaction mixture was diluted with EtOAc (10 mL) and MeOH (1 mL), filtered through diatomaceous earth and concentrated to dryness. The resulting residue was purified by flash silica chromatography (5 to 100% EtOAc in hexanes) to afford (2R,4S)-1-(tert-butoxycarbonyl)-4-((S)-2-((tert-butoxycarbonyl) amino)butanamido)-2-(4-(4,4,5,5-tetramethyl-1,3,2-dioxaborolan-2-yl)butyl)piperidine-2-carboxylic acid (Intermediate 16, 147 mg, 78% yield) as a dry film and a mixture of rotamers. $^1$H NMR (500 MHz, $CDCl_3$) δ 0.75 (2H, br s), 0.89 (3H, br s), 1.20 (12H, s), 1.24-1.33 (2H, m), 1.37 (10H, br s), 1.40 (10H, s), 1.42-1.61 (4H, m), 1.85 (3H, br s), 1.98 (2H, br s), 2.01-2.06 (1H, m), 2.95 (1H, br s), 3.98 (2H, br s), 5.27 (0.5H, br s), 5.68 (0.5H, br s), 6.74 (0.5H, br s), 7.52 (0.5H, br s); m/z: ($ES^+$) $[M+H]^+$=612.

Example 5: (2R,4S)-4-[[(2S)-2-aminobutanoyl] amino]-2-(4-boronobutyl)piperidine-2-carboxylic acid Trifluoroacetic acid (0.37 mL, 4.8 mmol) was added dropwise to a stirred solution of (2R,4S)-1-(tert-butoxycarbonyl)-4-((S)-2-((tert-butoxycarbonyl)amino)butanamido)-2-(4-(4,4,5,5-tetramethyl-1,3,2-dioxaborolan-2-yl)butyl)piperidine-2-carboxylic acid (Intermediate 16, 147 mg, 0.24 mmol) in DCM (1 mL) at room temperature. After 2 h the solution was concentrated under reduced pressure and the resulting residue was dissolved in 1 M HCl (aq) (2.0 mL, 2.0 mmol) and $Et_2O$ (2 mL). Phenylboronic acid (88 mg, 0.72 mmol) was added and the clear biphasic solution stirred at room temperature for 4 h. The mixture was diluted with $Et_2O$ (5 mL) and water (2 mL) and the layers were separated. The aqueous layer was washed with $Et_2O$. The aqueous layer was lyophilized and purified by ion exchange chromatography (PoraPak Rxn CX 20 cc column). The desired product was eluted from the column using 5% ammonia in MeOH (20 mL). The obtained material was further purified by reverse phase chromatography (RediSep Rf Gold® C18, 0 to 15% acetonitrile in water) to afford (2R,4S)-4-[[(2S)-2-aminobutanoyl]amino]-2-(4-boronobutyl)piperidine-2-carboxylic acid (Example 5, 37 mg, 47% yield) as a white solid. $^1$H NMR (500 MHz, $D_2O$) δ 0.76 (2H, br t), 0.87 (3H, t), 1.13-1.23 (1H, m), 1.24-1.34 (1H, m), 1.40 (2H, quin), 1.63 (2H, dq), 1.67-1.74 (1H, m), 1.78-1.85 (1H, m), 1.86-1.96 (2H, m), 1.99-2.07 (1H, m), 2.13 (1H, br dd), 3.10-3.24 (1H, m), 3.25-3.41 (2H, m), 4.07-4.21 (1H, m); m/z: ($ES^+$) $[M+H]^+$=330.

Example 6: (2R,4S)-4[[(2S)-2-amino-4-methyl-pentanoyl]amino]-2-(4-boronobutyl)piperidine-2-carboxylic acid

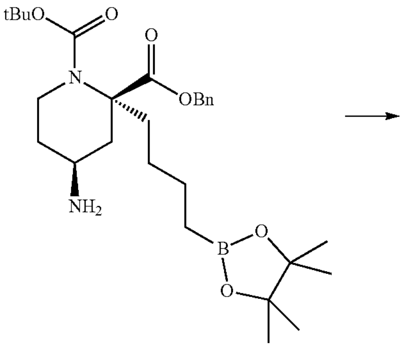

Intermediate 8

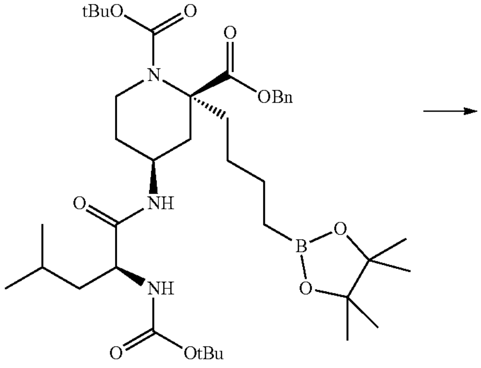

Intermediate 17

-continued

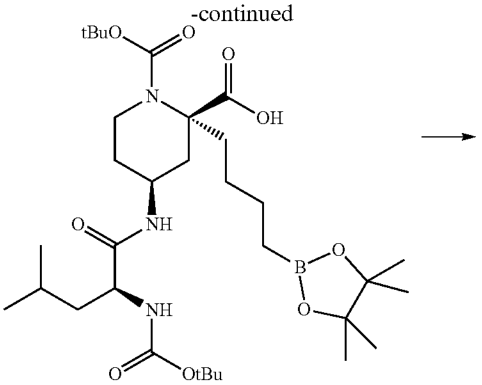

Intermediate 18

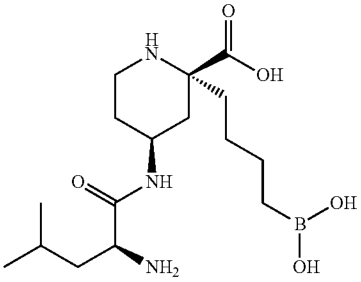

Example 6

Intermediate 17: 2-benzyl 1-(tert-butyl) (2R,4S)-4-((S)-2-((tert-butoxycarbonyl)amino)-4-methylpentanamido)-2-(4-(4,4,5,5-tetramethyl-1,3,2-dioxaborolan-2-yl)butyl)piperidine-1,2-dicarboxylate N,N-Diisopropylethylamine (0.17 mL, 0.94 mmol) was added to a stirred solution of 2-benzyl 1-(tert-butyl) (2R,4S)-4-amino-2-(4-(4,4,5,5-tetramethyl-1,3,2-dioxaborolan-2-yl)butyl)piperidine-1,2-dicarboxylate (Intermediate 8, 244 mg, 0.47 mmol), Boc-Leu-OH (96 mg, 0.47 mmol) and COMU (206 mg, 0.48 mmol) in DMF (3 mL) at 0° C. The reaction stirred for 16 h while slowly warming to room temperature. The crude reaction mixture was diluted with water (30 mL) and extracted with EtOAc (3×10 mL). The combined organics were washed sequentially with saturated aqueous $NaHCO_3$ (20 mL) and saturated aqueous NaCl (15 mL). The organic layer was dried over $MgSO_4$, filtered and concentrated to dryness. The resulting residue was purified by flash silica chromatography (15 to 60% EtOAc in hexanes) to afford 2-benzyl 1-(tert-butyl) (2R,4S)-4-((S)-2-((tert-butoxycarbonyl)amino)-4-methylpentanamido)-2-(4-(4,4,5,5-tetramethyl-1,3,2-dioxaborolan-2-yl)butyl)piperidine-1,2-dicarboxylate (Intermediate 17, 224 mg, 65% yield) as a white foam and as a mixture of rotamers. $^1H$ NMR (500 MHz, $CDCl_3$) δ 0.73-0.80 (2H, m), 0.89 (3H, d), 0.90 (3H, d), 1.22 (12H, s), 1.27 (1H, br s), 1.39 (9H, s), 1.40 (9H, s), 1.41-1.48 (4H, m), 1.55-1.64 (2H, m), 1.68 (1H, br dd), 1.85-1.98 (3H, m), 2.01 (1H, br d), 2.02-2.05 (1H, m), 2.93-3.02 (1H, m), 3.94-4.08 (3H, m), 4.83 (1H, br d), 5.05-5.22 (2H, m), 6.20 (1H, br s), 7.28-7.31 (1H, m), 7.33 (4H, d); m/z: ($ES^+$) $[M+H]^+$=731.

Intermediate 18: (2R,4S)-1-(tert-butoxycarbonyl)-4-((S)-2-((tert-butoxycarbonyl)amino)-4-methylpentanamido)-2-(4-(4,4,5,5-tetramethyl-1,3,2-dioxaborolan-2-yl)butyl)piperidine-2-carboxylic acid Pd/C (10% wt, 13 mg, 0.012 mmol) was added to a solution of 2-benzyl 1-(tert-butyl) (2R,4S)-4-((S)-2-((tert-butoxycarbonyl)amino)-4-methylpentanamido)-2-(4-(4,4,5,5-tetramethyl-1,3,2-dioxaborolan-2-yl)butyl)piperidine-1,2-dicarboxylate (Intermediate 17, 174 mg, 0.24 mmol) in EtOAc (2.5 mL). The suspension was stirred under a hydrogen atmosphere (balloon, flask evacuated and back-filled with hydrogen ×3) at room temperature for 23 h. The reaction mixture was diluted with EtOAc (10 mL) and MeOH (1 mL), filtered through diatomaceous earth and concentrated to dryness. The resulting residue was purified by flash silica chromatography (15 to 100% EtOAc in hexanes) to afford (2R,4S)-1-(tert-butoxycarbonyl)-4-((S)-2-((tert-butoxycarbonyl)amino)-4-methylpentanamido)-2-(4-(4,4,5,5-tetramethyl-1,3,2-dioxaborolan-2-yl)butyl)piperidine-2-carboxylic acid (Intermediate 18, 149 mg, 98% yield) as a dry film and a mixture of rotamers. $^1H$ NMR (500 MHz, $CDCl_3$) δ 0.78 (2H, br t), 0.91 (6H, br d), 1.23 (11H, s), 1.27-1.36 (2H, m), 1.40 (10H, s), 1.43 (11H, s), 1.46-1.55 (2H, m), 1.60-1.73 (2H, m), 1.78-1.96 (3H, m), 1.97-2.02 (1H, m), 2.05-2.14 (1H, m), 2.82-3.08 (1H, m), 3.92-4.08 (2H, m), 5.00 (0.4H, br s), 5.49 (0.6H, br d), 6.76 (0.4H, br d), 7.60 (0.6H, br s); m/z: ($ES^+$) $[M+H]^+$=640.

Example 6: (2R,4S)-4-[[(2S)-2-amino-4-methylpentanoyl]amino]-2-(4-boronobutyl)piperidine-2-carboxylic acid Trifluoroacetic acid (0.36 mL, 4.7 mmol) was added dropwise to a stirred solution of (2R,4S)-1-(tert-butoxycarbonyl)-4-((S)-2-((tert-butoxycarbonyl)amino)-4-methylpentanamido)-2-(4-(4,4,5,5-tetramethyl-1,3,2-dioxaborolan-2-yl)butyl)piperidine-2-carboxylic acid (Intermediate 18, 149 mg, 0.23 mmol) in DCM (1 mL) at room temperature. After 2 h the solution was concentrated under reduced pressure and the resulting residue was dissolved in 1 M HCl (aq) (2.0 mL, 2.0 mmol) and $Et_2O$ (2 mL). Phenylboronic acid (85 mg, 0.70 mmol) was added and the clear biphasic solution stirred at room temperature for 4 h. The mixture was diluted with $Et_2O$ (10 mL) and water (2 mL) and the layers were separated. The aqueous layer was washed with $Et_2O$. The aqueous layer was lyophilized and purified by ion exchange chromatography (PoraPak Rxn CX 20 cc column). The desired product was eluted from the column using 5% ammonia in MeOH (20 mL) to afford (2R,4S)-4-[[(2S)-2-amino-4-methyl-pentanoyl]amino]-2-(4-boronobutyl)piperidine-2-carboxylic acid (Example 6, 81 mg, 97% yield) as a white solid. $^1H$ NMR (500 MHz, $D_2O$) δ 0.74-0.82 (2H, m), 0.89 (3H, d), 0.91 (3H, d), 1.15-1.25 (1H, m), 1.24-1.34 (1H, m), 1.38-1.47 (3H, m), 1.47-1.54 (1H, m), 1.60 (1H, dt), 1.65-1.76 (1H, m), 1.79-1.98 (3H, m), 2.01-2.09 (1H, m), 2.14 (1H, dd), 3.15-3.23 (1H, m), 3.31 (1H, dt), 3.39 (1H, t), 4.10-4.17 (1H, m); m/z: ($ES^+$) $[M-H_2O+H]^+$=340.

Example 7: (2R,4S)-4-[[(2S,3S)-2-amino-3-methylpentanoyl]amino]-2-(4-boronobutyl)piperidine-2-carboxylic acid

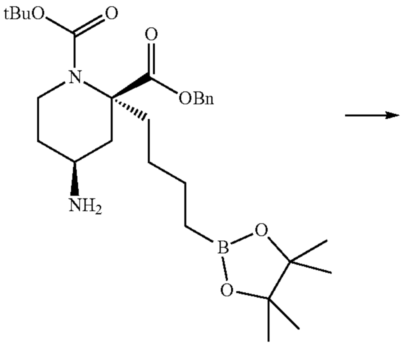

Intermediate 8

-continued

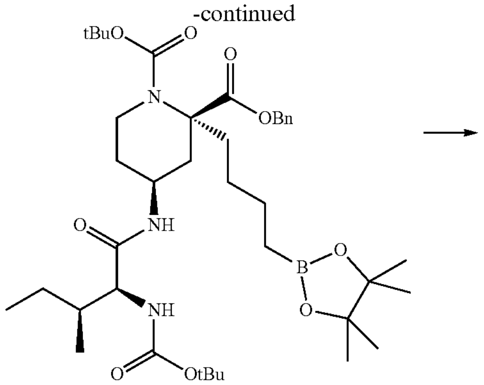

Intermediate 19

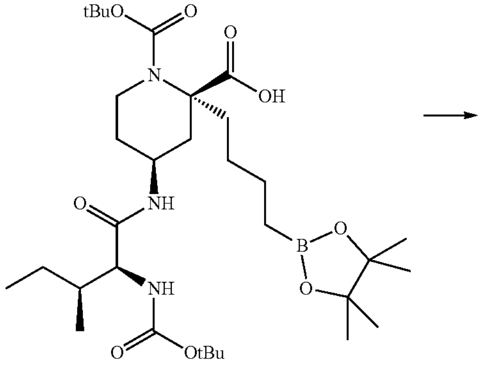

Intermediate 20

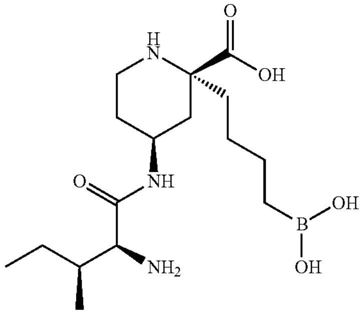

Example 7

Intermediate 19: 2-benzyl 1-(tert-butyl) (2R,4S)-4-((2S,3S)-2-((tert-butoxycarbonyl)amino)-3-methylpentanamido)-2-(4-(4,4,5,5-tetramethyl-1,3,2-dioxaborolan-2-yl)butyl)piperidine-1,2-dicarboxylate N,N-Diisopropylethylamine (0.24 mL, 1.4 mmol) was added slowly to a stirred solution of 2-benzyl 1-(tert-butyl) (2R,4S)-4-amino-2-(4-(4,4,5,5-tetramethyl-1,3,2-dioxaborolan-2-yl)butyl)piperidine-1,2-dicarboxylate (Intermediate 8, 355 mg, 0.687 mmol), Boc-Ile-OH (159 mg, 0.687 mmol) and COMU (300 mg, 0.70 mmol) in DMF (4 mL) at 0° C. The reaction stirred for 16 h while slowly warming to room temperature. The crude reaction mixture was diluted with water (30 mL) and the mixture stirred for 10 min. The resulting precipitate was collected by filtration. The solid was dissolved in EtOAc (20 mL) and washed with saturated aqueous NaCl (5 mL), dried over $MgSO_4$, filtered and concentrated to dryness. The resulting residue was purified by flash silica chromatography (5 to 60% EtOAc in hexanes) to afford 2-benzyl 1-(tert-butyl) (2R,4S)-4-((2S,3S)-2-((tert-butoxycarbonyl)amino)-3-methylpentanamido)-2-(4-(4,4,5,5-tetramethyl-1,3,2-dioxaborolan-2-yl)butyl)piperidine-1,2-dicarboxylate (Intermediate 19, 424 mg, 85% yield) as a white foam and as a mixture of rotamers. $^1H$ NMR (500 MHz, $CDCl_3$) δ 0.73-0.80 (2H, m), 0.82-0.90 (6H, m), 0.97-1.11 (1H, m), 1.21 (12H, s), 1.26-1.31 (1H, m), 1.32-1.36 (1H, m), 1.38 (9H, br s), 1.39 (9H, s), 1.41-1.43 (2H, m), 1.67 (1H, br dd), 1.75-1.84 (2H, m), 1.86-1.98 (3H, m), 2.00 (1H, br d), 2.03 (1H, br d), 2.92-3.02 (1H, m), 3.81 (1H, t), 3.95-4.09 (2H, m), 4.98 (1H, br s), 5.04-5.21 (2H, m), 6.07 (1H, br d), 7.28-7.36 (5H, m); m/z: $(ES^+)$ $[M+H]^+$=730.

Intermediate 20: (2R,4S)-1-(tert-butoxycarbonyl)-4-((2S,3S)-2-((tert-butoxycarbonyl)amino)-3-methylpentanamido)-2-(4-(4,4,5,5-tetramethyl-1,3,2-dioxaborolan-2-yl)butyl)piperidine-2-carboxylic acid Pd/C (10% wt, 22 mg, 0.021 mmol) was added to a solution of 2-benzyl 1-(tert-butyl) (2R,4S)-4-((2S,3S)-2-((tert-butoxycarbonyl)amino)-3-methylpentanamido)-2-(4-(4,4,5,5-tetramethyl-1,3,2-dioxaborolan-2-yl)butyl)piperidine-1,2-dicarboxylate (Intermediate 19, 302 mg, 0.41 mmol) in EtOAc (4 mL). The suspension was stirred under a hydrogen atmosphere (balloon, flask evacuated and back-filled with hydrogen ×3) at room temperature for 20 h. The reaction mixture was diluted with EtOAc (10 mL) and MeOH (1 mL), filtered through diatomaceous earth and concentrated to dryness. The resulting residue was purified by flash silica chromatography (15 to 100% EtOAc in hexanes followed by 0 to 50% MeOH in EtOAc) to afford (2R,4S)-1-(tert-butoxycarbonyl)-4-((2S,3S)-2-((tert-butoxycarbonyl)amino)-3-methylpentanamido)-2-(4-(4,4,5,5-tetramethyl-1,3,2-dioxaborolan-2-yl)butyl)piperidine-2-carboxylic acid (Intermediate 20, 223 mg, 84% yield) as a dry film and as a mixture of rotamers, and the boronic acid byproduct (2R,4S)-2-(4-boronobutyl)-1-(tert-butoxycarbonyl)-4-((2S,3S)-2-((tert-butoxycarbonyl)amino)-3-methylpentanamido)piperidine-2-carboxylic acid (30 mg, 13% yield) as a white solid and as a mixture or rotamers. Intermediate 20: $^1H$ NMR (500 MHz, $CDCl_3$) δ 0.72-0.81 (2H, m), 0.82-0.88 (3H, m), 0.89-0.94 (3H, m), 0.98-1.11 (1H, m), 1.21-1.24 (12H, m), 1.26-1.31 (1H, m), 1.32-1.38 (2H, m), 1.40 (10H, br s), 1.42 (10H, br s), 1.45-1.55 (1H, m), 1.53-1.64 (1H, m), 1.76-1.97 (4H, m), 1.98-2.08 (3H, m), 2.83-3.10 (1H, m), 3.90-4.08 (2H, m), 5.15 (0.5H, br d), 5.81 (0.5H, br s), 6.74 (0.5H, br s), 7.48 (0.5H, br s); m/z: $(ES^+)$ $[M+H]^+$=640. Boronic acid byproduct: $^1H$ NMR (500 MHz, $CDCl_3$) δ 0.76-0.86 (2H, m), 0.86-0.96 (6H, m), 1.03-1.13 (1H, m), 1.43 (9H, br s), 1.44 (12H, s), 1.53-1.68 (1H, m), 1.78-1.90 (2H, m), 1.90-1.99 (2H, m), 1.99-2.04 (1H, m), 2.07-2.21 (1H, m), 2.98-3.11 (1H, m), 3.43-3.61 (1H, m), 3.90 (1H, br s), 3.96-4.12 (2H, m), 5.19 (1H, br s), 5.53-5.76 (1H, m), 6.72 (1H, br s); m/z: $(ES^+)$ $[M+H]^+$=558.

Example 7: (2R,4S)-4-[[(2S,3S)-2-amino-3-methylpentanoyl]amino]-2-(4-boronobutyl)piperidine-2-carboxylic acid Trifluoroacetic acid (0.62 mL, 8.1 mmol) was added dropwise to a stirred solution of (2R,4S)-1-(tert-butoxycarbonyl)-4-((2S,3S)-2-((tert-butoxycarbonyl)amino)-3-methylpentanamido)-2-(4-(4,4,5,5-tetramethyl-1,3,2-dioxaborolan-2-yl)butyl)piperidine-2-carboxylic acid (Intermediate 20, 223 mg, 0.35 mmol) and the boronic acid byproduct (2R,4S)-2-(4-boronobutyl)-1-(tert-butoxycarbonyl)-4-((2S,3S)-2-((tert-butoxycarbonyl)amino)-3-methylpentanamido) piperidine-2-carboxylic acid (30 mg, 0.05 mmol) in DCM (2 mL) at room temperature. After 2 h the solution was concentrated under reduced pressure and the resulting residue was dissolved in 1 M HCl (aq) (3.0 mL, 3.0 mmol) and $Et_2O$ (3 mL). Phenylboronic acid (147 mg, 1.21 mmol) was added and the clear biphasic solution stirred at room temperature for 3 h. The mixture was diluted with $Et_2O$ (5 mL) and water (1 mL) and the layers were separated. The aqueous layer was washed with $Et_2O$. The aqueous layer was lyophilized and purified by ion exchange chromatography (PoraPak Rxn CX 20 cc column). The desired product was eluted from the column using 5% ammonia in MeOH (20 mL) to afford (2R,4S)-4-[[(2S,3S)-2-amino-3-methyl-pentanoyl]amino]-2-(4-boronobutyl)piperidine-2-carboxylic acid (Example 7, 126 mg, 88% yield) as a white solid. $^1H$ NMR (500 MHz, $D_2O$) δ 0.78 (2H, td), 0.85-0.91 (6H, m), 1.11-1.25 (2H, m), 1.26-1.34 (1H, m), 1.37-1.49 (3H, m), 1.64-1.76 (2H, m), 1.80-1.91 (2H, m), 1.92-1.99 (1H, m), 2.01-2.09 (1H, m), 2.17 (1H, dd), 3.15-3.24 (2H, m), 3.31 (1H, dt), 4.10-4.21 (1H, m); m/z: ($ES^+$) $[M+H]^+$=358.

Example 8: (2R,4S)-4-[[(2S)-2-amino-3,3-dimethyl-butanoyl]amino]-2-(4-boronobutyl)piperidine-2-carboxylic acid

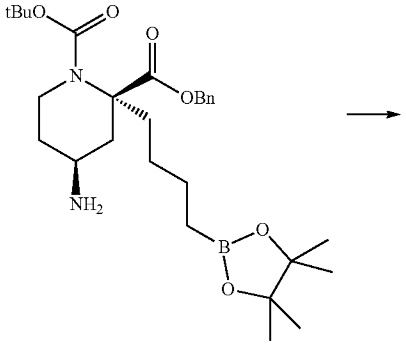

Intermediate 8

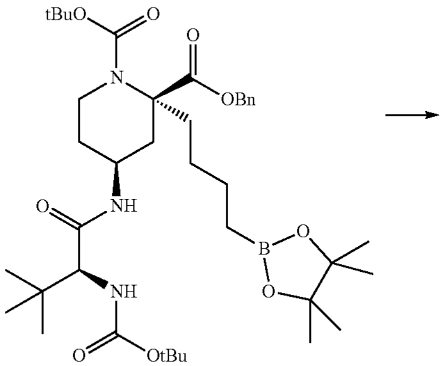

Intermediate 21

-continued

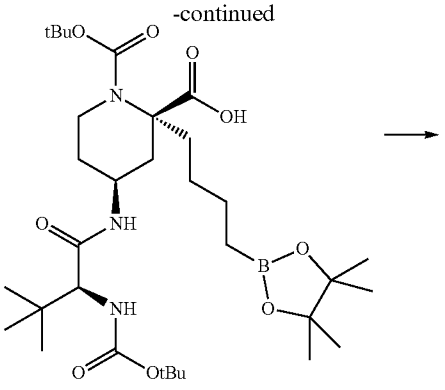

Intermediate 22

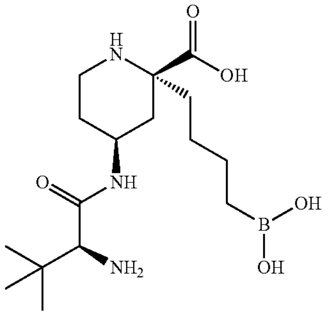

Example 8

Intermediate 21: 2-benzyl 1-(tert-butyl) (2R,4S)-4-((S)-2-((tert-butoxycarbonyl)amino)-3,3-dimethylbutanamido)-2-(4-(4,4,5,5-tetramethyl-1,3,2-dioxaborolan-2-yl)butyl)piperidine-1,2-dicarboxylate N,N-Diisopropylethylamine (0.24 mL, 1.4 mmol) was added slowly to a stirred solution of 2-benzyl 1-(tert-butyl) (2R,4S)-4-amino-2-(4-(4,4,5,5-tetramethyl-1,3,2-dioxaborolan-2-yl)butyl)piperidine-1,2-dicarboxylate (Intermediate 8, 355 mg, 0.687 mmol), Boc-ted-Leu-OH (159 mg, 0.687 mmol) and COMU (300 mg, 0.70 mmol) in DMF (4 mL) at 0° C. The reaction stirred for 16 h while slowly warming to room temperature. The crude reaction mixture was diluted with water (30 mL) and the mixture stirred for 10 min. The resulting precipitate was collected by filtration. The solid was dissolved in EtOAc (20 mL) and washed with saturated aqueous NaCl (5 mL), dried over $MgSO_4$, filtered and concentrated to dryness. The resulting residue was purified by flash silica chromatography (5 to 55% EtOAc in hexanes) to afford 2-benzyl 1-(tert-butyl) (2R,4S)-4-((S)-2-((tert-butoxycarbonyl)amino)-3,3-dimethylbutanamido)-2-(4-(4,4,5,5-tetramethyl-1,3,2-dioxaborolan-2-yl)butyl)piperidine-1,2-dicarboxylate (Intermediate 21, 372 mg, 74% yield) as a white foam. $^1H$ NMR (500 MHz, $CDCl_3$) δ 0.73-0.81 (2H, m), 0.95 (9H, s), 1.24 (12H, s), 1.41 (10H, s), 1.42-1.46 (12H, m), 1.68 (1H, dd), 1.87-1.95 (1H, m), 1.96-2.01 (2H, m), 2.02-2.05 (2H, m), 2.92-3.04 (1H, m), 3.69 (1H, br d), 3.98-4.12 (2H, m), 5.05-5.25 (3H, m), 5.50-5.62 (1H, m), 7.30-7.39 (5H, m); m/z: ($ES^+$) $[M+H]^+$ =730.

Intermediate 22: (2R,48)-1-(tert-butoxycarbonyl)-4-((S)-2-((tert-butoxycarbonyl)amino)-3,3-dimethylbutanamido)-2-(4-(4,4,5,5-tetramethyl-1,3,2-dioxaborolan-2-yl)butyl)piperidine-2-carboxylic acid Pd/C (10% wt, 27 mg, 0.025 mmol) was added to a solution of 2-benzyl 1-(tert-butyl) (2R,4S)-4-((S)-2-((tert-butoxycarbonyl)amino)-3,3-dimethylbutanamido)-2-(4-(4,4,5,5-tetramethyl-1,3,2-dioxaborolan-2-yl)butyl)piperidine-1,2-dicarboxylate (Intermediate 21, 372 mg, 0.511 mmol) in EtOAc (4 mL). The suspension was stirred under a hydrogen atmosphere (balloon, flask evacuated and back-filled with hydrogen ×3) at room temperature for 20 h. The reaction mixture was diluted with EtOAc (10 mL) and MeOH (1 mL), filtered through diatomaceous earth and concentrated to dryness. The resulting residue was purified by flash silica chromatography (40 to 100% EtOAc in hexanes followed by 0 to 40% MeOH in EtOAc) to afford (2R,4S)-1-(tert-butoxycarbonyl)-4-((S)-2-((tert-butoxycarbonyl)amino)-3,3-dimethylbutanamido)-2-(4-(4,4,5,5-tetramethyl-1,3,2-dioxaborolan-2-yl)butyl)piperidine-2-carboxylic acid (Intermediate 22, 265 mg, 81% yield) as a dry film and a mixture of rotamers, and the boronic acid byproduct (2R,4S)-2-(4-boronobutyl)-1-(tert-butoxycarbonyl)-4-((S)-2-((tert-butoxycarbonyl)amino)-3,3-dimethylbutanamido)piperidine-2-carboxylic acid (32 mg, 11% yield) as a clear dry film and as a mixture of rotamers. Intermediate 22: $^1$H NMR (500 MHz, $CDCl_3$) δ 0.75 (2H, br t), 0.93 (9H, s), 1.20 (12H, s), 1.24-1.33 (2H, m), 1.36 (9H, s), 1.38 (9H, br s), 1.40 (3H, br s), 1.51-1.64 (1H, m), 1.72-1.82 (1H, m), 1.83-1.98 (3H, m), 2.03 (1H, br s), 2.79-3.06 (1H, m), 3.76 (0.4H, br d), 3.85-4.07 (2.6H, m), 5.42 (0.6H, br d), 6.39-6.71 (1H, m), 6.74-6.99 (0.4H, m); m/z: ($ES^+$) $[M+H]^+$=640. Boronic acid byproduct: $^1$H NMR (500 MHz, $CDCl_3$) δ 0.77-0.86 (2H, m), 0.97 (9H, s), 1.42 (9H, br s), 1.43 (14H, br s), 1.52-1.67 (1H, m), 1.75-1.90 (2H, m), 1.91-2.04 (3H, m), 2.08-2.19 (1H, m), 2.97-3.14 (1H, m), 3.44-3.63 (1H, m), 3.87 (1H, br d), 3.97-4.11 (2H, m), 5.50 (1H, br s), 6.53-6.79 (1H, m); m/z: ($ES^+$) $[M+H]^+$=558.

Example 8: (2R,48)-4-[[(28)-2-amino-3,3-dimethylbutanoyl]amino]-2-(4-boronobutyl)piperidine-2-carboxylic acid Trifluoroacetic acid (0.73 mL, 9.4 mmol) was added dropwise to a stirred solution of (2R,4S)-1-(tert-butoxycarbonyl)-4-((S)-2-((tert-butoxycarbonyl)amino)-3,3-dimethylbutanamido)-2-(4-(4,4,5,5-tetramethyl-1,3,2-dioxaborolan-2-yl)butyl)piperidine-2-carboxylic acid (Intermediate 22, 265 mg, 0.414 mmol) and the boronic acid byproduct (2R,4S)-2-(4-boronobutyl)-1-(tert-butoxycarbonyl)-4-((S)-2-((tert-butoxycarbonyl)amino)-3,3-dimethylbutanamido) piperidine-2-carboxylic acid (32 mg, 0.057 mmol) in DCM (2 mL) at room temperature. After 2 h the solution was concentrated under reduced pressure and the resulting residue was dissolved in 1 M HCl (aq) (3.0 mL, 3.0 mmol) and $Et_2O$ (3 mL). Phenylboronic acid (172 mg, 1.41 mmol) was added and the clear biphasic solution stirred at room temperature for 4 h. The mixture was diluted with $Et_2O$ (5 mL) and water (1 mL) and the layers were separated. The aqueous layer was washed with $Et_2O$. The aqueous layer was lyophilized and purified by ion exchange chromatography (PoraPak Rxn CX 20 cc column). The desired product was eluted from the column using 5% ammonia in MeOH (20 mL) to afford (2R,4S)-4-[[(2S)-2-amino-3,3-dimethylbutanoyl]amino]-2-(4-boronobutyl)piperidine-2-carboxylic acid (Example 8, 158 mg, 94% yield) as a white solid. $^1$H NMR (500 MHz, $D_2O$) δ 0.74-0.81 (2H, m), 0.95 (9H, s), 1.15-1.25 (1H, m), 1.26-1.34 (1H, m), 1.38-1.48 (2H, m), 1.65-1.75 (1H, m), 1.80-1.91 (2H, m), 1.96 (1H, ddd), 2.01-2.10 (1H, m), 2.19 (1H, dd), 3.05 (1H, s), 3.15-3.24 (1H, m), 3.30 (1H, dt), 4.10-4.23 (1H, m); m/z: ($ES^+$) $[M+H]^+$=358.

Example 9: (2R,4S)-4-[[(2R)-2-amino-3-methylbutanoyl]amino]-2-(4-boronobutyl)piperidine-2-carboxylic acid

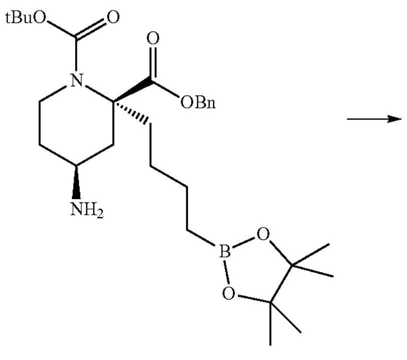

Intermediate 8

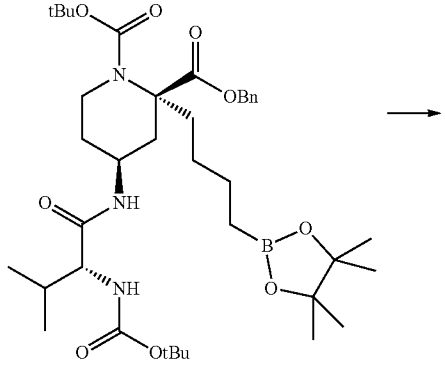

Intermediate 23

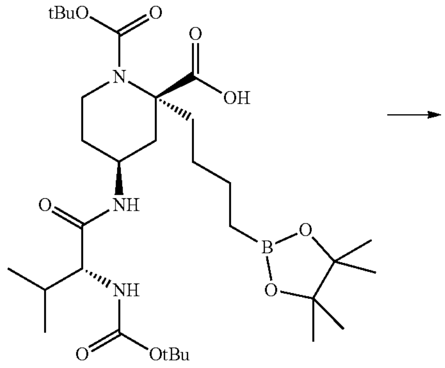

Intermediate 24

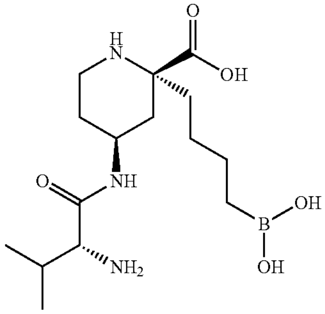

Example 9

Intermediate 23: 2-benzyl 1-(tert-butyl) (2R,4S)-4-((R)-2-((tert-butoxycarbonyl)amino)-3-methylbutanamido)-2-(4-(4,4,5,5-tetramethyl-1,3,2-dioxaborolan-2-yl)butyl)piperidine-1,2-dicarboxylate N,N-Diisopropylethylamine (0.063 mL, 0.36 mmol) was added slowly to a stirred solution of HATU (61 mg, 0.16 mmol) and Boc-D-Val-OH (33 mg, 0.15 mmol) in DMF (1 mL) at 0° C. The solution was stirred for 10 min then a solution of 2-benzyl 1-(tert-butyl) (2R,4S)-4-amino-2-(4-(4,4,5,5-tetramethyl-1,3,2-dioxaborolan-2-yl)butyl)piperidine-1,2-dicarboxylate (Intermediate 8, 75 mg, 0.15 mmol) in DMF (1 mL) was added. The reaction stirred for 16 h while slowly warming to room temperature. The crude reaction was diluted with 0.1 M HCl (aq) (30 mL) and EtOAc. The phases were separated and the aqueous phase was extracted with EtOAc (3×15 mL). The combined organics were washed with saturated aqueous NaCl, dried over $MgSO_4$, filtered and concentrated to dryness. The resulting residue was purified by flash silica chromatography (5 to 40% EtOAc in hexanes) to afford 2-benzyl 1-(tert-butyl) (2R,4S)-4-((R)-2-((tert-butoxycarbonyl)amino)-3-methylbutanamido)-2-(4-(4,4,5,5-tetramethyl-1,3,2-dioxaborolan-2-yl)butyl)piperidine-1,2-dicarboxylate (Intermediate 23, 74 mg, 71% yield) as a colorless film and as a mixture of rotamers. $^1$H NMR (500 MHz, $CDCl_3$) δ 0.75 (2H, t), 0.84 (3H, d), 0.89 (3H, d), 1.21 (12H, s), 1.30-1.35 (1H, m), 1.37 (9H, s), 1.39 (9H, s), 1.42 (4H, br s), 1.69 (1H, dd), 1.81-1.91 (1H, m), 1.92-2.01 (3H, m), 2.02 (2H, s), 2.94-3.02 (1H, m), 3.75 (1H, dd), 3.91-4.03 (1H, m), 5.03-5.19 (3H, m), 6.10 (1H, d), 7.28-7.39 (5H, m); m/z: ($ES^+$) $[M+H]^+$=715.

Intermediate 24: (2R,4S)-1-(tert-butoxycarbonyl)-4-((R)-2-((tert-butoxycarbonyl)amino)-3-methylbutanamido)-2-(4-(4,4,5,5-tetramethyl-1,3,2-dioxaborolan-2-yl)butyl)piperidine-2-carboxylic acid Pd/C (10% wt, 5 mg, 0.005 mmol) was added to a solution of 2-benzyl 1-(tert-butyl) (2R,4S)-4-((R)-2-((tert-butoxycarbonyl)amino)-3-methylbutanamido)-2-(4-(4,4,5,5-tetramethyl-1,3,2-dioxaborolan-2-yl)butyl)piperidine-1,2-dicarboxylate (Intermediate 23, 69 mg, 0.10 mmol) in EtOAc (1 mL). The suspension was stirred under a hydrogen atmosphere (balloon, flask evacuated and back-filled with hydrogen ×3) at room temperature for 19 h. The reaction mixture was diluted with EtOAc (10 mL) and MeOH (1 mL), filtered through diatomaceous earth and concentrated to dryness. The resulting residue was purified by flash silica chromatography (40 to 100% EtOAc in hexanes then 0 to 40% MeOH in EtOAc) to afford (2R,4S)-1-(tert-butoxycarbonyl)-4(R)-2-((tert-butoxycarbonyl)amino)-3-methylbutanamido)-2-(4-(4,4,5,5-tetramethyl-1,3,2-dioxaborolan-2-yl)butyl)piperidine-2-carboxylic acid (Intermediate 24, 40 mg, 66% yield) as a dry film and as a mixture of rotamers. $^1$H NMR (500 MHz, $CDCl_3$) δ 0.77 (2H, t), 0.91 (6H, br d), 1.20-1.24 (13H, m), 1.29 (1H, br d), 1.33-1.42 (11H, m), 1.43 (10H, s), 1.70-1.82 (1H, m), 1.83-1.90 (1H, m), 1.91-2.02 (4H, m), 3.00 (1H, t), 3.83-3.94 (1H, m), 3.96-4.07 (1H, m), 4.13 (1H, br s), 5.40 (1H, d), 6.03-6.33 (1H, m), 6.90-7.22 (1H, m); m/z: ($ES^+$) $[M+H]^+$=625.

Example 9: (2R,4S)-4-[[(2R)-2-amino-3-methyl-butanoyl]amino]-2-(4-boronobutyl)piperidine-2-carboxylic acid Trifluoroacetic acid (0.10 mL, 1.3 mmol) was added dropwise to a stirred solution of (2R,4S)-1-(tert-butoxycarbonyl)-4-((R)-2-((tert-butoxycarbonyl)amino)-3-methylbutanamido)-2-(4-(4,4,5,5-tetramethyl-1,3,2-dioxaborolan-2-yl)butyl)piperidine-2-carboxylic acid (Intermediate 24, 40 mg, 0.06 mmol) in DCM (1 mL) at room temperature. After 2 h the solution was concentrated under reduced pressure and the resulting residue was dissolved in 1 M HCl (aq) (1.0 mL, 1.0 mmol) and $Et_2O$ (1 mL). Phenylboronic acid (24 mg, 0.20 mmol) was added and the clear biphasic solution stirred at room temperature for 20 h. The mixture was diluted with $Et_2O$ (5 mL) and water (1 mL) and the layers were separated. The aqueous layer was washed with $Et_2O$. The aqueous layer was lyophilized and purified by ion exchange chromatography (PoraPak Rxn CX 20 cc column). The desired product was eluted from the column using 5% ammonia in MeOH (20 mL) to afford (2R,4S)-4-[[(2R)-2-amino-3-methyl-butanoyl]amino]-2-(4-boronobutyl)piperidine-2-carboxylic acid (Example 9, 20 mg, 91% yield) as a white solid. $^1$H NMR (500 MHz, $D_2O$) δ 0.73-0.83 (2H, m), 0.87-0.95 (6H, m), 1.14-1.23 (1H, m), 1.24-1.33 (1H, m), 1.41 (2H, quin), 1.65-1.77 (1H, m), 1.79-1.87 (1H, m), 1.88-1.98 (3H, m), 2.01-2.09 (1H, m), 2.15 (1H, dd), 3.14 (1H, d), 3.15-3.24 (1H, m), 3.31 (1H, dt), 4.11-4.20 (1H, m); m/z: ($ES^+$) $[M-H_2O+H]^+$=326.

Example 10. Efficacy of COMPOUND 12, an Arginase 1 Inhibitor, Combined with Anti-PDL 1 or Anti-PDL1 and Anti-NKG2a or Poly I:C in Preclinical Models of Cancer Methods

MC38-OVA:

Mouse MC38 colorectal cancer cells expressing OVA antigen ($5\times10^5$ cells/mouse), were subcutaneously implanted in the right flank of 6 to 8 weeks old female C57BL/6 mice. On day 6 post transplant, groups of mice were treated with vehicle (water), 30 mg/kg COMPOUND 12, 10 mg/kg Anti-PDL1 (MEDI4736), or the combination. COMPOUND 12 was formulated in water and dosed orally twice per day. MEDI4736 was formulated in 1×PBS and dosed intraperitoneally twice per week for 2 weeks. Tumor length and width was measured by caliper and tumor volume was calculated using the formula $(\text{length}\times\text{width}^2)*\pi/6$ then reported as tumor volume as calculated.

For monitoring immune cell changes tumors were harvested either four, ten or fourteen days post treatment. Tumors were excised and mechanically minced. Tumors were then incubated with tumor dissociation enzyme mix (Miltenyi Biotec) at 37° C. for 40 min in gentle MACS instrument (Miltenyi biotec). Single cell suspension were made and stained for a variety of immune cell markers to determine the immune cell changes post treatment using multicolor flow cytometry. Furthermore, the functional response of CD8+ cytotoxic T cells was evaluated by ex vivo restimulation with phorbol 12-myristate-13-acetate (PMA) and ionomycin prior to analysis.

CT.26 WT:

Mouse CT.26 WT colorectal cancer cells ($5\times10^5$ cells/mouse), were subcutaneously implanted in the right flank of 6 to 8 weeks old female Balb/C mice. On day 6 post implant, groups of mice were treated with vehicle (water), 30 mg/kg COMPOUND 12, 10 mg/kg Anti-PDL1 (MEDI4736), or the combination. Additional groups were treated with 10 mg/kg Anti-NKG2A (monalizumab), in combination with either COMPOUND 12 or MEDI4736, or a triplicate of COMPOUND 12, monalizumab and MEDI4736. COMPOUND 12 was formulated in water and dosed orally twice per day. MEDI4736 was formulated in 1×PBS and dosed intraperitoneally twice per week for 2 weeks. Monalizumab was formulated in 1×PBS and dosed intravenously twice per week for 1.5 weeks (3 doses). Tumor length and width was measured by caliper and tumor volume was calculated using the formula (length×width$^2$)*π/6 then reported as tumor volume as calculated.

LL/2:

Mouse Lewis lung (LL/2) carcinoma cells (1×10$^6$ cells/mouse), were subcutaneously implanted in the right flank of 6 to 8 weeks old C57BL/6 mice. On day 6 post implant, groups of mice were treated with vehicle (water), 30 mg/kg COMPOUND 12, 7.5 mg/kg TLR3 agonist (Poly I:C), or the combination. COMPOUND 12 was formulated in water and dosed orally twice per day. Poly I:C was formulated in water and dosed intraperitoneally 3×/week. Tumor length and width was measured by caliper and tumor volume was calculated using the formula (length×width$^2$)*π/6 then reported as tumor volume as calculated.

Results:

As shown in FIGS. 1A to 1D, FIGS. 2A to 2D, and FIGS. 3A to 3F, COMPOUND 12 monotherapy was modestly efficacious in all three mouse syngeneic tumor models. Anti-PDL1 dosed alone also showed modest efficacy in both colorectal cancer tumor models. The combination of agents demonstrated markedly stronger efficacy; 87% tumor growth inhibition in MC38-OVA and 46% overall tumor growth inhibition with one complete remission in CT.26 WT model. Addition of Anti-NKG2a to COMPOUND 12+Anti-PDL1 treatment resulted in 53% overall tumor growth inhibition and 3 complete remissions. The TLR3 agonist, Poly I:C, showed moderate monotherapy activity with TGI on day 16 of 76%. The combination of COMPOUND 12+Poly I:C resulted in 87% tumor growth inhibition.

As shown in FIGS. 4A to 4F, an in vivo PD combination study of ARG inhibitor with anti-PDL 1 in MC38-OVA model showed increases in multiple tumor immune cell populations (~4-fold CD8+ T cells, 2-fold NK cells, 2-fold CD103+ DCs) and increased CD8 T cell activation. Moreover, as shown in FIGS. 5A and 5B, ARG inhibitor resulted in an increase of IFNg and TNFa producing CD8+ T cells in the periphery (draining LN). inhibition with one complete remission in CT.26 WT model.

Figure 5A:
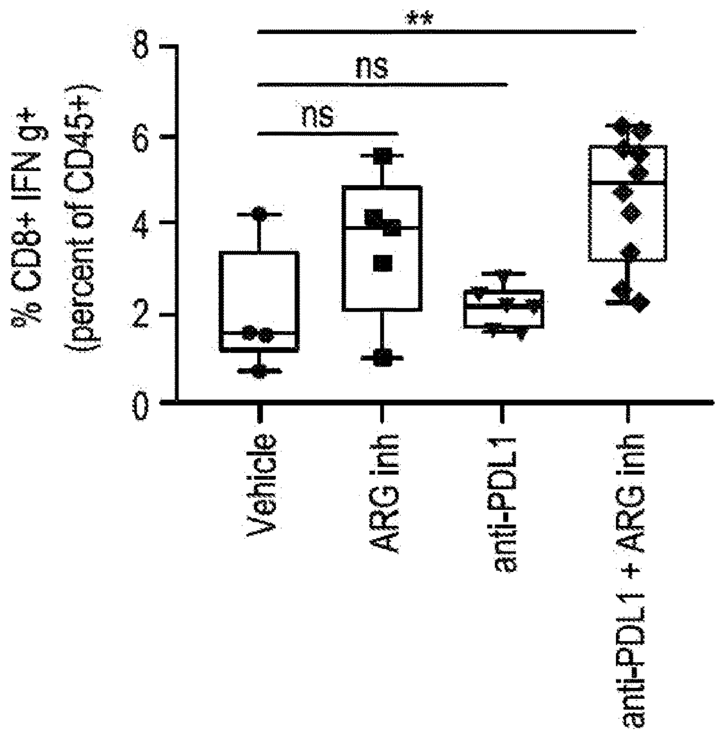
FIGS. 5A and 5B illustrate the increased IFN gamma (FIG. 5A) and TNF alpha (FIG. 5B) producing CD8+ T cell functionality in tumor draining lymph node with arginase inhibitor, anti-PDL1, and the combination of arginase inhibitor anti-PDL1.
Figure 5B:
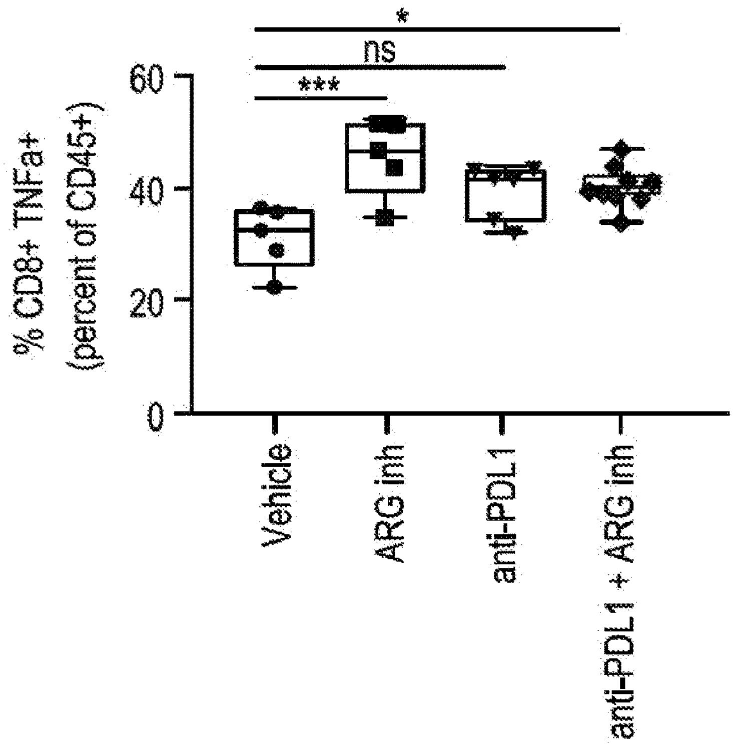
Figure 6A:
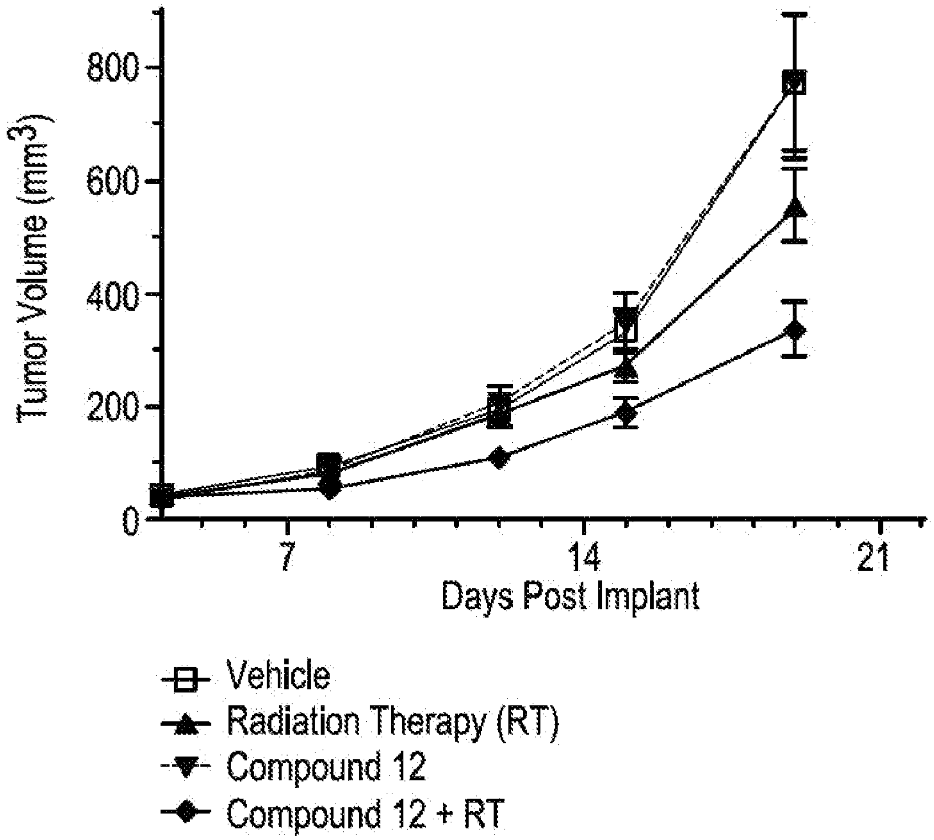
FIG. 6A illustrates the anti-tumor activity of the combination of arginase inhibitor (COMPOUND 12) and radiation therapy (RT) in the Lewis Lung syngeneic tumor model.
Figure 6B:
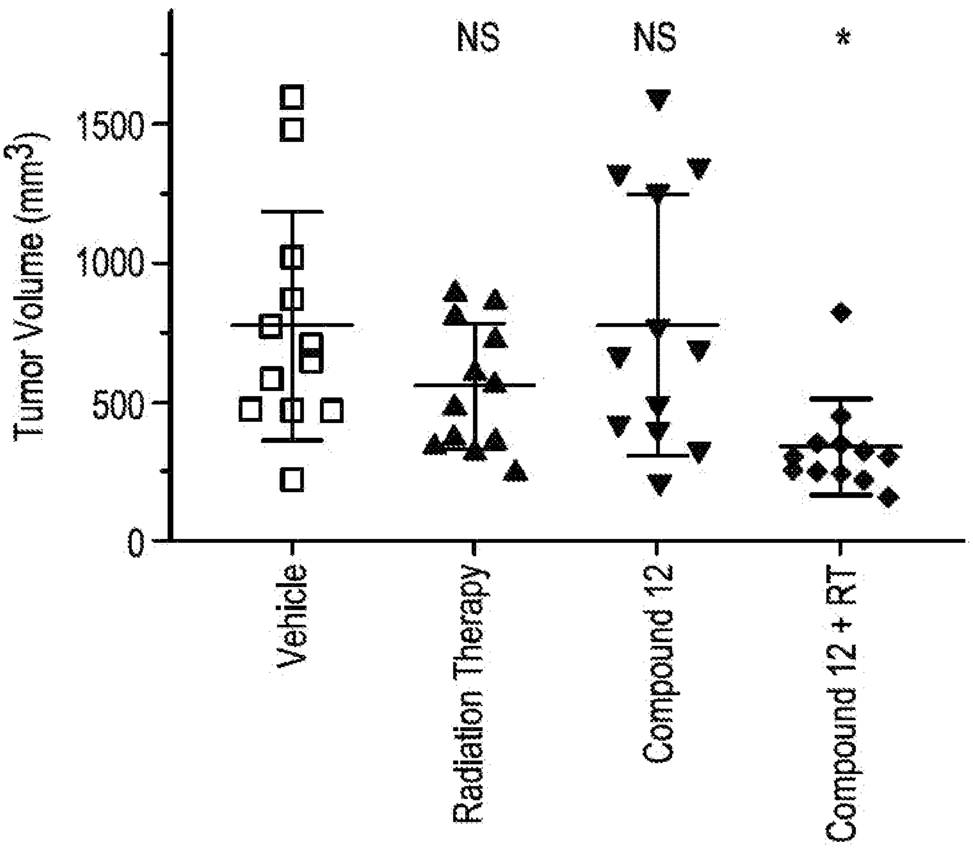
FIG. 6B illustrates that the combination of arginase inhibitor (COMPOUND12) and radiation therapy (RT) reduces Lewis Lung tumor volume at end of study (Day 19).

Example 11. Efficacy of COMPOUND 12, an Arginase 1 Inhibitor, Combined with Radio Therapy (RT) in Preclinical Models of Cancer Methods:

Six-eight week old BL/6 mice (Charles River Labs) were implanted with 1e6 LL/2 murine lung carcinoma cells subcutaneously on the right flank. At 6 days post implant, animals were randomized by mean cage tumor volume into four groups (n=12/ group). Group 1 was anesthetized for mock irradiation on days 6 and 9, and dosed with vehicle (water) PO, BID starting on day 6. Group 2 was anesthetized and given 5 Gy of radiation targeted to the tumor on days 6 and 9. Group 3 was administered AZ8400 at 30 mg/kg PO bid starting on Day 6, and Group 4 was administered AZ8400 at 30 mg/kg starting on Day 6, and anesthetized and irradiated on days 6 and 9. Body weight and tumor volume were measured twice weekly until tumors were >1500 mm3, at which point mice were humanely sacrificed Results:

As shown if FIGS. 5A and 5B, combination of COMPOUND 12 and radio therapy demonstrated markedly stronger efficacy reaching about 60% tumor growth inhibition ($p<0.05$ versus vehicle and monotherapy treatment) as compared to COMPOUND 12 dosed 30 mg/kg twice daily and Radiation Therapy (5 gray on days 6 and 9 after implant; about 30% tumor growth inhibition, $p>0.05$ versus vehicle) in the mouse syngeneic lung tumor model LL/2.

| SEQ ID NO: | Sequence | Description |
|---|---|---|
| 1 | EIVLTQSPGTLSLSPGERATLSCRASQRVSSS YLAWYQQKPGQAPRLLIYDASSRATGIPDRFS GSGSGTDFTLTISRLEPEDFAVYYCQQYGSLP WTFGQGTKVEIK | Light chain variable domain of durvalumab |
| 2 | EVQLVESGGGLVQPGGSLRLSCAASGFTFSR YWMSVWRQAPGKGLEWVANIKQDGSEKYYV DSVKGRFTISRDNAKNSLYLQMNSLRAEDTAV YYCAREGGWFGELAFDYWGQGTLVTVSS | Heavy chain variable domain of durvalumab |
| 3 | GFTFSRYWMS | CDRH1 of durvalumab |
| 4 | NIKQDGSEKYYVDSVKG | CDRH2 of durvalumab |
| 5 | EGGWFGELAFDY | CDRH3 of durvalumab |
| 6 | RASQRVSSSYLA | CDRL1 of durvalumab |
| 7 | DASSRAT | CDRL2 of durvalumab |
| 8 | QQYGSLPWT | CDRL3 of durvalumab |
| 9 | PSSLSASVGDRVTITCRASQSINSYLDWYQQK PGKAPKLLIYAASSLQSGVPSRFSGSGSGTDF TLTISSLQPEDFATYYCQQYYSTPFTFGPGTK VEIKRTVAAPSVFIFPPSDEQLKSGTASVVCLL NNFYPREAKV | Light chain variable domain of tremelimumab |
| 10 | GVVQPGRSLRLSCAASGFTFSSYGMHWVRQ APGKGLEWVAVIWYDGSNKYYADSVKGRFTI SRDNSKNTLYLQMNSLRAEDTAVYYCARDPR GATLYYYYYGMDVWGQGTTVTVSSASTKGPS | Heavy chain variable domain of tremelimumab |

-continued

| SEQ ID NO: | Sequence | Description |
|---|---|---|
| | VFPLAPCSRSTSESTAALGCLVKDYFPEPVTV SWNSGALTSGVH | |
| 11 | GFTFSSYGMH | CDRH1 of Tremelimumab |
| 12 | VIWYDGSNKYYADSV | CDRH2 of tremelimumab |
| 13 | TAVYYCARDPRGATLYYYYYGMDV | CDRH3 of tremelimumab |
| 14 | RASQSINSYLD | CDRL1 of tremelimumab |
| 15 | AASSLQS | CDRL2 of tremelimumab |
| 16 | QQYYSTPFT | CDRL3 of tremelimumab |
| 17 | EVQLVQSGAEVKKPGESLRISCKGSGYSFTSY WMNWVRQMPGKGLEWMGRIDPYDSETHYS PSFQGHVTISADKSISTAYLQWSSLKASDTAM YYCARGGYDFDVGTLYWFFDVWGQGTTVTV SSASTKGPSVFPLAPCSRSTSESTAALGCLVK DYFPEPVTVSWNSGALTSGVHTFPAVLQSSG LYSLSSWTVPSSSLGTKTYTCNVDHKPSNTK VDKRVESKYGPPCPPCPAPEFLGGPSVFLFPP KPKDTLMISRTPEVTCVVVDVSQEDPEVQFN WYVDGVEVHNAKTKPREEQFNSTYRWSVLT VLHQDWLNGKEYKCKVSNKGLPSSIEKTISKA KGQPREPQVYTLPPSQEEMTKNQVSLTCLVK GFYPSDIAVEWESNGQPENNYKTTPPVLDSD GSFFLYSRLTVDKSRWQEGNVFSCSVMHE ALHNHYTQKSLSLSLGK | Light chain variable domain of monalizumab |
| 18 | EVQLVQSGAEVKKPGATVKISCKVSGYTFTSY WMNWVQQAPGKGLEWMGRIDPYDSETHY AEKFQGRVTITADTSTDTAYMELSSLRSEDTA VYYCATGGYDFDVGTLYWFFDVWGQGTTVT VSSASTKGPSVFPLAPCSRSTSESTAALGCLV KDYFPEPVTVSWNSGALTSGVHTFPAVLQSS GLYSLSSWTVPSSSLGTKTYTCNVDHKPSNTK VDKRVESKYGPPCPPCPAPEFLGGPSVFLFPP KPKDTLMISRTPEVTCVWDVSQEDPEVQFNW YVDGVEVHNAKTKPREEQFNSTYRWSVLTVL HQDWLNGKEYKCKVSNKGLPSSIEKTISKAKG QPREPQVYTLPPSQEEMTKNQVSLTCLVKGF YPSDIAVEWESNGQPENNYKTTPPVLDSDGS FFLYSRLTVDKSRWQEGNVFSCSVMHEALHN HYTQKSLS LSLGK | Heavy chain variable domain of monalizumab |
| 19 | CDR-H1 corresponding to residues 31-35 of SEQ ID NO: 18 | CDRH1 of monalizumab |
| 20 | CDR-H2 corresponding to residues 50-66 of SEQ ID NO: 18 | CDRH2 of monalizumab |
| 21 | CDR-H3 corresponding to residues 95-102 of SEQ ID NO: 18 | CDRH3 of monalizumab |
| 22 | CDR-L1 corresponding to residues 24-34 of SEQ ID NO: 17 | CDRL1 of monalizumab |
| 23 | CDR-L2 corresponding to residues 50-56 of SEQ ID NO: 17 | CDRL2 of monalizumab |
| 24 | CDR-L3 corresponding to residues 89-97 of SEQ ID NO: 17 | CDRL3 of monalizumab |

The invention claimed is:

1. A method of treating a cancer related to arginase activity in a patient comprising administering to the patient an effective amount of a compound of Formula (Ia1) or (Ib1), or a pharmaceutically acceptable salt thereof, and an effective amount of an immunomodulatory agent;

(Ia1)

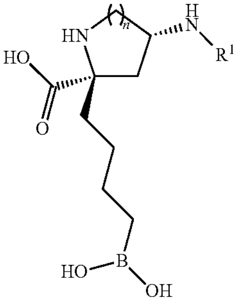

or (Ib1)

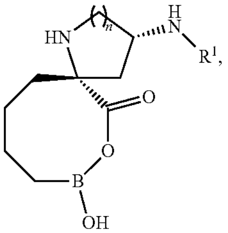

wherein $R^1$ is —H or —C(O)CH($R^{1a}$)NH$R^{1b}$, $R^{1a}$ is selected from —H, —($C_1$-$C_6$) alkyl and $CH_2OR^{1c}$;

$R^{1b}$ is —H; or alternatively, $R^{1a}$ and $R^{1b}$, together with the atom to which they are attached, form a 5-membered heterocyclic ring; and $R^{1c}$ is H or —$CH_3$.

2. The method of claim 1, wherein $R^1$ is —H or —C(O)CH($R^{1a}$)$NH_2$; and $R^{1a}$ is selected from —H or —($C_1$-$C_6$) alkyl.

3. The method of claim 1, wherein the compound of Formula (Ia1) or (Ib1) is represented by:

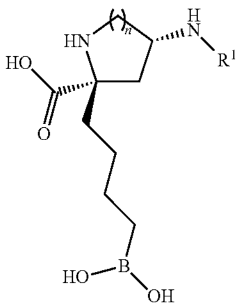

or

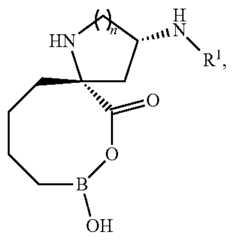

wherein $R^2$ is selected from —H or —($C_1$-$C_4$) alkyl.

4. The method of claim 1, wherein the compound of Formula (Ia1) or (Ib1) is selected from:

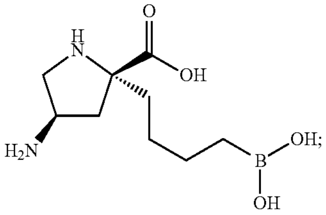

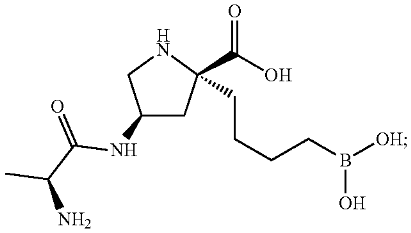

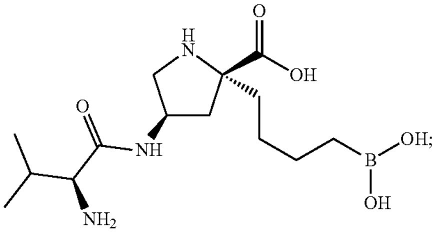

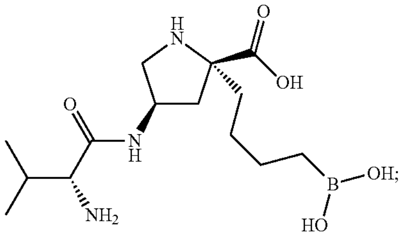

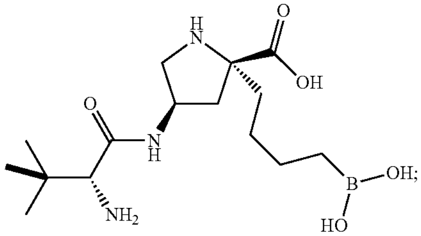

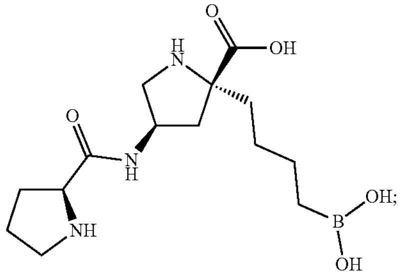

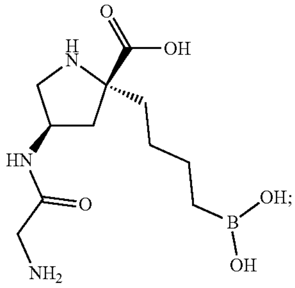

-continued

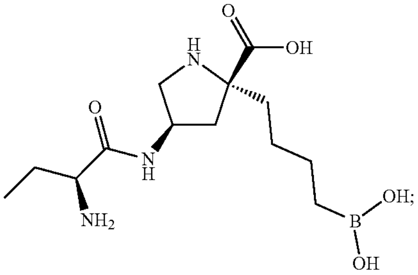

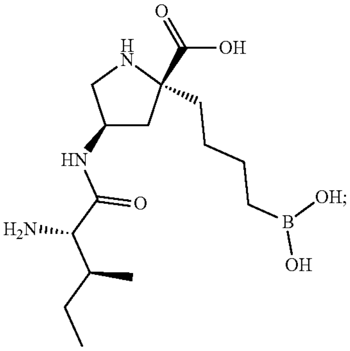

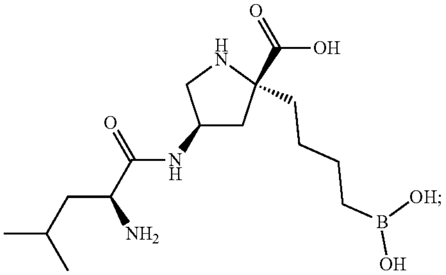

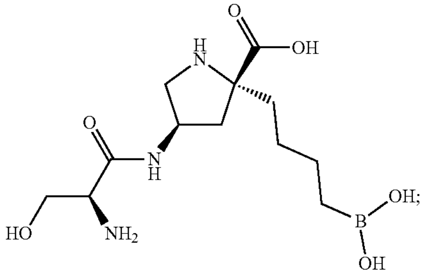

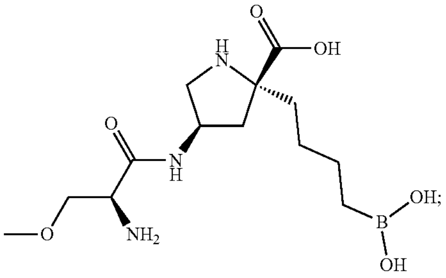

and

-continued

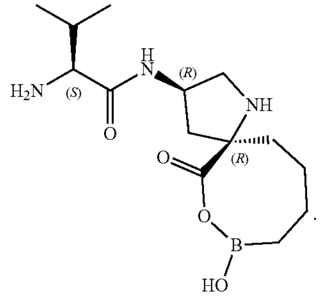

5. The method of claim 1, wherein the immunomodulatory agent is an immune checkpoint inhibitor or an immunostimulant.

6. The method of claim 5, wherein the immune checkpoint inhibitor is a CTLA-4 receptor inhibitor, a PD-1 receptor inhibitor, a PD-L1 inhibitor, a PD-L2 inhibitor, a NKG2A receptor inhibitor, or a combination thereof.

7. The method of claim 5, wherein the immunostimulant is a TLR3 agonist.

8. The method of claim 5, wherein the immune checkpoint inhibitor is an antibody or antigen-binding fragment thereof.

9. The method of claim 5, wherein the immune checkpoint inhibitor is an anti-CTLA-4 receptor antibody, an anti-PD-1 receptor antibody, an anti-PD-L1 antibody, an anti-PD-L2 antibody, an anti-NKG2A receptor antibody, or a combination thereof.

10. The method of claim 9, wherein the immune checkpoint inhibitor is durvalumab, tremelimumab, monalizumab, or a combination thereof.

11. The method of claim 1, wherein the cancer is a breast cancer, a bladder cancer, a head and neck cancer, a non-small cell lung cancer, a small cell lung cancer, a colorectal cancer, a gastrointestinal stromal tumor, a gastroesophageal carcinoma, a renal cell cancer, a prostate cancer, a liver cancer, a colon cancer, a pancreatic cancer, an ovarian cancer, a melanoma, A non-Hodgkin's lymphoma, a cutaneous T-cell lymphoma, multiple myeloma, acute myeloid leukemia (AML), myelodysplastic syndrome (MDS), chronic myeloid leukemia (CML), chronic lymphocytic leukaemia (CLL), chronic myelomonocytic leukemia (CMML), and diffuse large B-cell lymphoma (DLBCL).

12. A pharmaceutical product comprising i) a compound of Formula (Ia1) or (Ib1), or a pharmaceutically acceptable salt thereof, and ii) an immunomodulatory agent;

(Ia1)

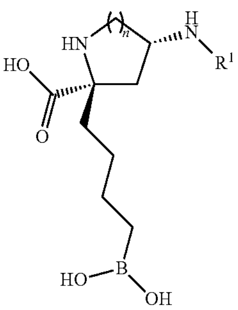

or

-continued (Ib1)

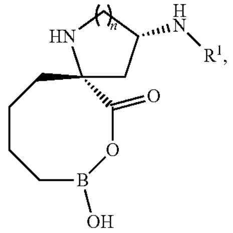

wherein $R^1$ is —H or —C(O)CH($R^{1a}$)NH$R^{1b}$;

$R^{1a}$ is selected from —H, —($C_1$-$C_6$) alkyl and $CH_2OR^{1c}$, $R^{1b}$ is —H; or alternatively, $R^{1a}$ and $R^{1b}$, together with the atom to which they are attached, form a 5-membered heterocyclic ring; and $R^{1c}$ is H or —$CH_3$.

13. The pharmaceutical product of claim 12, wherein the compound of Formula (Ia1) or (Ib1), or a pharmaceutically acceptable salt thereof and the immunomodulatory agent are present in a single dosage form.

14. The pharmaceutical product of claim 12, wherein the compound of Formula (Ia1) or (Ib1), or a pharmaceutically acceptable salt thereof and the immunomodulatory agent are present in separate dosage forms.

15. A method of treating a cancer related to arginase activity in a patient comprising administering to the patient an effective amount of a compound of Formula (Ia1) or (Ib1), or a pharmaceutically acceptable salt thereof, and an effective amount of radiation therapy;

(Ia1)

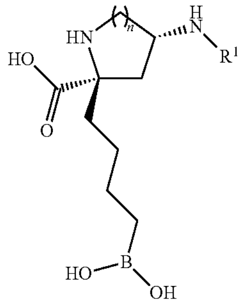

or

-continued (Ib1)

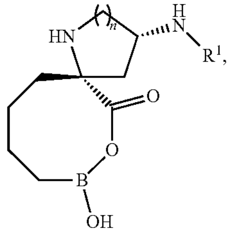

wherein $R^1$ is —H or —C(O)CH($R^{1a}$)NH$R^{1b}$;

$R^{1a}$ is selected from —H, —($C_1$-$C_6$) alkyl and $CH_2OR^{1c}$, $R^{1b}$ is —H; or alternatively, $R^{1a}$ and $R^{1b}$, together with the atom to which they are attached, form a 5-membered heterocyclic ring; and $R^{1c}$ is H or —$CH_3$.

16. The method of claim 15, wherein the compound of Formula (Ia1) or (Ib1) is represented by:

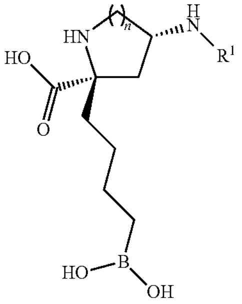

or

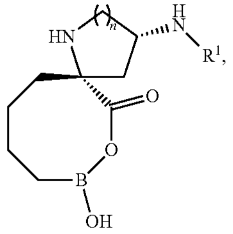

wherein $R^2$ is selected from —H or —($C_1$-$C_4$) alkyl.

17. The method of claim 15, wherein the radiation therapy is fractionated radiation therapy.

18. The method of claim 15, further comprising administering to the patient an effective amount of an immunomodulatory agent.

19. The method of claim 18, wherein the immunomodulatory agent is a CTLA-4 receptor inhibitor, a PD-1 receptor inhibitor, a PD-L1 inhibitor, a PD-L2 inhibitor, a NKG2A receptor inhibitor, or a combination thereof.

* * * * *